US009163068B2

(12) United States Patent
Khurana et al.

(10) Patent No.: US 9,163,068 B2
(45) Date of Patent: Oct. 20, 2015

(54) INFLUENZA VIRUS RECOMBINANT PROTEINS

(75) Inventors: Surender Khurana, Clarksburg, MD (US); Hana Golding, Rockville, MD (US)

(73) Assignee: The United States of America as represented by the Secretary of the Department of Health and Human Services, National Institutes of Health, Office of Technology Transfer, Washington, DC (US)

( * ) Notice: Subject to any disclaimer, the term of this patent is extended or adjusted under 35 U.S.C. 154(b) by 472 days.

(21) Appl. No.: 13/508,030

(22) PCT Filed: Nov. 2, 2010

(86) PCT No.: PCT/US2010/055166
§ 371 (c)(1),
(2), (4) Date: Aug. 14, 2012

(87) PCT Pub. No.: WO2011/056802
PCT Pub. Date: May 12, 2011

(65) Prior Publication Data
US 2012/0301504 A1    Nov. 29, 2012

Related U.S. Application Data

(60) Provisional application No. 61/257,785, filed on Nov. 3, 2009, provisional application No. 61/325,216, filed on Apr. 16, 2010.

(51) Int. Cl.
A61K 39/145    (2006.01)
C07K 14/11    (2006.01)
C07K 14/005    (2006.01)
G01N 33/559    (2006.01)
G01N 33/569    (2006.01)
A61K 39/12    (2006.01)
A61K 39/00    (2006.01)

(52) U.S. Cl.
CPC ............... *C07K 14/005* (2013.01); *A61K 39/12* (2013.01); *A61K 39/145* (2013.01); *G01N 33/559* (2013.01); *G01N 33/56983* (2013.01); *A61K 2039/55566* (2013.01); *C12N 2760/16122* (2013.01); *C12N 2760/16134* (2013.01); *G01N 2333/11* (2013.01)

(58) Field of Classification Search
None
See application file for complete search history.

(56) References Cited

U.S. PATENT DOCUMENTS 8,420,102 B2 *   4/2013   Song et al. ................. 424/201.1
2008/0124355 A1   5/2008   Bermudes
2010/0150954 A1   6/2010   Miller et al.

OTHER PUBLICATIONS

Spitsin et al., 2009 Vaccine vol. 27, pp. 1289-1292.*
Chiu et al. 2009 Bioch Biophys Res Com vol. 383, pp. 27-31.*
Verma et al., J. Virology 2012, vol. 86: No. 22, pp. 12283-12293.*
International Search Report and Written Opinion dated Mar. 28, 2011, issued in related International Patent Application No. PCT/US2010/055166, filed Nov. 2, 2010.
Spitsin et al., "Immunological assessment of plant-derived avian flu H5/HA1 variants," 2009, Vaccine, 27; 1289-1292.
Weltman et al., "Influenza A H5N1 hemagglutinin cleavable signal sequence substitutions," 2007, Biochemical and Biophysical Research Communications, 352; 177-180.
Chiu et al., "Immunological Study of HA1 domain of hemagglutinin in influenza H5N1," 2009, Biochemical and Biophysical Research Communications, 383; 27-31.
GenBank Accession No. ABP51977.1, Hemagglutinin [Influenza A virus (A/Viet Nam/1203/2004(H5N100]. May 1, 2008, Retrieved from the Internet on Mar. 16, 2011: http://www.ncbi.nlm.nih.gov/protein/ABP51977.1.

* cited by examiner

*Primary Examiner* — Mary E Mosher
*Assistant Examiner* — Myron Hill
(74) *Attorney, Agent, or Firm* — Kilpatrick Townsend & Stockton LLP

(57) ABSTRACT

The present invention includes influenza Hemagglutinin protein fragments that fold properly when expressed in bacteria.

18 Claims, 43 Drawing Sheets

FIGURE 1

```
                              5         15        25        35        45        55
                              |....|....|....|....|....|....|....|....|....|....|....|....|
A/Indonesia/5/2005(H5N1)      DQICIGYHAN NSTEQVDTIM EKNVTVTHAQ DILEKTHNGK LCDLDGVKPL ILRDCSVAGW
A/Viet Nam/1203/2004(H5N1)    DQICIGYHAN NSTEQVDTIM EKNVTVTHAQ DILEKKHNGK LCDLDGVKPL ILRDCSVAGW
A/California/04/2009(H1N1)    DTLCIGYHAN NSTDTVDTVL EKNVTVTHSV NLLEDKHNGK LCKLRGVAPL HLGKCNIAGW
A/New Caledonia/6/2008(H1N1)  DTICIGYHAN NSTDTVDTVL EKNVTVTHSV NLLENSHNGK LCLLKGIAPL QLGNCSVAGW
A/South Carolina/1/18(H1N1)   DTICIGYHAN NSTDTVDTVL EKNVTVTHSV NLLEDSHNGK LCKLKGIAPL QLGKCNIAGW
A/Denver/57(H1N1)             DTICIGYHAN NSTDTVDTVL EKNVTVTHSV NLLEDSHNGK LCRLKGKAPL QLGNCNIAGW
A/swine/Wisconsin/1/1968(H1N1) DTLCIGYHAN NSTDTVDTVL EKNVTVTHSV NLLENRHNGK LCKLKGIAPL HLGKCNIAGW
A/Hong Kong/117/77(H1N1)      DTICIGYHAN NSTDTVDTVL EKNVTVTHSV NLLEDSHNGK LCRLKGIAPL QLGKCSIAGW
A/Berkeley/1/68(H2N2)         DQICIGYHAN NSTEKVDTIL ERNVTVTHAK DILEKTHNGK LCKLNGIPPL ELGDCSIAGW
A/Victoria/210/2009(H3N2)     ATLCLGHHAV PNGTIVKTIT NDQIEVTNAT ELVQNSSTGE ICDS-PHQIL DGKNCTLIDA
A/Wisconsin/15/2009(H3N2)     ATLCLGHHAV PNGTIVKTIT NDQIEVTNAT ELVQSSSTGE ICDS-PHQIL DGKNCTLIDA
A/chicken/Alabama/1/1975(H4N8) PVICLGHHAV SNGTMVKTLT DDQVEVTAQ  ELVESQHLPE LCPS-PLRLV DGQTCDIVNG
A/mallard/Ohio/170/1999(H6N5) DRICIGHHAV NSTTQVDTIL EKNVTVTHSV ELLESKKESI FCRVLNKAPL DLMDCTTEGW
A/Netherlands/219/03(H7N7)    DKICLGHHAV SNGTKVNTLT ERGVEVVNAT ETVERTNVPR ICSK-GKRTV DLGQCGLLGT
A/duck/Alaska/702/1991(H8N2)  DRICIGYQSN NSTDTVNTLI EQNVPVTQTM EIVETEKHSA YCNTDLGAPL ELRDCKIEAV
A/Hong Kong/1073/99(H9N2)     DKICIGHQST NSTETVDTLT ETNVPVTHAK ELLHTEHNGM LCATSLGHPL ILDTCTIEGL
A/chicken/Germany/N/1949(H10N7) DRICLGHHAV ANGTIVKTLT NEQEEVTNAT ETVESTNLNK LCMK-GRSYK DLGNCHPVGM
A/chicken/Netherlands/7/99(H11N2) DEICIGYLSN NSTDKVDTII ENNVTVTSSV ELVETEHTGS FCSINGKQPI SLGDCSFAGW
A/mallard/Alberta/60/1976(H12N5) DKICIGYQTN NSTETVNTLS EQNVPVTQVE ELVHGGIDPI LCGTELGSPL VIDDCSLEGL
A/gull/Maryland/704/1977(H13N6) DRICVGYLST NSSERVDTLL ENGVPVTSSI DLIETNHTGT YCSLNGVSPV HLGDCSFEGW
A/mallard duck/Astrakhan/263/1982(H14N5) PIICLGHHAV ENGTSVKTLT DNHVEVVSAK ELVETNHTDE LCPS-PLKLV DGQDCDLING
A/duck/Australia/341/83(H15N8) DKICLGHHAV ANGTKVNTLT ERGVEVVNAT ETVEITGINK VCTK-GKKAV DLGSCGILGT
A/shorebird/New Jersey/840/1986(H16N3) DKICIGYLSN NSSDTVDTLT ENGVPVTSSI DLVETNHTGT YCSLNGISPI HLGDCSFEGW
```

FIGURE 1 (cont'd)

```
                                        ....|....|....|....|....|....|....|....|....|....|....|....|
                                            65        75        85        95       105       115
A/Indonesia/5/2005{H5N1}                LLGNPMCDEF INVPEWSYIV EKANPTNDLC YPGSFNDYEE LKHLLSRINH FEKIQIIP-K
A/Viet Nam/1203/2004{H5N1}              LLGNPMCDEF INVPEWSYIV EKANPVNDLC YPGDFNDYEE LKHLLSRINH FEKIQIIP-K
A/California/04/2009{H1N1}              ILGNPECESL STASSWSYIV ETPSSDNGTC YPGDFIDYEE LREQLSSVSS FERFEIFPKT
A/New Caledonia/6/2008{H1N1}            ILGNPECELL ISKESWSYIV EKPNPENGTC YPGHFADYEE LREQLSSVSS FERFEIFPKE
A/South Carolina/1/18{H1N1}             LLGNPECDLL LTASSWSYIV ETSNSENGTC YPGDFIDYEE LREQLSSVSS FEKFEIFPKT
A/Denver/57{H1N1}                       VLGNPECESL LSNRSWSYIA ETPNSENGTC YPGDFADYEE LREQLSSVSS FERFEIFPKE
A/swine/Wisconsin/1/1968{H1N1}          LLGNPECELL FTVSSWSYIV ETSNSDNGTC YPGDFINYEE LREQLSSVSS FEKFEIFPKT
A/Hong Kong/117/77{H1N1}                ILGNPECESL FSKKSWSYIA ETPNSENGTC YPGYFADYEE LREQLSSVSS FERFEIFPKE
A/Berkeley/1/68{H2N2}                   LLGNPECDRL LSVPEWSYIM EKENPRYSLC YPGSFNDYEE LKHLLSSVKH FEKVKILP-K
A/Victoria/210/2009{H3N2}               LLGDPQCDGF QN-KKWDLFV ERSKAYS-NC YPYDVPDYAS LRSLVA---S SGTLEFNNES
A/Wisconsin/15/2009{H3N2}               LLGDPQCDDF QN-KKWDLFV ERSKAYS-NC YPYDVPDYAS LRSLVA---S SGTLEFNNES
A/chicken/Alabama/1/1975{H4N8}          ALGSPGCNHL NG-AEWDVFI ERPTAVD-TC YPFDVPDYQS LRSILA---N NGKFEFIVEK
A/mallard/Ohio/170/1999{H6N5}           ILGNPRCDNL LGDQSWSYIV ERPDAKNGIC YPGVLKETEE LKALIGSIDS IQRFEMFP-K
A/Netherlands/219/03{H7N7}              ITGPPQCDQF LE-FSADLII ERREGSD-VC YPGKFVNEEA LRQILR---E SGGIDKETMG
A/duck/Alaska/702/1991{H8N2}            IYGNPKCDIH LKDQGWSYIV ERPSAPEGMC YPGSVENLEE LRFVFSNAAS YKRIRLFD-Y
A/Hong Kong/1073/99{H9N2}               VYGNPSCDLL LGGREWSYIV ERSSAVNGTC YPGNVENLEE LRTLFSSASS YQRIQIFP-D
A/chicken/Germany/N/1949{H10N7}         LIGTPVCDFH LT-GTWDTLI ERENAIA-HC YPGATINEEA LRQKIM---E SGGISKMSTG
A/mallard/Netherlands/7/99{H11N2}       ILGNPMCDDL IGKTSWSYIV EKPNPTNGIC YPGTLEDEEE LRLKFSGVLE FSKFEAFT-S
A/duck/Alberta/60/1976{H12N5}           ILGNPKCDLY LNGREWSYIV ERPKEMEGVC YPGSIENQEE LRSLFSSIKK YERVKMFD-F
A/gull/Maryland/704/1977{H13N6}         IVGNPEACTSN FGTREWSYLI EDPAAPHGLC YPGELNNNGE LRHLFSGIRS FSRTELIP-P
A/mallard duck/Astrakhan/263/1982{H14N5} ALGSPGCDRL QD-TTWDVFI ERPTAVD--TC YPFDVPDYQS LRSILA---S SGSLEFIAEQ
A/duck/Australia/341/83{H15N8}          IIGFPQCDSH LK-FKADLII ERRNSSD-IC YPGKFTNEEA LRQIIR---E SGGIDKEPMG
A/shorebird/New Jersey/840/1986{H16N3}  IVGNPSCATN INIREWSYLI EDPNAPNKLC FPGELDNNGE LRHLFSGVNS FSRTELIS-P
```

FIGURE 1 (cont'd)

```
                                         ....|....| ....|....| ....|....| ....|....| ....|....| ....|....|
                                            125        135        145        155        165        175
A/Indonesia/5/2005{H5N1}                 SSWSDHEASS GVSSACPY-L GSPSFFRNVV WLIKKN-ST- YPTIKKSYNN TNQEDLLVLW
A/Viet Nam/1203/2004{H5N1}               SSWSSHEASL GVSSACPY-Q GKSSFFRNVV WLIKKN-ST- YPTIKRSYNN TNQEDLLVLW
A/California/04/2009{H1N1}               SSWPNHDSNK GVTAACPH-A GAKSFYKNLI WLVKKG-NS- YPKLSKSYIN DKGKEVLVLW
A/New Caledonia/6/2008{H1N1}             SSWPNH-TVT GVSASCSH-N GESSFYRNLL WLTGKN-GL- YPNLSKSYAN NKEKEVLVLW
A/South Carolina/1/18{H1N1}              SSWPNHETTK GVTAACSY-A GASSFYRNLL WLTKKG-SS- YPKLSKSYVN NKGKEVLVLW
A/Denver/57{H1N1}                        RSWPNH-TTR GVTAACPH-A RKSSFYKNLV WLTEAN-GS- YPNLSRSYVN NQEKEVLVLW
A/swine/Wisconsin/1/1968{H1N1}           SSWPNHETNR GVTAACPY-A GANSFYRNLI WLVKKG-SS- YPKLSKSYVN NKGKEVLVLW
A/Hong Kong/117/77{H1N1}                 RSWPKHNVTR GVTASCSH-K GKSSFYRNLL WLTEKN-GS- YPNLSKSYVN NKEKEVLVLW
A/Berkeley/1/68{H2N2}                    DGWTQHETTG G-SKACAV-S GKPSFFRNMV WLTKKG-PN- YPVAKGSYNN TSGEQMLIIW
A/Victoria/210/2009{H3N2}                FNW-TGVTQN GTSSACIR-R SKNSFFSRLN WLTHLN--FK YPALNVTMPN NEQFDKLYIW
A/Wisconsin/15/2009{H3N2}                FNW-TGVTQN GTSSACIR-R SKNSFFSRLN WLTHLN--FK YPALNVTMPN NEQFDKLYIW
A/chicken/Alabama/1/1975{H4N8}           FQW-NTVKQN GKSGACKR-A NENDFFTNLN WLTKSDG-NA YPLQNLTKVN NGDYARLYIW
A/mallard/Ohio/170/1999{H6N5}            NTWTGVDTSS GVSSACPY-N GGSSFYRNLL WIIKTR-SDP YSLVKGTYTN TGSQPILYFW
A/Netherlands/219/03{H7N7}               FTY-SGIRTN GTTSACRR-S G-SSFYAEMK WLLSNTDNAA FPQMTKSYKN TRKDPALIIW
A/duck/Alaska/702/1991{H8N2}             SRWNVTSS-- GTSKACNAST GGQSFYRSIN WLTKKK-PDT YDFNEGSYVN NEDGDIIFLW
A/Hong Kong/1073/99{H9N2}                TTWNVTYT-- GTSRACS--- --GSFYRSMR WLTQK--SGF YPVQDAQYTN NRGKSILFVW
A/chicken/Germany/N/1949{H10N7}          FTYGSSITSA GTTKACMR-N GGDSFYAELK WLVSKTKGQN FPQTTNTYRN TDTAEHLIIW
A/mallard/Netherlands/7/99{H11N2}        NGWGAVNSGA GVTAACKF-G SSNSFFRNMX WLIHQS-GT- YPVIKRTFNN TKGRDVLIVW
A/duck/Alberta/60/1976{H12N5}            TKWNVTYT-- GTSKACNNTS NQGSFYRSMR WLTLK--SGQ FPVQTDEYKN TRDSDIVFTW
A/gull/Maryland/704/1977{H13N6}          TSWGEVLD-- GTTSACRDNT GTNSFYRNLV WFIKKN-NR- YPVISKTYNN TTGRDVLVLW
A/mallard duck/Astrakhan/263/1982{H14N5} FTW-NGVKVD GSSSACLR-G GRNSFFSRLN WLTKATN-GN YGPINVTKEN TGSYVRLYLW
A/duck/Australia/341/83{H15N8}           FRY-SGIKTD GATSACKR-T V-SSFYSEMK WLLSSKDNQV FPQLNQTYRN NRKEPALIVW
A/shorebird/New Jersey/840/1986{H16N3}   SKWGDVLD-- GVTASCLD-K GASSFYRNLV WLVKQN-DR- YPVVRGDYNN TTGRDVLVLW
```

FIGURE 1 (cont'd)

```
                                    185         195         205         215         225         235
                                    |....|....|....|....|....|....|....|....|....|....|....|....|
A/Indonesia/5/2005{H5N1}            GIHHPNDAAE  QTRLYQNPTT  YISIGTSTLN  QRLVPKIATR  SKVNGQSGRM  EFFWTILKPN
A/Viet Nam/1203/2004{H5N1}          GIHHPNDAAE  QTKLYQNPTT  YISVGTSTLN  QRLVPRIATR  SKVNGQSGRM  EFFWTILKPN
A/California/04/2009{H1N1}          GIHHPSTSAD  QQSLYQNADT  YVFVGSSRYS  KKFKPEIAIR  PKVRDQEGRM  NYYWTLVEPG
A/New Caledonia/6/2008{H1N1}        GVHHPPSIND  QKTLYHTENA  YVSVVFSHYS  RKFTPEIAKR  PKVRDQEGRI  NYYWTLLEPG
A/South Carolina/1/18{H1N1}         GVHHPFTGTD  QQSLYQNADA  YVSVGSSKYN  RRFTPEIAAR  PKVRDQAGRM  NYYWTLLEPG
A/Denver/57{H1N1}                   GVHHPSNIEE  QRALYRKDNA  YVSVVSSNYN  RRFTPEIAKR  PKVRDQSGRM  NYYWTLLEPG
A/swine/Wisconsin/1/1968{H1N1}      GIHHPPTSTD  QQSLYQNADA  YVFVGSSKYN  RKFKPEIAAR  PKVRGQAGRM  NYYWTLLEPG
A/Hong Kong/117/77{H1N1}            GVHHPSNIED  QKTIYRKENA  YVSVVSSNYN  RRFTPEIAER  PKVRGQAGRI  NYYWTLLEPG
A/Berkeley/1/68{H2N2}               GVHHPNDEAE  QRALYQEVGT  YVSEATSTLN  KRSTPEIAAR  PKVSGLGSRM  EFSWTLLDMW
A/Victoria/210/2009{H3N2}           GVHHPVTDKD  QIFLYAQASG  RITVSTKRSQ  QTVIPNIGSR  PRVRNIPTRI  SIYWTIVKPG
A/Wisconsin/15/2009{H3N2}           GVHHPGTDKD  QIFPYAQASG  RITVSTKRSQ  QTAIPNIGSR  PRVRNIPSRI  SIYWTIVKPG
A/chicken/Alabama/1/1975{H4N8}      GVHHPSTDTE  QTNLYENNPG  RVTVSTKTSQ  TSVVPNIGSR  PWVRGQSGRI  SFYWTIVEPG
A/mallard/Ohio/170/1999{H6N5}       GVHHPPDDVE  QANLIGLGTR  YVRMGTESMN  FAKGPEIADR  PPANGQRGRI  DYYWSVLKPG
A/Netherlands/219/03{H7N7}          GIHHSGSTTE  QTKLYGSGNK  LITVGSSNYQ  QSFVPSPGAR  PQVNGQSGRI  DFHWLILNPN
A/duck/Alaska/702/1991{H8N2}        GIHHPPDTKE  QTTLYKNANT  LSSVTTNTIN  RSFQPNIGPR  PLVRGQQGRM  DYYWGILKRG
A/Hong Kong/1073/99{H9N2}           GIHHPPTYTE  QTNLYIRNDT  TTSVTTEDLN  RTFKPVIGPR  PLVNGLQGRI  DYYWSVLKPG
A/chicken/Germany/N/1949{H10N7}     GIHHPSSTQE  KNDLYGTQSL  SISVESSTYQ  NNFVPVVGAR  PQVNGQSGRI  DFHWTLVQPG
A/mallard/Netherlands/7/99{H11N2}   GIHHPATLKE  HQDLYKKDSS  YVAVGSETYN  RRFTPEISTR  PKVNGQAGRM  TFYWTMVKPG
A/duck/Alberta/60/1976{H12N5}       AIHHPPTSDE  QVKLYKNPDT  LSSVTTDEIN  RSFKPNIGPR  PLVRGQQGRM  DYYWAVLKPG
A/gull/Maryland/704/1977{H13N6}     GIHHPVSVDE  TKTLYVNSDP  YTLVSTKSWS  EKYKLETGVR  FGYNGQPSWM  KIYWSLIHPG
A/mallard duck/Astrakhan/263/1982{H14N5}  GVHHPSSDNE  QTDLYKVATG  RVTVSTRSDQ  ISIVPNIGSR  PRVRNQSGRI  SIYWTLVNPG
A/duck/Australia/341/83{H15N8}      GVHHSSSLDE  QNKLYGAGNK  LITVGSSKYQ  QSFSPSPGDR  PKVNGQAGRI  DFHWMLLDPG
A/shorebird/New Jersey/840/1986{H16N3}  GIHHPDTETT  ATKLYVNKNP  YTLVSTKEWS  KRYELEIGTR  IG-DGQRSWM  KIYWHLMHPG
```

FIGURE 1 (cont'd)

```
                                        ....|....|....|....|....|....|....|....|....|....|....|
                                          245        255        265        275        285        295
A/Indonesia/5/2005{H5N1}                DAINFESNGN FIAPEYAYKI VK-------- KGDSAIMKS- ELEYGNCNTK CQTPMGAINS
A/Viet Nam/1203/2004{H5N1}              DAINFESNGN FIAPEYAYKI VK-------- KGDSTIMKS- ELEYGNCNTK CQTPMGAINS
A/California/04/2009{H1N1}              DKITFEATGN LVVPRYAFAM ER-------- NAGSGIIIS- DTPVHDCNTT CQTPKGAINT
A/New Caledonia/6/2008{H1N1}            DTIIFEANGN LIAPRYAFAL SR-------- GFGSGIINS- NAPMDKCDAK CQTPQGAINS
A/South Carolina/1/18{H1N1}             DTIIFEATGN LIAPWYAFAL NR-------- GSGSGIITS- DAPVHDCNTK CQTPHGAINS
A/Denver/57{H1N1}                       DTIIFEATGN LIAPWYAFAL SR-------- GPGSGIITS- NAPLDECDTK CQTPQGAINS
A/swine/Wisconsin/1/1968{H1N1}          DTIIFEATGN LVVPRYAFAM NR-------- GSGSGIIIS- DAPVHDCNTK CQTPKGAINT
A/Hong Kong/117/77{H1N1}                DTIIFEANGN LIAPWYAFAL SR-------- GFGSGIITS- NASMDECDTK CQTPQGAINS
A/Berkeley/1/68{H2N2}                   DTISFESTGN LVAPEYGFKI SK-------- RGSSGIMKT- EGTLENCETK CQTPLGAINT
A/Victoria/210/2009{H3N2}               DILLINSTGN LIAPRGYFKM QSG------- --KSSIMRSD APIG-KCNSE CITPNGSIPN
A/Wisconsin/15/2009{H3N2}               DILLINSTGN LIAPRGYFKI RSG------- --KSSIMRSD APIG-KCNSE CITPNGSIPN
A/chicken/Alabama/1/1975{H4N8}          DIIVFNTIGN LIAPRGHYKL NSQK------ --KSTILNTA VPIG-SCVSK CHTDRGSITT
A/mallard/Ohio/170/1999{H6N5}           ETLNVESNGN LIAPWYAYKF TNS------- RNKGAIFKS- DLPIENCDAV CQTIAGAINT
A/Netherlands/219/03{H7N7}              DTVTIFSFNGA FIAPDRASFL R-------- -GKSMGIQSE VQVDANCEGD CYHSGGTIIS
A/duck/Alaska/702/1991{H8N2}            ETLKIRTNGN LIAPEFGYLL KG-------- ESHGRIIQNE DIPIGNCKTK CQTYAGAINS
A/Hong Kong/1073/99{H9N2}               QTLRVRSNGN LIAPWYGHVL SG-------- GSHGRILKT- DLKGGNCVVQ CQTEKGGLNS
A/chicken/Germany/N/1949{H10N7}         DNITFSDNGG LIAPSRVSKL T-------- -GRDLGIQSE ALIDNSCESK CFWRGGSINT
A/mallard/Netherlands/77/99{H11N2}      ESITFESNGA FLAPRYAFEI VS-------- VGNGKLFRS- ELSIESCSTK CQTEVGGINT
A/duck/Alberta/60/1976{H12N5}           QTVKIQTNGN LIAPEYGHLI TG-------- KSHGRILKN- NLPMGQCVTE CQLNEGVMNT
A/gull/Maryland/704/1977{H13N6}         EMITFESNGG FLAPRYGYII EE-------- YGKGRIFQS- RIRMSRCNTK CQTSVGGINT
A/mallard duck/Astrakhan/263/1982{H14N5} DSIIFNSIGN LIAPRGHYKI SKST------ --KSTVLKSD KRIG-SCTSP CLTDKGSIQS
A/duck/Australia/341/83{H15N8}          DTVTFTFNGA FIAPDRATFL RSNAPSGVEY NGKSLGIQSD AQIDESCEGE CFYSGGTINS
A/shorebird/New Jersey/840/1986{H16N3}  ERIMFESNGG LLAPRYGYII EK-------- YGTGRIFQS- GIRMAKCNTK CQTSMGGVNT
```

FIGURE 1 (cont'd)

```
                              305         315         325         335         345         355
                         ....|....|....|....|....|....|....|....|....|....|....|....|
A/Indonesia/5/2005{H5N1}         SMPFHNIHPL TIGECPKYVK SNRLVLATGL RNSPQRESRK KKRGLFGAIA GFIEGGWQGM
A/Viet Nam/1203/2004{H5N1}       SMPFHNIHPL TIGECPKYVK SNRIVLATGL RNSPQRERRR KKRGLFGAIA GFIEGGWQGM
A/California/04/2009{H1N1}       SLPFQNIHPI TIGKCPKYVK STKLRLATGL RNIPSIQSR- ----GLFGAIA GFIEGGWTGM
A/New Caledonia/6/2008{H1N1}     SLPFQNVHPV TIGECPKYVR SAKLRMVTGL RNIPSIQSR- ----GLFGAIA GFIEGGWTGM
A/South Carolina/1/18{H1N1}      SLPFQNIHPV TIGECPKYVR STKLRMATGL RNIPSIQSR- ----GLFGAIA GFIEGGWTGM
A/Denver/57{H1N1}                SLPFQNIHPV TIGECPKYVR STKLRMVTGL RNIPSVQSR- ----GLFGAIA GFIEGGWTGM
A/swine/Wisconsin/1/1968{H1N1}   SLPFQNIHPV TIGECPKYVR STKLRMATGL RNIPSIQSR- ----GLFGAIA GFIEGGWTGM
A/Hong Kong/117/77{H1N1}         SLPFQNVHPV TIGECPKYVR STKLRMVTGL RNIPSIQSR- ----GLFGAIA GFIEGGWTGM
A/Berkeley/1/68{H2N2}            TLPFHNVHPL TIGECPKYVK SEKIVLATGL RNVPQIESR- ----GLFGAIA GFIEGGWEGM
A/Victoria/210/2009{H3N2}        DKPFQNVNRI TYGACPRYVK QNTLKLATGM RNVPEKQTRG ----IFGAIA GFIENGWEGM
A/Wisconsin/15/2009{H3N2}        DKPFQNVNRI TYGACPRYVK QNTLKLATGM RNVPEKQTRG ----IFGAIA GFIENGWEGM
A/chicken/Alabama/1/1975{H4N8}   TKPFQNISRI SIGDCPKYVK QGSLKLATGM RNIPEKATRG ----LFGAIA GFIENGWQGL
A/mallard/Ohio/170/1999{H6N5}    NKTFQNVSPI WIGECPKYVK SKSLKLATGL RNVPQVKTR- ----GLFGAIA GFIEGGWTGM
A/Netherlands/219/03{H7N7}       NLPFQNINSR AVGKCPRYVK QESLLLATGM KNVPEIPKRR R-RGLFGAIA GFIEGGWEGL
A/duck/Alaska/702/1991{H8N2}     SKPFQNASRH YMGECPKYVK KASLRLAVGL RNTPSVEEK- ----GLFGAIA GFIEGGWSGM
A/Hong Kong/1073/99{H9N2}        TLPFHNISKY AFGTCPKYVR VNSLKLAVGL RNVPARSSR- ----GLFGAIA GFIEGGWPGL
A/chicken/Germany/N/1949{H10N7}  KLPFQNLSPR TVGQCPKYVN QRSLLATGM RNVPEVVQGR ----GLFGAIA GFIENGWEGM
A/mallard/Netherlands/7/99{H11N2} NKSFHSVHRN TIGDCPKYVN VKSLKLATGL RNVPAIASR- ----GLFGAIA GFIEGGWPGL
A/duck/Alberta/60/1976{H12N5}    SKPFQNTSKH YIGKCPKYIP SGSLKLAIGL RNVPQVQDR- ----GLFGAIA GFIEGGWPGL
A/gull/Maryland/704/1977{H13N6}  NRTFQNIDKN ALGDCPKYIK SGQLKLATGL RNVPAISNR- ----GLFGAIA GFIEGGWPGL
A/mallard duck/Astrakhan/263/1982{H14N5} DKPFQNVSRI AIGNCPKYVK QGSLMLATGM RNIPGKQAKG ----LFGAIA GFIENGWQGL
A/duck/Australia/341/83{H15N8}   PLPFQNIDSW AVGRCPRYVK QSSLPLALGM KNVPEKIHTR ---GLFGAIA GFIENGWEGL
A/shorebird/New Jersey/840/1986{H16N3} NKTFQNIERN ALGDCPKYIK SGQIKLATGL RNVPSIGER- ----GLFGAIA GFIEGGWPGL
```

FIGURE 1 (cont'd)

```
                                        |....|....|....|....|....|....|....|....|....|....|....|
                                           365       375       385       395       405       415
A/Indonesia/5/2005{H5N1}                VDGWYGYHHS NEQGSGYAAD KESTQKAIDG VTNKVNSIID KMNTQFEAVG REFNNLERRI
A/Viet Nam/1203/2004{H5N1}              VDGWYGYHHS NEQGSGYAAD KESTQKAIDG VTNKVNSIID KMNTQFEAVG REFNNLERRI
A/California/04/2009{H1N1}              VDGWYGYHHQ NEQGSGYAAD LKSTQNAIDE ITNKVNSVIE KMNTQFTAVG KEFNHLEKRI
A/New Caledonia/6/2008{H1N1}            VDGWYGYHHQ NEQGSGYAAD QKSTQNAING ITNKVNSVIE KMNTQFTAVG KEFNKLERRM
A/South Carolina/1/18{H1N1}             IDGWYGYHHQ NEQGSGYAAD QKSTQNAING ITNKVNSVIE KMNTQFTAVG KEFNNLERRI
A/Denver/57{H1N1}                       MDGWYGYHHQ NEQGSGYAAD QKSTQNAING ITNKVNSVIE KMNTQFTAVG KEFNKLEKRM
A/swine/Wisconsin/1/1968{H1N1}          IDGWYGYHHQ NGQGSGYAAD QKSTQNAIDG ITNKVNSIIE KMNMQFTAVG KEFNKLEKRI
A/Hong Kong/117/77{H1N1}                IDGWYGYHHQ NEQGSGYAAD QKSTQNAING ITNKVNSVIE KMNTQFTAVG KEFNKLEKRM
A/Berkeley/1/68{H2N2}                   VDGWYGYHHS NDQGSGYAAD KESTQKAFDG ITNKVNSVIE KMNTQFEAVG KEFSNLEKRL
A/Victoria/210/2009{H3N2}               VDGWYGFRHQ NSEGRGQAAD LKSTQAAIDQ INGKLNRLIG KTNEKFHQIE KEFSEVEGRI
A/Wisconsin/15/2009{H3N2}               VDGWYGFRHQ NSEGRGQAAD LKSTQAAIDQ INGKLNRLIG KTNEKFHQIE KEFSEVEGRI
A/chicken/Alabama/1/1975{H4N8}          IDGWYGFRHQ NAEGTGTAAD LKSTQAAIDQ INGKLNRLIE KTNEKYHQIE KEFEQVEGRI
A/mallard/Ohio/170/1999{H6N5}           VDGWYGYHHE NSQGSGYAAD KESTQNAIDG ITNKVNSIID KMNTQFEAVE HEFSNLERRI
A/Netherlands/219/03{H7N7}              IDGWYGFRHQ NAQGEGTAAD YKSTQSAIDQ ITGKLNRLIE KTNQQFELID NEFTEVERQI
A/duck/Alaska/702/1991{H8N2}            IDGWYGFHHS NSEGTGMAAD QKSTQEAIDK ITNKINNIVD KMNREFEVMN HEFSEVEKRI
A/Hong Kong/1073/99{H9N2}               VAGWYGFQHS NDQGVGMAAD RDSTQKAIDK ITSKVNNIVD RMNKQYEIID HEFSEVETRL
A/chicken/Germany/N/1949{H10N7}         VDGWYGFRHQ NAQGTGQAAD YKSTQAAIDQ ITGKLNRLIE KTNTEFESIE SEFSETEHQI
A/mallard/Netherlands/7/99{H11N2}       INGWYGFQHR NEEGTGIAAD RESTQKAVDQ ITSKVNNIVD RMNTNFESLQ HEFSEIEERI
A/duck/Alberta/60/1976{H12N5}           VAGWYGFQHQ NAEGTGIAAD RDSTQRAIDN MQNKLNNVID KMNKQFEVVN HEFSEVESRI
A/gull/Maryland/704/1977{H13N6}         INGWYGFQHQ NEQGTGIAAD KESTQKAIDQ ITTKINNIID KMNGNYDSIR GEFNQVEKRI
A/mallard duck/Astrakhan/263/1982{H14N5} IDGWYGFRHQ NAEGTGTAAD LKSTQAAIDQ INGKLNRLIE KTNEKYHQIE KEFEQVEGRI
A/duck/Australia/341/83{H15N8}          IDGWYGFRHQ NAQGQGTAAD YKSTQAAIDQ ITGKLNRLIE KTNTQFELID NEFTEVEQQI
A/shorebird/New Jersey/840/1986{H16N3}  INGWYGFQHQ NEQGTGIAAD KASTQKAINE ITTKINNIIE KMNGNYDSIR GEFNQVEKRI
```

FIGURE 1 (cont'd)

```
                                    .....|....|....|....|....|....|....|....|....|....|....|....|
                                        425        435        445        455        465        475
A/Indonesia/5/2005{H5N1}            ENLNKKMEDG FLDVWTYNAE LLVLMENERT LDFHDSNVKN LYDKVRLQLR DNAKELGNGC
A/Viet Nam/1203/2004{H5N1}          ENLNKKMEDG FLDVWTYNAE LLVLMENERT LDFHDSNVKN LYDKVRLQLR DNAKELGNGC
A/California/04/2009{H1N1}          ENLNKKVDDG FLDIWTYNAE LLVLLENERT LDYHDSNVKN LYEKVRSQLK NNAKEIGNGC
A/New Caledonia/6/2008{H1N1}        ENLNKKVDDG FIDIWTYNAE LLVLLENERT LDFHDSNVKN LYEKVKSQLK NNAKEIGNGC
A/South Carolina/1/18{H1N1}         ENLNKKVDDG FLDIWTYNAE LLVLLENERT LDFHDSNVRN LYEKVKSQLK NNAKEIGNGC
A/Denver/57{H1N1}                   ENLNKKVDDG FMDIWTYNAE LLVLLENERT LDFHDSNVKN LYEKVKNQLR NNAKEIGNGC
A/swine/Wisconsin/1/1968{H1N1}      ENLNKKVDDG FLDVWTYNAE LLVLLENERT LDFHDSNVKN LYEKVRSQLR NNAKEIGNGC
A/Hong Kong/117/77{H1N1}            ENLNKKVDDG FLDIWTYNAE LLVLLENERT LDFHDSNVKN LYEKVKSQLK NNAKEIGNGC
A/Berkeley/1/68{H2N2}               ENLNKKMEDG FLDVWTYNAE LLVLMENERT LDFHDSNVKN LYDKVRMQLR DNVKELGNGC
A/Victoria/210/2009{H3N2}           QDLEKYVEDT KIDLWSYNAE LLVALENQHT IDLTDSEMNK LFEKTKKQLR ENAEDMGNGC
A/Wisconsin/15/2009{H3N2}           QDLEKYVEDT KIDLWSYNAE LLVALENQHT IDLTDSEMNK LFEKTKKQLR ENAEDMGNGC
A/chicken/Alabama/1/1975{H4N8}      QDLEKYVEDT KIDLWSYNAE LLVALENQHT IDVTDSEMDK LFERVRRQLR ENAEDKGNGC
A/mallard/Ohio/170/1999{H6N5}       GNLNKRMEDG FLDVWTYNAE LLVLLENERT LDMHDANVKN LHEKVKSQLK DNAKDLGNGC
A/Netherlands/219/03{H7N7}          GNVINWTRDS MTEVWSYNAE LLVAMENQHT IDLADSEMNK LYERVKRQLR ENAEEDTGC
A/duck/Alaska/702/1991{H8N2}        NMINDKIDDQ IEDLWAYNAE LLVLLENQKT LDEHDSNVKN LFDEVKRRLS ANAIDAGNGC
A/Hong Kong/1073/99{H9N2}           NMINNKIDDQ IQDVWAYNAE LLVLLENQKT IDMADSEMLN LYNKVKRALG SNAMEDGKGC
A/chicken/Germany/N/1949{H10N7}     GNVINWTKDS ITDIWTYNAE LLVAMENQHT IDMADSEMLN LYERVRKQLR QNAEEDGKGC
A/mallard/Netherlands/7/99{H11N2}   NQLSKHVDDS VVDIWSYNAQ LLVLLENEKT LDLHDSNVRN LHEKVRRMLK DNAKDEGNGC
A/duck/Alberta/60/1976{H12N5}       NMINSKIDDQ ITDIWAYNAE LLVLLENDKT LDEHDANVRN LHDRVRRVLR ENAIDTGDGC
A/gull/Maryland/704/1977{H13N6}     NMLADRIDDA VTDIWSYNAK LLVLLENDKT LDMHDANVKN LHEQVRRELK DNAIDEGNGC
A/mallard duck/Astrakhan/263/1982{H14N5} QDLEKYVEDT KIDLWSYNAE LLVALENQHT IDVTDSEMNK LHEQVRRQLR ENAEDQGNGC
A/duck/Australia/341/83{H15N8}      GNVINWTRDS LTEIWSYNAE LLVAMENQHT IDLADSEMNK LYERVRRQLR ENAEEDGTGC
A/shorebird/New Jersey/840/1986{H16N3} NMLADRVDDA VTDIWSYNAK LLVLIENDRT LDLHDANVKN LHEQVKRALK NNAIDEGDGC
```

FIGURE 1 (cont'd)

```
                                              ....|....| ....
                                                 485
A/Indonesia/5/2005{H5N1}                      FEFYHKCDNE CMES
A/Viet Nam/1203/2004{H5N1}                    FEFYHKCDNE CMES
A/California/04/2009{H1N1}                    FEFYHKCDNT CMES
A/New Caledonia/6/2008{H1N1}                  FEFYHKCNDE CMES
A/South Carolina/1/18{H1N1}                   FEFYHKCDDA CMES
A/Denver/57{H1N1}                             FEFYHKCDNE CMES
A/swine/Wisconsin/1/1968{H1N1}                FEFYHKCDDT CMES
A/Hong Kong/117/77{H1N1}                      FEFYHKCNNE CMES
A/Berkeley/1/68{H2N2}                         FEFYHKCDDE CMNS
A/Victoria/210/2009{H3N2}                     FKIYHKCDNA CIGS
A/Wisconsin/15/2009{H3N2}                     FKIYHKCDNA CIGS
A/chicken/Alabama/1/1975{H4N8}                FEIFHQCDNN CIES
A/mallard/Ohio/170/1999{H6N5}                 FEFWHKCDNE CIKS
A/Netherlands/219/03{H7N7}                    FEIFHKCDDD CMAS
A/duck/Alaska/702/1991{H8N2}                  FDILHKCDNE CMET
A/Hong Kong/1073/99{H9N2}                     FELYHKCDDQ CMET
A/chicken/Germany/N/1949{H10N7}               FEIYHTCDDS CMES
A/mallard/Netherlands/7/99{H11N2}             FTFYHKCDNE CIEK
A/duck/Alberta/60/1976{H12N5}                 FEILHKCDNN CMDT
A/gull/Maryland/704/1977{H13N6}               FELLHKCNDS CMET
A/mallard duck/Astrakhan/263/1982{H14N5}      FEIFHQCDNN CIES
A/duck/Australia/341/83{H15N8}                FEIFHRCDDQ CMES
A/shorebird/New Jersey/840/1986{H16N3}        FNLLHKCNDS CMET
```

FIGURE 3

FIGURE 3 (cont'd)
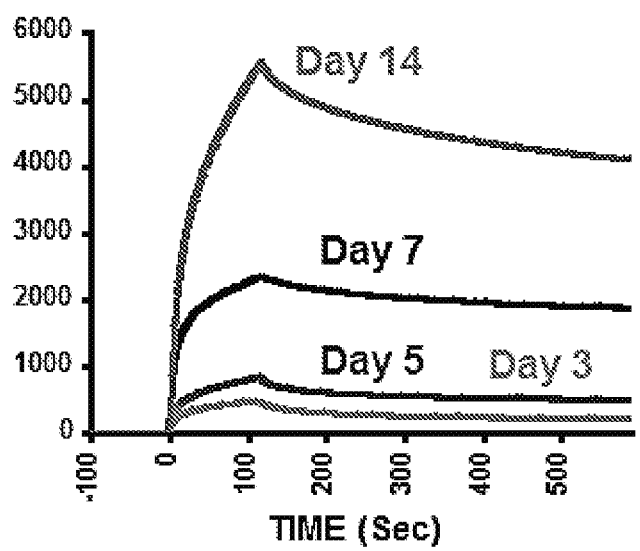
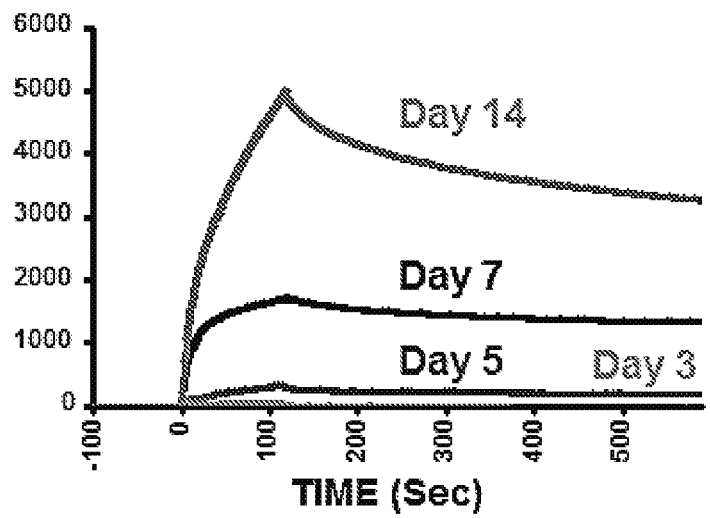

FIGURE 5

Adsorption of neutralization activity using HA proteins

Sheep anti-A/California/07/2009 -HA-sera (NIBSC)

| Peptides added | TITER* |
|---|---|
| No peptide | 6400 |
| HA 1-330 - FLOW-THROUGH | <40 |
| HA 1-480 - FLOW-THROUGH | <40 |
| GST-His - FLOW-THROUGH | 6400 |

Ferret anti-A/California/07/2009 -infected sera

| No peptide | 1280 |
|---|---|
| HA 1-330 - FLOW-THROUGH | <40 |
| HA 1-480 - FLOW-THROUGH | 80 |
| GST-His - FLOW-THROUGH | 1280 |

*End-point titers (mean of three replicates) using polyclonal rabbit sera in a microneutralization assay performed with A/California/07/2009 (X-179A)

FIGURE 6

Mean reciprocal neutralizing titers of rabbit anti-HA sera

| RABBIT | SERA | END-POINT TITERS* |
|---|---|---|
| H1N1-HA (1-330) | Pre Vaccine | <20 |
| | Post- 1 | 40 |
| | Post- 2 | 6,400 |
| | Post- 3 | 25,600 |
| H1N1-HA (1-480) | Pre Vaccine | <20 |
| | Post- 1 | <20 |
| | Post- 2 | 3,200 |
| | Post- 3 | 6,400 |

*End-point titers (mean of three replicates) using polyclonal rabbit sera in a microneutralization assay performed with A/California/07/2009 (X-179A)

*p=0.05, unpaired t-test

FIGURE 8
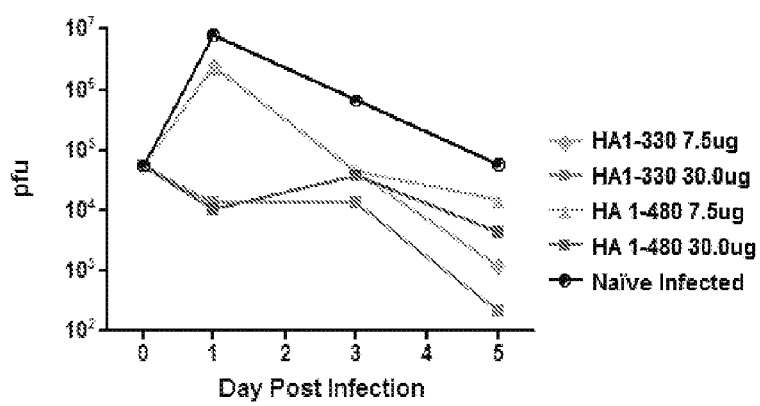
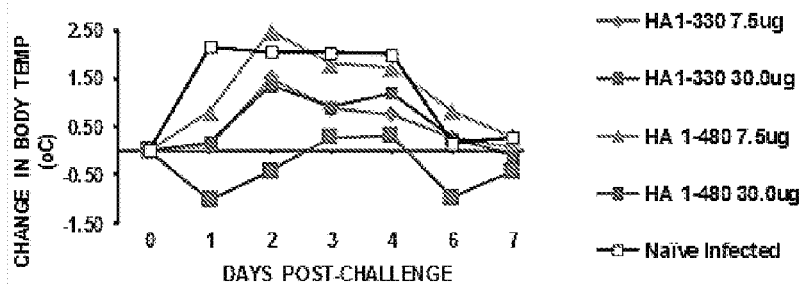
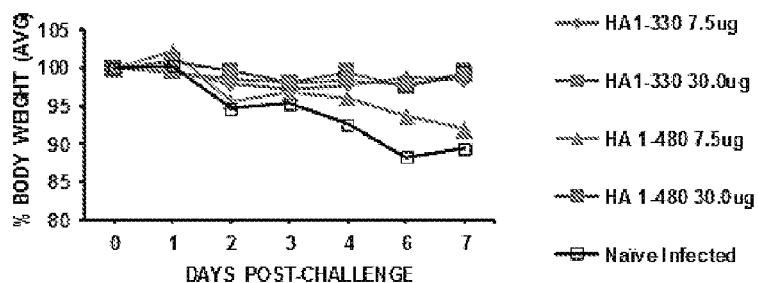

FIGURE 9 (cont'd)
C
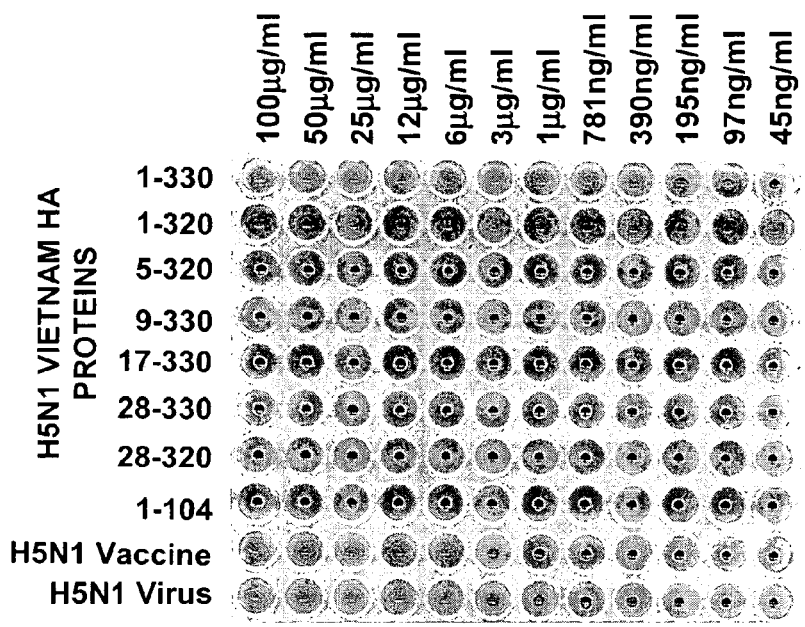
D
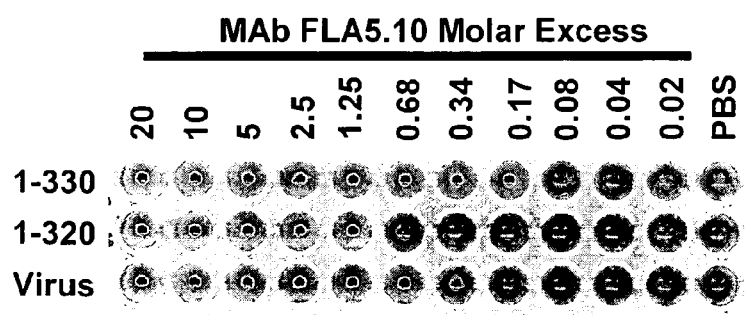

FIGURE 10

A    H5N1 VIETNAM HA 1-320

OLIGOMERS
112.2 ml 25 kDa 669 kDa 158 kDa 43 kDa

TRIMER
183 ml

MONOMER
212.8 ml

ABSORBANCE AT 280 nm (in mAU)

ELUTION VOLUME (in ml)

B    H5N1 VIETNAM HA 5-320

75 kDa   MONOMER 440 kDa 158 kDa 29 kDa

ABSORBANCE AT 280 nm (in mAU)

ELUTION VOLUME (in ml)

FIGURE 10 (cont'd)

C  H5N1 VIETNAM HA 28-320

D  H5N1 VIETNAM HA 1-104

Figure 10 (cont'd)
F
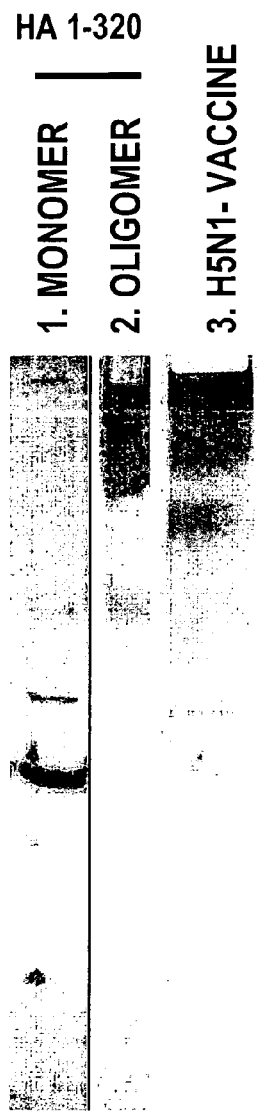
G
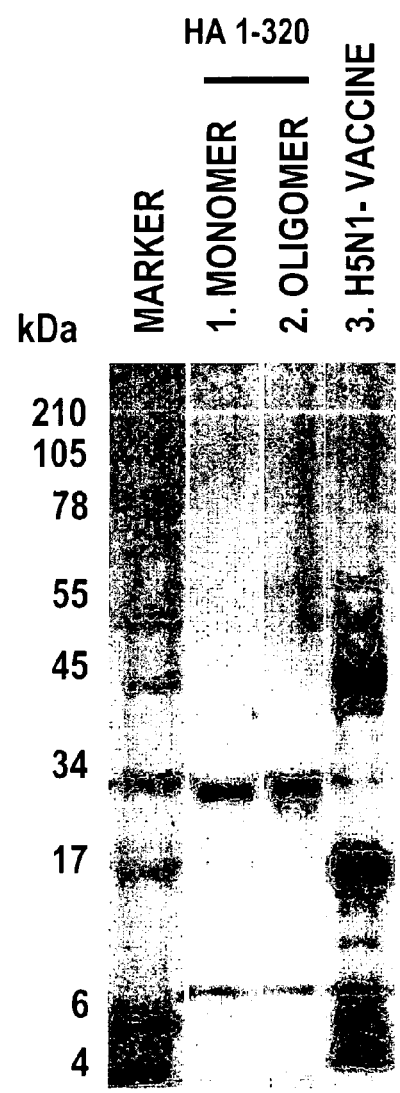

FIGURE 11
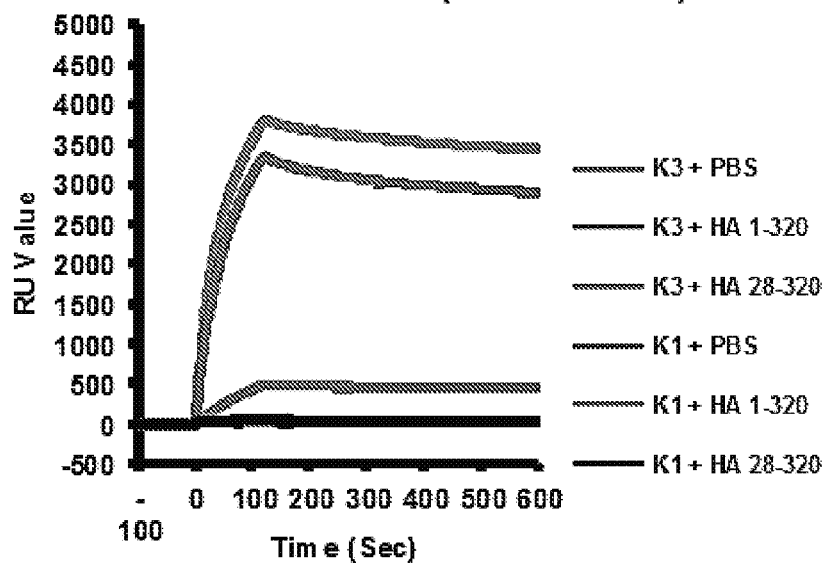
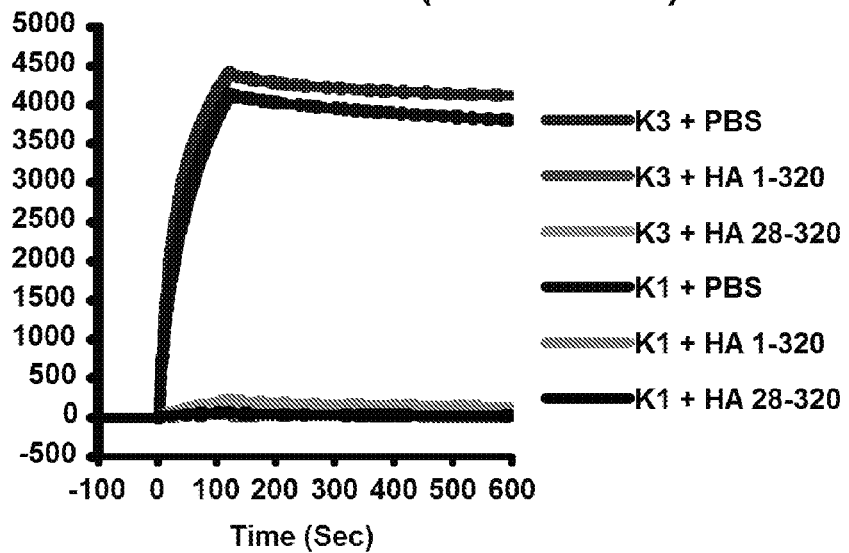

FIGURE 12
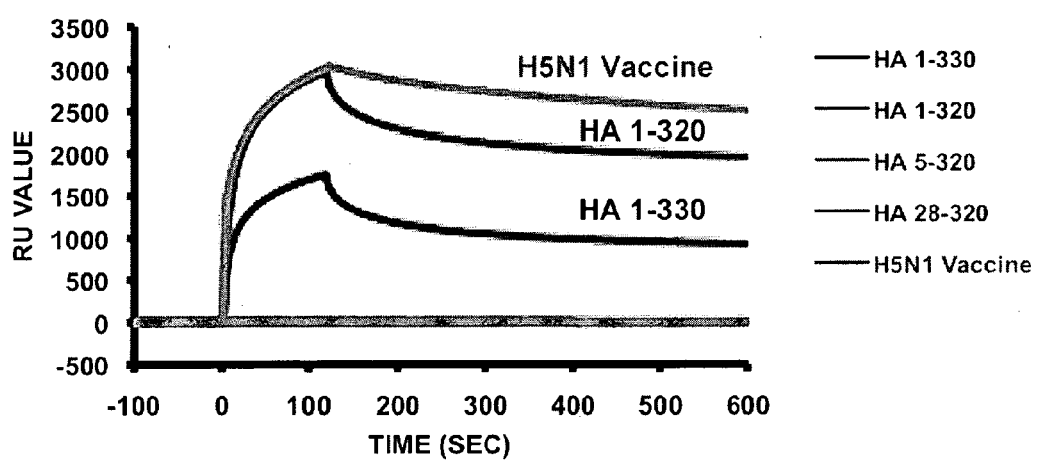
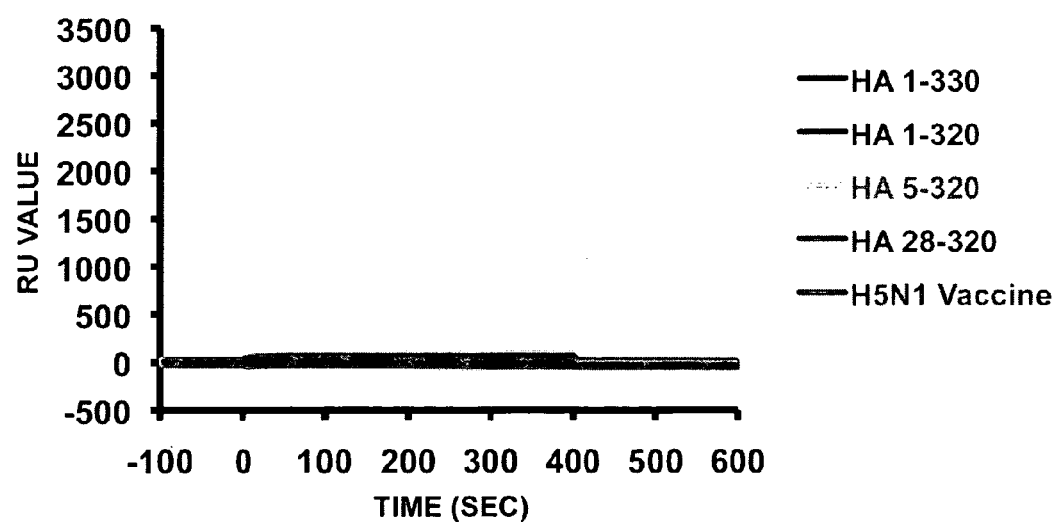

FIGURE 12 (cont'd)
C
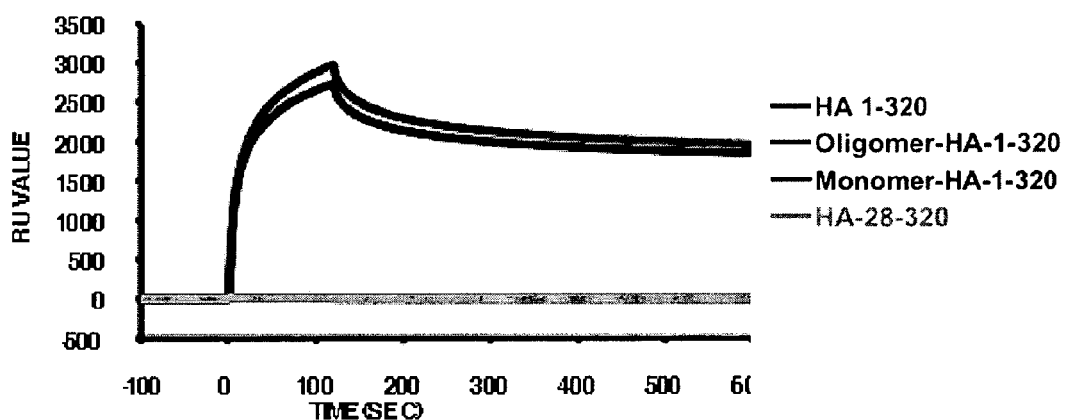
D
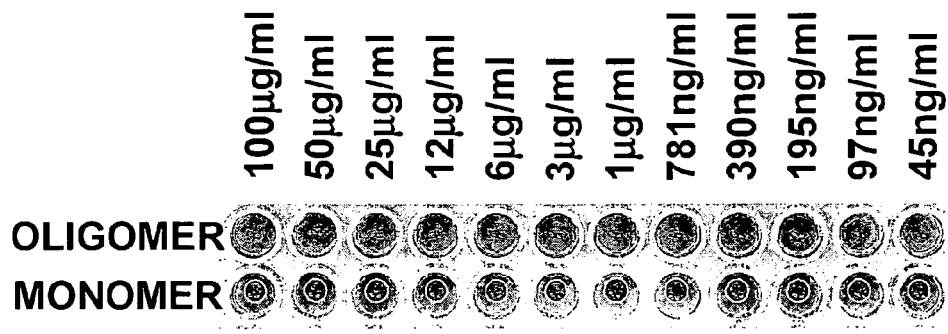

FIGURE 13

SUMMARY OF REACTIVITY OF

H5N1-HA DERIVATIVES IN VARIOUS ASSAYS

| H5N1 HA1 PROTEIN SEQ | PROPER FOLDING[1] (MAb-SPR) | PROTEIN SPECIES[2] (GEL FILTRATION) | RECEPTOR BINDING[3] (FETUIN) | HAEM-AGGLUTINATION[4] |
|---|---|---|---|---|
| HA 1-330 | YES | MONO, OLIGO | YES | 97 ng/ml |
| HA 1-320 | YES | MONO, OLIGO | YES | 4 ng/ml |
| HA 1-104 | ND | MONO, OLIGO | NO | NO |
| HA 5-320 | YES | MONO | NO | NO |
| HA 9-330 | YES | MONO | NO | NO |
| HA 17-330 | YES | MONO | NO | NO |
| HA 28-330 | YES | MONO | NO | NO |
| HA 28-320 | YES | MONO | NO | NO |
| HA 1-330-I3A-C4A-I5A | YES | MONO | NO | NO |
| HA 1-330-I3G-C4A-I5G | YES | MONO | NO | NO |
| H5N1 Vaccine | YES | OLIGO | YES | 6 ng/ml |

FIGURE 14

MEAN RECIPROCAL NEUTRALIZING TITERS OF POST-H5N1-HA1 RABBIT SERA

| SAMPLE | VIETNAM (CLADE 1) | TURKEY (CLADE 2.2) | ANHUI (CLADE 2.3.4) | INDONESIA (CLADE 2.1) |
|---|---|---|---|---|
| HA 28-320 | | | | |
| Pre-Bleed | <20 | <20 | <20 | <20 |
| Rb-Post 1st | <20 | <20 | <20 | <20 |
| Rb-Post 2nd | 80 | 40 | 160 | <20 |
| Rb-Post 3rd | 160 | 80 | 320 | <20 |
| Rb-Post 4th | 320 | 320 | 640 | 20 |
| HA 1-320 | | | | |
| Pre-Bleed | <20 | <20 | <20 | <20 |
| Rb-Post 1st | <20 | <20 | <20 | <20 |
| Rb-Post 2nd | 160 | 160 | 320 | 80 |
| Rb-Post 3rd | 5120 | 2560 | 5120 | 1280 |

FIGURE 15 (cont'd)
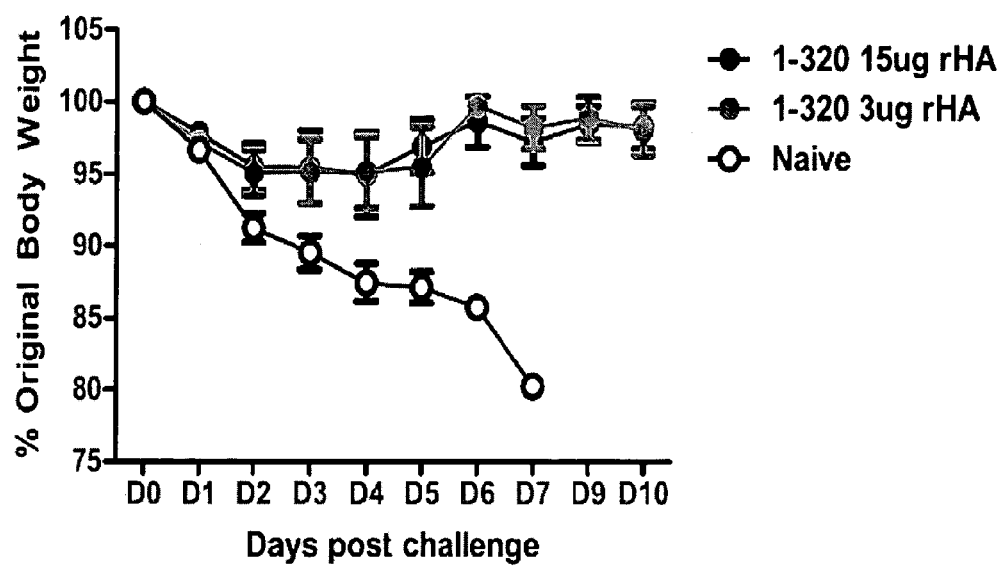
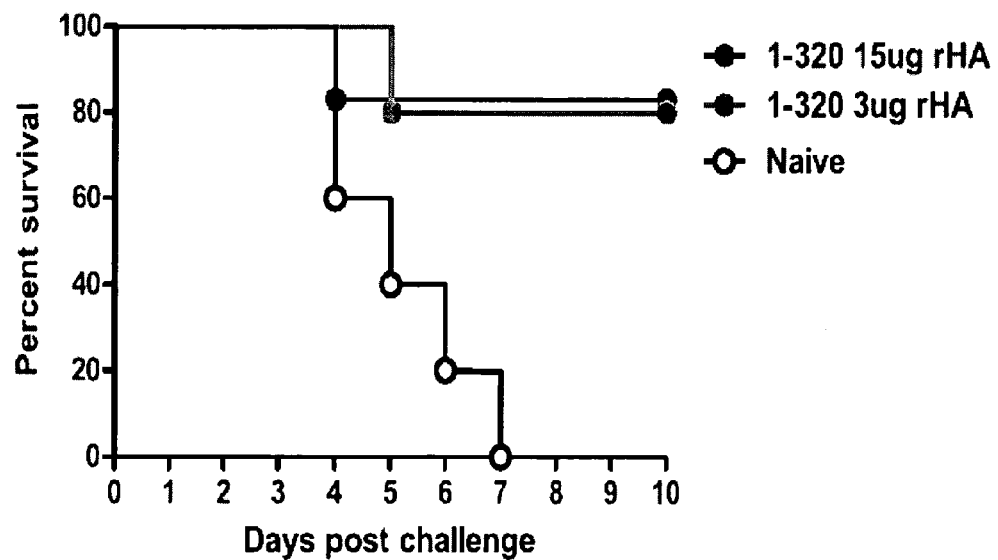

FIGURE 15 (cont'd)

H WhooperSwan Challenge 1.0x10e6pfu
Day 5 Nasal Titers

G WhooperSwan Challenge 1.0x10e6pfu
Day 3 Nasal Titers

FIGURE 16

H5N1 INDONESIA HA 1-320

H1N1 CALIFORNIA HA 1-320

FIGURE 16 (cont'd)
H3N2 VICTORIA HA 1-320

H3N2 WISCONSIN HA 1-320

H7N7 NETHERLANDS HA 1-320

FIGURE 17

| MEAN RECIPROCAL NEUTRALIZING TITERS OF POST-H5N1-Indonesia-HA1 RABBIT SERA | | |
|---|---|---|
| SAMPLE | VIETNAM (CLADE 1) | INDONESIA (CLADE 2.1) |
| H5N1-Indonesia HA 28-320 | | |
| Pre-Bleed | <20 | <20 |
| Rb-Post 1st | <20 | 40 |
| Rb-Post 2nd | <20 | 160 |
| Rb-Post 3rd | <20 | 640 |
| H5N1-Indonesia HA 1-320 | | |
| Pre-Bleed | <20 | <20 |
| Rb-Post 1st | <20 | 320 |
| Rb-Post 2nd | 80 | 2560 |
| Rb-Post 3rd | 320 | >10,240 |

FIGURE 19

| MEAN RECIPROCAL NEUTRALIZING TITERS OF POST-H5N1-HA1 RABBIT SERA | | | | |
|---|---|---|---|---|
| SAMPLE | VIETNAM (CLADE 1) | TURKEY (CLADE 2.2) | ANHUI (CLADE 2.3.4) | INDONESIA (CLADE 2.1) |
| HA 1-330 | | | | |
| Pre-Bleed | <20 | <20 | <20 | <20 |
| Rb-Post 1st | 40 | 20 | 40 | <20 |
| Rb-Post 2nd | 320 | 80 | 160 | <20 |
| Rb-Post 3rd | 640 | 640 | 640 | 160 |

Figure 20

Bacterial H5N1 HA1 | +1 HA1 (1-330) 330 |

↓ Animal immunization

(A) Anti-A/Vietnam/1203/2004 HA1 sera

| ANTIGEN | Undiluted | 1:1.5 | 1:2 | 1:4 | rA/Vietnam/1203/04 Lot# 50

(B) Anti-A/Indonesia/5/2005-HA1 sera

| ANTIGEN | Undiluted | 1:1.5 | 1:2 | 1:4 |

A/Indonesia/05/05 Lot # H5-Ag-0904

Figure 21

```
                                              1...|..8
A/Indonesia/5/2005(H5N1)                      DQICIGYH
A/Viet Nam/1203/2004(H5N1)                    DQICIGYH
A/California/04/2009(H1N1)                    DTLCIGYH
A/New Caledonia/6/2008(H1N1)                  DTICIGYH
A/South Carolina/1/18 (H1N1)                  DTICIGYH
A/Denver/57(H1N1)                             DTICIGYH
A/swine/Wisconsin/1/1968(H1N1)                DTLCIGYH
A/Hong Kong/117/77(H1N1)                      DTICIGYH
A/Berkeley/1/68 (H2N2)                        DQICIGYH
A/Victoria/210/2009(H3N2)                     ATLCLGHH
A/Wisconsin/15/2009(H3N2)                     ATLCLGHH
A/chicken/Alabama/1/1975(H4N8)                PVICLGHH
A/mallard/Ohio/170/1999(H6N5)                 DRICIGYH
A/Netherlands/219/03(H7N7)                    DKICLGHH
A/duck/Alaska/702/1991(H8N2)                  DRICIGYQ
A/Hong Kong/1073/99(H9N2)                     DKICIGHQ
A/chicken/Germany/N/1949(H10N7)               DRICLGHH
A/mallard/Netherlands/7/99(H11N2)             DEICIGYL
A/duck/Alberta/60/1976(H12N5)                 DKICIGYQ
A/gull/Maryland/704/1977(H13N6)               DRICVGYL
A/mallard duck/Astrakhan/263/1982(H14N5)      PIICLGHH
A/duck/Australia/341/83(H15N8)                DKICLGHH
A/shorebird/New Jersey/840/1986 (H16N3)       DKICIGYL
```

FIGURE 22

BACTERIAL HA1 FROM DIFFERENT INFLUENZA STRAINS CAUSE RBC AGGLUTINATION

INFLUENZA VIRUS RECOMBINANT PROTEINS

CROSS-REFERENCE TO RELATED PATENT APPLICATIONS

The present application is a U.S. National Phase of PCT/US2010/055166, filed Nov. 2, 2010, which claims benefit of U.S. Provisional Patent Application Nos. 61/257,785, filed Nov. 3, 2009, and, 61/325,216 filed Apr. 16, 2010, each of which are incorporated by reference for all purposes.

BACKGROUND OF THE INVENTION

Reference to a "Sequence Listing," a Table, or a Computer Program Listing Appendix Submitted as an ASCII Text File The Sequence Listing written in file-588-2.TXT, created on Dec. 4, 2014, 122,880 bytes, machine format IBM-PC, MS-Windows operating system, is hereby incorporated by reference in its entirety for all purposes.

Influenza is a contagious acute respiratory disease caused by infection of the upper respiratory and gastrointestinal tract by influenza virus. The viral genome is made up of several negative sense single stranded RNA molecules. Several proteins are encoded by the viral genome. Neuraminidase (NA) is a viral surface glycoprotein that cleaves terminal sialic acid residues from carbohydrate moieties on the surfaces of infected cells, promoting the release of progeny viruses. Hemagglutinin (HA) is one of the major viral surface glycoproteins and involved in the binding of the virus to sialic acids on the surface of susceptible cells (Uiprasertkul M, et al. Emerg. Infect. Dis. 11, 1036-1041 (2005)). Influenza HA is a trimer on virus particles. Influenza HA is synthesized as HA0 by virus post-infection in cells that is cleaved by cellular proteases at the basic cleavage site into HA1 and HA2 mature forms, which is required for proper function of this surface protein and for viral life cycle. The M2 protein is an ion channel protein. The HA, NA, and M2 protein are present in the viral envelope which is derived from the host cell plasma membrane. A ribonucleoprotein complex comprises an RNA segment associated with nucleoprotein (NP) and three polymerases, PA, PB1, and PB2. The M1 protein is associated with both ribonucleoprotien and the envelope.

Annual epidemics of influenza occur when the antigenic properties of the viral surface protein hemagglutinin (HA) and neuraminidase (NA) are altered. The mechanism of altered antigenicity is twofold: antigenic shift, caused by genetic rearrangement between human and animal viruses after double infection of host cells, which can cause a pandemic; and antigenic drift, caused by small changes in the HA and NA proteins on the virus surface, which can cause influenza epidemics.

Recently a new H1N1 strain, designated 2009 A(H1N1) or simply "A(H1N1)" was identified (commonly referred to in the lay press as "swine flu") and has become a pandemic. See, e.g., Garten et al. *Science*, 325:197-201 (2009).

BRIEF SUMMARY OF THE INVENTION

The present invention provides for isolated polypeptides, optionally produced in bacteria. In some embodiments, the polypeptide comprises:
a. at least a portion an influenza Hemagglutinin-1 (HA-1) domain, said portion comprising an influenza amino acid sequence corresponding to positions 1-259 of SEQ ID NOS:1, 2, 3, 4, 5, 6, or 7; and
b. lacks:
an Hemagglutinin-2 (HA-2) domain; and/or
an Hemagglutinin transmembrane domain.

In some embodiments, the polypeptide comprises a sequence of SEQ ID NO:1, 3, 4, 5, 6, or 7 or a sequence of FIG. 1 that corresponds to positions 1-259 of SEQ ID NO:2.

In some embodiments, the polypeptide binds to conformation sensitive influenza neutralizing antibodies. In some embodiments, the amino acid sequence is substantially identical (e.g., at least 70%, 80%, 90%, 95%, 98%, etc. identical) to positions 1-259 or 28-320 of SEQ ID NOS: 1, 2; 3, 4, 5, 6, or 7. In some embodiments, the portion comprises positions 1-259 or 28-320 of SEQ ID NOS: 1, 2, 3, 4, 5, 6, or 7. In some embodiments, the portion consists of positions 1-259 or 28-320 of SEQ ID NOS: 1, 2, 3, 4, 5, 6, or 7.

In some embodiments, the portion consists of an influenza amino acid sequence corresponding to positions 1-259 or 28-320 of SEQ ID NOS: 1, 2, 3, 4, 5, 6, or 7.

In some embodiments, the portion comprises an influenza amino acid sequence corresponding to positions 1-320 of SEQ ID NOS: 1, 2, 3, 4, 5, 6, or 7. In some embodiments, the amino acid sequence comprises a sequence of SEQ ID NO:1, 3, 4, 5, 6, or 7 or a sequence of FIG. 1 that corresponds to positions 1-320 of SEQ ID NO:2. In some embodiments, the amino acid sequence is substantially identical (e.g., at least 70%, 80%, 90%, 95%, 98%, etc. identical) to positions 1-320 of SEQ ID NOS:1, 2, 3, 4, 5, 6, or 7. In some embodiments, the portion comprises positions 1-320 of SEQ ID NOS:1, 2, 3, 4, 5, 6, or 7. In some embodiments, the portion consists of positions 1-320 of SEQ ID NOS:1, 2, 3, 4, 5, 6, or 7.

In some embodiments, the portion consists of an influenza amino acid sequence corresponding to positions 1-320 of SEQ ID NOS:1, 2, 3, 4, 5, 6, or 7.

In some embodiments, the portion comprises an influenza amino acid sequence corresponding to positions 1-330 of SEQ ID NOS:1, 3, 5, or 6. In some embodiments, the amino acid sequence is substantially identical (e.g., at least 70%, 80%, 90%, 95%, 98%, etc. identical) to positions 1-330 of SEQ ID NOS:1, 3, 5, or 6. In some embodiments, the portion comprises positions 1-330 of SEQ ID NOS:1, 3, 5, or 6. In some embodiments, the portion consists of positions 1-330 of SEQ ID NOS:1, 3, 5, or 6.

In some embodiments, the portion consists of an influenza amino acid sequence corresponding to positions 1-330 of SEQ ID NOS:1, 3, 5, or 6.

The present invention also provides for isolated polypeptides, optionally bacterially expressed, that bind to conformation-sensitive influenza-neutralizing antibodies, bind to red blood cells in hemagluttination assays, and/or bind to influenza receptors (including, e.g., sialic acid). In some embodiments, the polypeptide comprises:
a. at least a portion (including but not limited to, comprising a portion corresponding to positions 28-320, 1-259, 1-320 of SEQ ID NOS:1, 2, 3, 4, 5, 6, or 7) of an influenza Hemagglutinin-1 (HA-1) domain; and
b. lacks:
an Hemagglutinin-2 (HA-2) domain; and/or
an Hemagglutinin transmembrane domain.

In some embodiments, the influenza is selected from the group consisting of H5N1, H3N2, H1N1, H7N7 and H9N2. In some embodiments, the influenza is any of the influenza strains.

The present invention also provides physiological composition comprising any of the polypeptides described above or elsewhere herein, further comprising a physiological excipient.

In some embodiments, the composition is a vaccine. In some embodiments, the composition further comprises an adjuvant.

The present invention also provides methods of inducing an immune response against an influenza Hemagglutinin in an animal. In some embodiments, the method comprises administering an amount of the composition as described above or elsewhere herein to the animal sufficient to induce said immune response. In some embodiments, the animal is a human.

The present invention also provides methods of producing any of the polypeptides described above or elsewhere herein. In some embodiments, the method comprises expressing the polypeptide from polynucleotide (e.g., an RNA or DNA) encoding the polypeptide; and purifying the expressed polypeptide. In some embodiments, the expressing step is performed in vitro. In some embodiments, the expressing step is performed in a eukaryotic cell. In some embodiments, the expressing step is performed in a bacterium cell. In some embodiments, the bacterium is E. coli. The polypeptide can be cloned, expressed and purified in other prokaryotic or eukaryotic host cells including fungal, mammalian, insect cells etc. In some embodiments, the method further comprises formulating a vaccine comprising the purified polypeptide.

The present invention also provides for methods of detecting the presence or absence of an Hemagglutinin-specific antibody in a sample. In some embodiments, the method comprises performing an assay to determine binding of the antibody with any of the polypeptides described above or elsewhere herein; and detecting binding of the polypeptide to the antibody.

In some embodiments, the assay is a single radial immunodiffusion (SRID) assay.

The present invention also provides isolated nucleic acids encoding any of the polypeptides described above or elsewhere herein. In some embodiments, the codons of the nucleic acid are optimized for bacterial or eukaryotic expression.

The present invention also provides for expression cassettes comprising a promoter operably linked to a nucleic acid as described above or elsewhere herein. In some embodiments, the promoter is a bacterial or eukaryotic promoter.

Additional embodiments of the invention will be clear from the rest of this document.

DEFINITIONS

In the expression of recombinant genes, such as expression cassette or vector-expressed sequences or transgenes, one of skill will recognize that the coding polynucleotide sequence need not be identical to those described herein and may be "substantially identical" to a sequence, for example, to a particular sequence of an HA-1 domain polypeptide or portion thereof. As explained below, these variants are specifically covered by the term Hemagglutinin-1 (HA-1) domain. For example, in addition to the specific HA-1 sequences of A(H1N1) set forth herein, variants of such sequences such as those that occur in naturally-occurring influenza viruses are encompassed by the term "HA-1". These variations include partially or completely deglycosylated forms of the polypeptides, and the nucleic acids which encode these variations.

In the case where a polynucleotide sequence is transcribed and translated to produce a functional polypeptide, one of skill will recognize that because of codon degeneracy, a number of polynucleotide sequences can encode the same polypeptide. These variants are specifically covered by the above term. In addition, nucleic acids of the invention specifically include those sequences encoding polypeptides substantially identical (determined as described below) with the polypeptide sequences set forth herein.

A "fusion protein" refers to a composition comprising at least one polypeptide or peptide domain which is associated with a second amino acid sequence or domain. The second domain can be a polypeptide, peptide, polysaccharide, or the like. The "fusion" can be an association generated by a peptide bond, a chemical linking, a charge interaction (e.g., electrostatic attractions, such as salt bridges, H-bonding, etc.) or the like. If the polypeptides are recombinant, the "fusion protein" can be translated from a common message. Alternatively, the compositions of the domains can be linked by any chemical or electrostatic means following translation.

A "recombinant nucleic acid" comprises, or is encoded by, one or more nucleic acids that are derived from a nucleic acid which was artificially constructed. For example, the nucleic acid can comprise, or be encoded by, a cloned nucleic acid formed by joining heterologous nucleic acids as taught, e.g., in Berger and Kimmel, Guide to Molecular Cloning Techniques, Methods in Enzymology volume 152 Academic Press, Inc., San Diego, Calif. (Berger) and in Sambrook et al. (1989) Molecular Cloning—A Laboratory Manual (2nd ed.) Vol. 1-3 (Sambrook). Alternatively, the nucleic acid can be synthesized chemically. The term "recombinant" when used with reference to a cell indicates that the cell replicates or expresses a nucleic acid, or expresses a peptide or protein encoded by a nucleic acid whose origin is exogenous to the cell. Recombinant cells can express genes that are not found within the native (non-recombinant) form of the cell. Recombinant cells can also express genes found in the native form of the cell wherein the genes are re-introduced into the cell or a progenitor of the cell by artificial means.

An "expression cassette" refers to a nucleic acid construct, which when introduced into a host cell (e.g., a plant, mammalian, insect or bacterial cell), results in transcription and/or translation of a RNA or polypeptide (e.g., an HA-1 domain-containing polypeptide as described herein, respectively.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the sequence is complementary to all or a portion of a reference polynucleotide sequence.

Examples of algorithms that are suitable for determining percent sequence identity and sequence similarity are the BLAST and BLAST 2.0 algorithms, which are described in Altschul et al., Nuc. Acids Res. 25:3389-3402 (1977), and Altschul et al., J. Mol. Biol. 215:403-410 (1990), respectively. Software for performing BLAST analyses is publicly available on the Web through the National Center for Biotechnology Information (www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, *Proc. Natl. Acad. Sci. USA* 89:10915, (1989)) alignments (B) of 50, expectation (E) of 10, M=5, N=−4, and a comparison of both strands.

The BLAST algorithm also performs a statistical analysis of the similarity between two sequences (see, e.g., Karlin and Altschul, *Proc. Natl. Acad. Sci. USA* 90:5873-5787, (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 55% sequence identity to a designated reference sequence. Alternatively, percent identity can be any integer from 55% to 100%, for example, at least: 55%, 60%, 65%, 70%, 75%, 80%, 85%, 90%, 95%, or 99% compared to a reference sequence using the programs described herein; preferably BLAST using standard parameters, as described below. One of skill will recognize that the percent identity values above can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 50%. Percent identity of polypeptides can be any integer from 50% to 100%, for example, at least 50%, 55%, 60%, 65%, 70%, 75%, 80%, 85%, 90%, 95%, or 99%. The present invention provides for polypeptides comprising sequences substantially identical to those set forth herein.

In some embodiments, polypeptides that are "substantially similar" share sequences as noted above except that residue positions that are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Exemplary conservative amino acids substitution groups are: valine-leucine-isoleucine, phenylalanine-tyrosine, lysine-arginine, alanine-valine, aspartic acid-glutamic acid, and asparagine-glutamine.

As used herein, "isolated," when referring to a molecule or composition means that the molecule or composition is separated from at least one other compound, such as a protein, other nucleic acids (e.g., DNA, RNAs, etc.), or other contaminants with which it is associated in vivo or in its naturally occurring state.

BRIEF DESCRIPTION OF THE DRAWINGS

FIG. 1 provides an alignment of a selection of influenza Hemagglutinin HA-1-480 domain amino acid sequences (SEQ ID NOS:8-30).

FIG. 3. Development of neutralizing and anti-HA binding antibodies following wt H1N1 (A/California/7/2009) infection in ferrets. (A) Microneutralization of H1N1 A/California/2009 virus with post-H1N1-infected ferret samples. End-point titers (mean of three replicates) using post-infection sera from multiple ferrets at each time point in a microneutralization assay performed with A/California/07/2009 (X-179A). For day 21, sera of ten animals were pooled. Each dot in other time-points represents an individual H1N1 infected ferret. (B-D) Antibody kinetics following H1N1 challenge in ferrets. Steady-state equilibrium analysis of post-H1N1 infected ferret sera to mammalian H1N1 HA0 (Immune Technologies, NY) and properly folded bacterially expressed H1N1 HA1 (1-330) or H1N1 HA (1-480) fragment were measured using SPR. Ten-fold diluted individual post-infection sera from each time point, were injected simultaneously onto recombinant mammalian H1N1 HA0 in (B) and properly folded bacterially expressed H1N1 HA1 (1-330) in (C) or H1N1 HA (1-480) in (D), immobilized on a sensor chip through the free amine group, and onto a blank flow cell, free of peptide. Binding was recorded using ProteOn system surface plasmon resonance biosensor instrument (BioRad Labs, Hercules, Calif.).

FIG. 5 illustrates that properly folded bacterial H1N1 HA proteins adsorb neutralizing activity in post-H1N1 vaccination and post-H1N1 infection sera.

FIG. 6 illustrates immunization of rabbits with bacterially expressed H1N1 (1-330) and HA (1-480) elicit potent neutralizing antibodies FIG. 7. Hemagglutination-inhibition (HAI) titers in ferrets. HAI antibody in ferrets (n=4 per group) vaccinated with either 30 ug or 7.5 ug of influenza H1N1 rHA or mock vaccinated. Blood was collected at day 35 (post-dose 2). HAI responses were assessed against A/California/07/2009. Bars indicate geometric mean titer (GMT). The titer from each individual ferret is indicated by symbol. *p≤0.05 compared to mock.

FIG. 8. Viral loads and morbidity following A/California/07/2009 challenge in ferrets. (A) Viral replication of influenza A/California/07/2009 in nasal washes following intranasal challenge. Average pfu of virus from the nasal washes of each group (4 ferrets per group) on days 1, 3, and 5 post challenges. (B) Change in body temperature and (C) percent body weight.

FIG. 11 (A-B) H5-Viet-HA 1-320 induces oligomer specific antibodies. Five-fold diluted post-vaccination sera from Rabbit K1 (H5N1 HA 1-320), or Rabbit K3 (HA 28-320) were added to 0.5 mg of purified HA(1-320)-His$_6$ or to HA(28-320)-His$_6$ proteins (or PBS), and incubated for 1 hr at RT. Nickel-nitrilotriacetic acid (Ni-NTA) magnetic beads (200 µl) (Qiagen) were added for 20 min at RT on end-to-end shaker, to capture the His-tagged proteins and the antibodies bound to them, followed by magnetic separation. Supernatants containing the unbound antibodies were collected. The pre- and post-adsorbed sera were subjected to SPR analysis on purified oligomeric H5N1 HA (1-320) (A), or monomeric H5N1 HA (1-320) protein (B), immobilized on a sensor chip through the free amine group, and onto a blank flow cell, free of peptide. Binding was recorded using ProteOn system surface plasmon resonance biosensor instrument (BioRad Labs, Hercules, Calif.).

FIG. 12. Functional activities of H5N1 HA1 monomers and oligomers in receptor binding and hemagglutination. (A-B) Binding kinetics of purified H5N1 HA1 proteins and its mutants in a SPR based receptor binding assay. Steady-state equilibrium analysis of different H5N1-HA1 proteins to fetuin and its asialylated counterpart (Asialo-fetuin) was analyzed at 25° C. using a ProteOn surface plasmon resonance biosensor (BioRad Labs). Samples of purified bacterial H5N1-HA1 proteins and H5N1 vaccine (10 µg/ml) were injected simultaneously over a mock surface to which no protein was bound, followed by Fetuin (A) or Asialofetuin (B) immobilized on a sensor chip through the free amine group, and onto a blank flow cell, free of protein. Binding kinetics and data analysis were performed using ProteOn system surface plasmon resonance biosensor instrument (BioRad Labs, Hercules, Calif.). (C) monomers and oligomers of properly folded bacterially expressed H5N1 HA1 (1-320) were purified using a size-exclusion chromatography and subjected to SPR based fetuin binding assay. (D). human RBC hemagglutination with HA1 (1-320) monomeric and oligomeric forms isolated by size-exclusion chromatography.

FIG. 13 illustrates the H5N1-A/Vietnam/1203/2004 HA fragments that were produced in E. coli, and folded in-vitro, and that were tested in multiple binding and functional assays. All the proteins folded properly as studied using Circular Dichroism spectroscopy and binding to a panel of conformation dependent neutralizing monoclonal antibodies. Furthermore, the properly folded HA proteins that have intact N-terminal beta-sheet formed higher order quaternary structures, including trimers and oligomers. Trimeric HA-1 proteins that has complete receptor binding domain (1-320) bind strongly to the cognate receptor, Fetuin in SPR based assay. All receptor binding HA1 proteins also show specific haemagglutination with red blood cells. So the properly folded bacterially expressed proteins can form trimers and show functional activity in terms of receptor binding and haemagglutination without the requirement of post-translational modifications.

FIG. 14. H5N1-A/Vietnam/1203/2004 HA1 (1-320) elicits higher neutralizing titers than monomeric HA1 (28-320) in rabbits. (A) Animals were immunized with 100 μg proteins mixed with TiterMax adjuvant every three weeks. Sera were collected 8 days after each vaccination and analyzed in a microneutralization assay against various H5N1 virus strains. Representative of three experiments.

FIG. 17. Purified bacterial H5N1-HA1-330 protein from A/Indonesia/5/2005 elicits broadly cross-neutralizing antibodies compared to monomeric HA 28-320 in rabbits. The immunogenicity of bacterially expressed HA1 proteins was evaluated in rabbits following immunization with either HA1 (1-320) or HA1 (28-320). Microneutralization assay was used to evaluate both homologous and heterologous neutralizing capacity of post vaccination rabbit sera following each immunization (Table 2). After two immunizations, the monomeric HA1 (28-320) elicited modest titer of homologous (A/Indonesia/5/2005) neutralizing antibodies (1:160). The MN titer increased to 1:640 after the $3^{rd}$ dose. No cross neutralization of A/Vietnam/1203/2004 (clade 1) was observed (top panel). In contrast, rabbits immunized with HA1 (1-320) (containing 60% oligomers), showed a faster kinetics of immune response and broader cross-clade neutralization. A titer of 1:320 against A/Indonesia/5/2005 was measured after the first immunization, and increased dramatically to more than 1:10,240 after the third boost. Importantly, cross-clade neutralizing titers were also very significant including against A/Vietnam/1203/2004 (clade 1) (bottom panel)

FIG. 19. Mammalian expressed HA1 protein from A/Vietnam/1203/2004 elicit broadly cross-neutralizing antibodies in rabbits. The immunogenicity of mammalian expressed HA1 proteins was evaluated following immunization in rabbits. Microneutralization assay was used to evaluate both homologous and heterologous neutralizing capacity of post vaccination rabbit sera following each immunization. After two immunizations, the HA1 (1-330) (containing 30% oligomers) elicited modest titer of homologous (A/Vietnam/1203/2004) neutralizing antibodies (1:320). The MN titer increased to 1:640 after the $3^{rd}$ dose. Importantly, significant cross-clade neutralizing titers against A/Turkey (clade 2.2) and A/Anhui (clade 2.3.4), and A/Indonesia (clade 2.1) was observed.

FIG. 20. SRID analysis of H5N1 potency reference antigen using rabbit anti-HA1 antiserum prepared by immunizing rabbits with bacterially expressed HA1 of either A/Vietnam/1203/2004 (A) or A/Indonesia/5/05 (B). Dilutions of A/Vietnam/1203/04 (A) or A/Indonesia/5/05 (B) reference antigens were analyzed by SRID using the homologous reference antiserum. Precipitin rings were measured in two directions to the nearest 0.1 mm for determination of diameter.

FIG. 21. N-terminal amino acids Ile-Cys-Ile are required for HA1 oligomerization. Alignment of the N-terminal eight amino acids of the hemagglutinin (HA) protein from representative strains of Influenza A subtypes SEQ ID NOS:31, 31, 32, 33, 33, 33, 32, 33, 31, 34, 34-44, 37 and 45, respectively). Amino acid number +1 corresponds to mature HA1 (1-320) protein of H5N1 A/Vietnam/1203/2004 strain sequence described in this study (SEQ ID NO:2). Residues 2-7 constitute the N-terminal β-sheet. This domain can be mutagenized, substituted or domain swapped to generate HA proteins with higher oligomers with better functional activity including receptor binding, hemagglutination and more potent influenza vaccines. Alignment of the N-terminal amino acids of the HA protein from representative strains of 16 different influenza A hemagglutinin subtypes identified amino acids $I_3C_4I_5G_6$ (SEQ ID NO:46) as highly conserved. Since deletion of only four residues in the N-terminus of HA1 (HA 5-320) was sufficient to prevent RBC agglutination, we constructed two mutants of HA1 ($I_3C_4I_5$>$A_3A_4A_5$) and ($I_3C_4I_5$>$G_3A_4G_5$). These mutations did not affect protein folding as determined by binding to huMAb FLA5.10. However, both mutated proteins contained only monomers and did not agglutinate RBC (FIG. 13).

FIG. 22. HA1 Proteins from different Influenza strains form properly folded functional oligomers and cause hemagglutination. Agglutination of human RBCs by properly folded bacterial HA1 protein (HA 1-320) from different influenza strains including H5N1-A/Indonesia/5/2005, H3N2 A/Victoria/210/2009 & H7N7 A/Netherlands/219/03. Serial dilutions of purified HA1 proteins were mixed with washed RBC and hemagglutination was read after 30 min at RT.

DETAILED DESCRIPTION

I. Introduction

Figure 2:
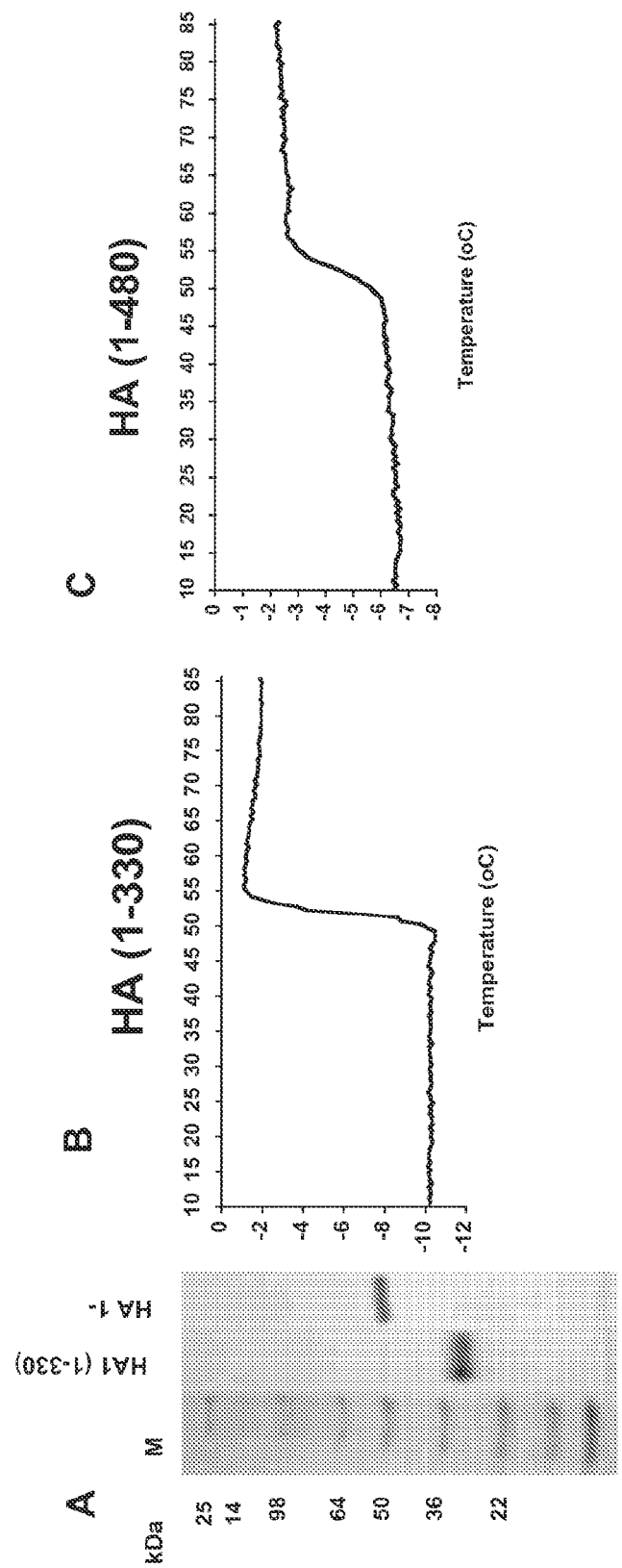
FIG. 2 Biochemical and functional characterization of bacterially expressed and purified H1N1 HA proteins. (A) Purified *E. coli* derived HA proteins were analyzed by SDS-PAGE. DNA encoding HA1 (1-330) and HA (1-480) from HA gene segment of A/California/07/2009 (H1N1) generated from egg-grown virus were used for cloning in a T7 promoter based expression vector (pSK) where the desired polypeptide can be expressed as fusion protein with $His_6$ tag at the C-terminus. The proteins were expressed, denatured and refolded under controlled redox conditions and purified using His-Trap fast flow chromatography to >90% purity. The purified proteins run at their corresponding molecular weight in reducing SDS-PAGE. (B-C) CD melt spectroscopy shows that both H1N1 HA1 (1-330) (B) and H1N1 HA (1-480) (C) are properly folded. Both H1N1 HA proteins, at a concentration of 0.5 mg/ml in 20 mM PBS, pH 7.2, were subjected to heating at 0.5° C./min increments. The protein unfolding kinetics was measured at 222 nm using a J-715 Circular Dichroism system (JASCO corp., Easton, Md.). (D-E) Superdex S-200 gel filtration chromatography of purified H1N1 HA proteins from *E. coli*. The panels present superimposed elution profiles of purified HA proteins (red line) overlaid with calibration standards (grey line). (D) The H1N1 HA (1-330) protein purified from bacterial cells existed as approximately 20% high-molecular-mass oligomer (>600 kDa), 45% trimer (~110 kDa) and 35% monomer (34 kDa) (red line). (E) H1N1 HA (1-480) is present only as a monomer (50 kDa). (F) Agglutination of human RBCs by properly folded bacterial H1N1 HA (1-330) protein. Serial dilutions of purified HA proteins or virus were mixed with washed RBC and incubated to analyze the receptor binding and cross-linking of human RBC. Virus H1N1×PR8 A/California/07/2009 (X-179A) was used as a control. Strong hemagglutination was observed for H1N1 HA (1-330) but not with H1N1 HA (1-480).
Figure 2:
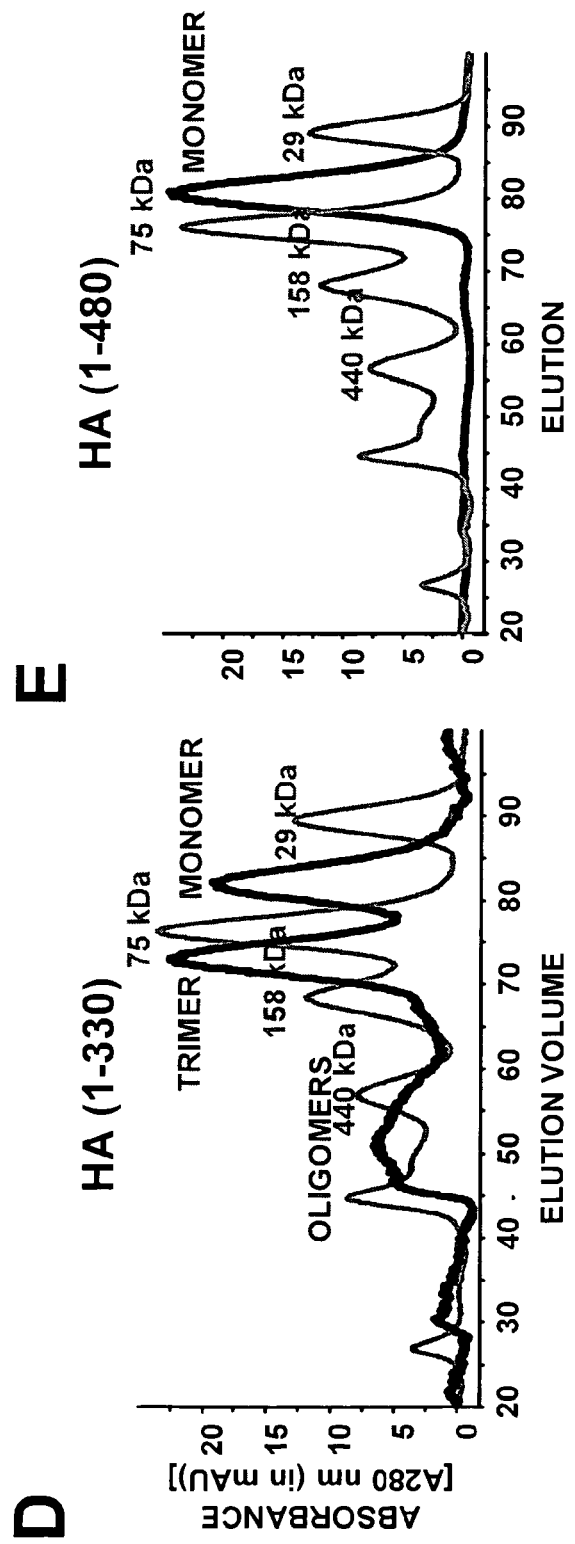
Figure 2:
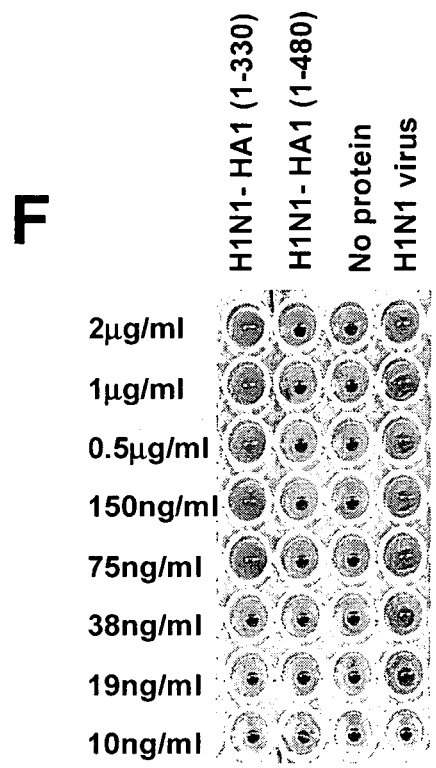

The present invention is based in part on the discovery that bacterial expression of the influenza Hemagglutinin-1 (HA-1) domain, without the Hemagglutinin-2 (HA-2) domain or transmembrane domain, results in a properly folded trimeric functional HA-1 domain. By generating a properly-folded trimeric functional Hemagglutinin domain in bacteria, the inventors have overcome the standard problem in influenza vaccine generation, namely the requirement to generate vaccine active ingredients in chicken eggs.

Bacterial expression of Hemagglutinin comprising both the HA-1 and HA-2 domains (but lacking the transmembrane domain) does not properly fold and thus is a poor candidate as a vaccine or for other uses where neutralizing epitopes need to be present. In contrast, the inventors have found that a truncated Hemagglutinin protein comprising only the HA-1 domain (or certain portions thereof) can be expressed in bacteria and fold properlyunder controlled redox refolding conditions. The inventors have shown proper folding and functionality of this HA-1 domain protein in:

Biophysical studies using CD spectra analysis (CD melt studies of the protein);

Gel filtration (Size exclusion) chromatography (showing trimers and higher order quaternary structures);

Haemagglutination functional assays; and

Receptor (i.e., Fetuin) binding.

Accordingly, the present invention provides for proteins comprising only the HA-1 domain (or certain portions thereof) of Hemagglutinin and lacking the remaining portions of influenza Hemagglutinin. Thus, in some embodiments, the polypeptides of the invention lack amino acids corresponding to positions 330-480 of SEQ ID NO:1. Notably, the inventors have made their discovery using the A(H1N1) A/California/07/2009 virus, known in the lay press as the "swine" flu. They have confirmed these findings in H5N1, H7N7, and H3N2 viruses as well. In view of the common conserves structure (though not primary sequence) of Hemagglutinin in influenza strains, it is believed that the invention is generally applicable to generation of properly folded HA-1 domains from any influenza virus.

II. Polypeptides of the Invention

The present invention provides for polypeptides that comprise an influenza virus HA-1 domain or certain portions thereof (e.g., portions capable of proper folding, following bacterial expression. to interact in a hemagluttination assay, including, e.g., amino acids corresponding to positions 28-320 or 1-320 from H1N1, H3N2, H5N1, or H7N7 HA-1), but lack the HA-2 and transmembrane domains (e.g., lacking amino acids corresponding to positions 331-480 of SEQ ID NO:1 or similar sequence from H5N1, H3N2 or other influenza virus). HA-1 domains can be identified from sequences of any influenza virus strain desired. The inventors have made their initial discovery using the A(H1N1) (aka, "swine flu") virus and therefore, in some embodiments, the polypeptides of the invention comprise the HA-1 domain or a portion thereof of an A(H1N1) virus but lacks an influenza HA-2 or transmembrane domain. However, the inventors believe that the finding that bacterially-expressed HA-1, in the absence of HA-2, folds properly is generally applicable to all influenza viruses. Indeed, as shown in Example 3, the inventors have shown that similar results occur when HA-from H5N1-Indonesia, H7N7-Netherlands and H3N2 (A/Victoria/210/2009 and A/Wisconsin/15/2009) are used in the absence of the Hemagglutinin-2 (HA-2) domain or transmembrane domain. Thus, although this application provides specific examples to the A(H1N1), H5N1, H7N7 and H3N2 sequences, it would be understood that, in some embodiments, similar manipulations can be made with non-A(H1N1), non-H5N1 influenza viruses, including but not limited to H3N2, H7N7, H2N2 and H9N2, seasonal H1N1 and other influenza.

The native influenza HA protein is expressed as "HA0," which is cleaved and in budded virus is composed of a trimer of HA1 and HA2 fragments. HA1 has the receptor binding domain and is attached to HA2 domain which has the fusion domain and is anchored into the viral membrane due to the presence of transmembrane domains.

In some embodiments, the HA-1 portion in the polypeptides of the invention comprises, or consists of, influenza Hemagglutinin protein corresponding to positions 1-259 in SEQ ID NOS:1, 2, 3, 4, 5, 6, or 7. The inventors have shown that a bacterially-expressed polypeptide having this fragment (positions 1-259) from Hemagglutinin of H5N1 properly folded as determined by the Circular Dichroism (CD) Melt analysis and also was reactive to conformation dependent neutralizing monoclonal antibodies in an SPR assay. In view of the other data described herein, it is believed that the corresponding fragment 1-259 from A(H1N1) (SEQ ID NO:1) will function similarly. In some embodiments, for example, the invention provides for polypeptides comprising, or consisting of, an amino acid sequence substantially (e.g., at least 70, 80, 90, 95%) identical to positions 1-259 in SEQ ID NOS:1, 2, 3, 4, 5, 6, or 7, but lacking an influenza HA-2 and transmembrane domain. It will be appreciated that those who study influenza virus routinely refer to positions based on the position of the amino acid in a reference strain. The reference sequence is generally SEQ ID NO:2. Thus, in some embodiments, the polypeptide lacks an influenza HA-2 and/or transmembrane domain and comprises a sequence of SEQ ID NO:1, 2, 3, 4, 5, 6, or 7 or a sequence of FIG. 1 that corresponds to positions 1-259 or 1-320 of SEQ ID NO:2. For example, position 320 of SEQ ID NO:1 corresponds to position 321 of SEQ ID NO: 3 or position 313 of SEQ ID NO: 5.

To determine which amino acid of a first protein "corresponds" to the position of an amino acid in a second protein, the amino acid sequences of the two proteins are optimally aligned (e.g., using a BLAST algorithm). This is particularly useful, for example, where two proteins have high homology but where one protein contains one or more insertions or deletions relative to the second protein. In such cases, for example, position 330 of a first protein may align with position 328 in a second protein when the two proteins are optimally aligned. Thus position 328 of the second protein "corresponds" to position 330 of the first protein.

The inventors have also found that HA amino acids corresponding to positions 1-320 or 1-330 of SEQ ID NO:1 or 1-320 of SEQ ID NOS:2, 3, 4, 5, 6, or 7 form a properly folded protein when expressed in bacteria in the absence of other carboxyl-terminal hemagglutinin sequences. Moreover they bind to the cognate receptor, Fetuin and also causes hemagglutination in hemagglutination assay. Accordingly, in some embodiments, the invention provides for polypeptides comprising an influenza Hemagglutinin sequence corresponding to positions 1-320 or 1-330 of SEQ ID NO:1 or 1-320 of SEQ ID NO:2. In some embodiments, for example, the invention provides for polypeptides comprising (or consisting of) an amino acid sequence substantially (e.g., at least 70, 80, 90, 95%) identical to positions 1-320 or 1-330 of SEQ ID NOS:1, 2, 3, 4, 5, 6, or 7.

A large number of other A(H1N1) and H5N1 HA sequences as well as other influenza Hemagglutinin protein sequences are known. For example, FIG. 1 sets forth an alignment of several influenza Hemagglutinin sequences.

The present invention provides for polypeptides comprising (or consisting of) sequences substantially similar to, or identical to, positions 1-320, or 1-330 of any of the sequences set forth in FIG. 1 or in SEQ ID NOS:1, 2, 3, 4, 5, 6, or 7, and further lacking an HA-2 and transmembrane domain of Hemagglutinin.

In some embodiments, the polypeptides of the invention are fusion proteins comprising the HA-1 domain, or a portion thereof capable of proper folding to interact in a hemagluttination assay, fused to a second polypeptide sequence other than HA-2. The second sequence can be linked at the amino or carboxyl terminus, or both, of the HA-1 domain or portion thereof. Heterologous fusion sequences encoding gD tags, c-Myc epitopes, poly-histidine tags, fluorescence proteins (e.g., GFP), or beta-galactosidase protein or glutathione S transferase which can be useful for detection or purification of the fusion protein expressed in or on a cell can be present.

The fusion proteins optionally includes additional features such as a flexible linker between the HA-1 domain and other heterologous amino acid sequences. The linkers can facilitate the independent folding of the HA-1 domain and other heterologous sequences. In some embodiments, flexible linkers are amino acid subsequences that are synthesized as part of a recombinant fusion protein. In one embodiment, the flexible linker is an amino acid subsequence comprising a proline such as $Gly_3$-Pro-$Gly_3$(SEQ OID NO:47). In other embodiments, a chemical linker is used to connect synthetically or recombinantly produced subsequences. Such flexible linkers are known to persons of skill in the art. For example, poly (ethylene glycol) linkers are available from Shearwater Polymers, Inc. Huntsville, Ala. Optionally, linkers have amide linkages, sulfhydryl linkages, or heterofunctional linkages.

In addition to flexible linkers, the fusion proteins optionally include polypeptide subsequences from proteins which are unrelated to Hemagglutinin, e.g., a sequence with affinity to a known antibody to facilitate affinity purification, detection, or the like. Such detection- and purification-facilitating domains include, but are not limited to, metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of cleavable linker sequences such as Factor Xa or enterokinase (Invitrogen, San Diego Calif.) between the purification domain and HA-1 domains may be useful to facilitate purification. One such expression vector provides for expression of a fusion protein comprising the sequence encoding the HA-1 domain-containing polypeptide of the invention, or a fusion protein thereof, and nucleic acid sequence encoding six histidine residues (SEQ ID NO:48) followed by thioredoxin and an enterokinase cleavage site (for example, see Williams (1995) *Biochemistry* 34:1787-1797). The histidine residues facilitate detection and purification while the enterokinase cleavage site provides a means for purifying the desired protein(s) from the remainder of the fusion protein. Technology pertaining to vectors encoding fusion proteins and application of fusion proteins are well described in the patent and scientific literature, see e.g., Kroll (1993) *DNA Cell. Biol.,* 12:441-53).

III. Methods of Making the Polypeptides of the Invention

Polynucleotides encoding influenza polypeptides, recombinant vectors, and host cells containing the recombinant vectors, as well as methods of making such vectors and host cells by recombinant methods are useful to produce the polypeptides as described herein for use in assays or immunogenic compositions.

The polynucleotides of the disclosure may be synthesized or prepared by techniques well known in the art. See, for example, Creighton, Proteins: Structures and Molecular Principles, W. H. Freeman & Co., New York, N.Y. (1983). Nucleotide sequences encoding the influenza polypeptides of the disclosure may be synthesized, and/or cloned, and expressed according to techniques well known to those of ordinary skill in the art. See, for example, Sambrook, et al., Molecular Cloning, A Laboratory Manual, Vols. 1-3, Cold Spring Harbor Press, Cold Spring Harbor, N.Y. (1989). In some embodiments, the polynucleotide sequences will be codon optimized for a particular recipient using standard methodologies. For example, a DNA construct encoding a HA-1-domain-comprising polypeptide can be codon optimized for expression in other hosts, e.g., bacteria, mammalian, fungal, insect cells etc.

The polynucleotides may be produced by standard recombinant methods known in the art, such as polymerase chain reaction (PCR) or reverse transcriptase PCR (Sambrook, et al., 1989, Molecular Cloning, A Laboratory Manual, Vols. 1-3, Cold Spring Harbor Press, Cold Spring Harbor, N.Y.), reverse engineering, or the DNA can be synthesized and optimized for expression in bacteria or eukaryotic cells. Primers can be prepared using the polynucleotide sequences that are available in publicly available databases. The polynucleotide constructs may be assembled from polymerase chain reaction cassettes sequentially cloned into a vector containing a selectable marker for propagation in a host. Such markers include but are not limited to dihydrofolate reductase or neomycin resistance for eukaryotic cell culture and tetracycline, ampicillin, or kanamycin resistance genes for culturing in *E. coli* and other bacteria.

Representative examples of appropriate hosts include, but are not limited to, bacterial cells such as *E. coli, Bacillus* sp., *Streptomyces* and *Salmonella* typherium, fungal cells such as yeast; insect cells such as *Drosophilia* S2 and *Spodoptera* Sf9, animal cells such as CHO, COS, and Bowes melanoma cells, and plant cells. Appropriate culture medium and conditions for the above-described host cells are known in the art. As noted herein, one significant benefit of the polypeptides of the present invention is that they fold properly when produced in bacteria.

Introduction of the recombinant vector into the host cell can be effected by injection, by calcium phosphate transfection, DEAE-dextran mediated transfection, cationic lipid-mediated transfection, electroporation, transduction, infection, or other methods. Such methods are described in standard laboratory manuals such as Sambrook, et al., 1989, Molecular Cloning, A Laboratory Manual, Vols. 1-3, Cold Spring Harbor Press, Cold Spring Harbor, N.Y. or Davis et al., 1986, Basic Methods in Molecular Biology. Commercial transfection reagents, such as Lipofectamine (Invitrogen, Carlsbad, Calif.), Effectene (Qiagen, Valencia, Calif.) and FuGENE 6™ (Roche Diagnostics, Indianapolis, Ind.), are also available.

The influenza polypeptide can be recovered and purified from recombinant cell cultures by methods known in the art, including ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography.

One of skill will appreciate that many conservative variations of the fusion proteins and nucleic acid that encode the polypeptides of the invention yield essentially identical products. For example, due to the degeneracy of the genetic code, "silent substitutions" (i.e., substitutions of a nucleic acid sequence, which do not result in an alteration in an encoded polypeptide) are an implied feature of every nucleic acid sequence that encodes an amino acid. Nucleic acid sequences can be optimized for expression in a particular host cell (e.g., bacteria, including but not limited to E. coli) used to produce the fusion protein. Similarly, "conservative amino acid substitutions," in one or a few amino acids in an amino acid sequence are substituted with different amino acids with highly similar properties are also readily identified as being highly similar to a particular amino acid sequence, or to a particular nucleic acid sequence which encodes an amino acid. Such conservatively substituted variations of any particular sequence are a feature of the present invention.

The immunogenic proteins of the invention may be purified from cells (including but not limited to bacterial cells). For a review of standard techniques see, e.g., Methods in Enzymology, "Guide to Protein Purification", M. Deutscher, ed. Vol. 182 (1990); Scopes, R. K., Protein Purification: Principles and Practice, 2nd ed., Springer Verlag, (1987). For instance, the polypeptides of the invention can be purified using affinity chromatography, SDS-PAGE, and the like. Methods for purifying desired proteins are well known in the art and are not presented in detail here.

Folding of a protein of the invention can be determined according to any method as discussed herein. In some embodiments, the expressed protein is tested in red blood cell hemagluttination assay. Examples of such assays include, for example, those described in Palmer et al. (1975, Advanced laboratory techniques for immunological diagnostic, U.S. Dept. Health. Ed. Welfare. P.H.S. Atlanta, Immunology Ser. No. 6, Procedural guide, part 2, hemagglutination inhibition test, pp. 25-62. Alternative testing of folding can include, e.g., testing the ability of the protein to bind to the influenza receptor (e.g., Fetuin); the ability to generate neutralizing antibodies in a host animal, and/or determination of the ability of the protein to assume appropriate quaternary structure.

IV. Nucleic Acids of the Invention

The present invention provides for nucleic acids that encode the polypeptides of the invention as well as for expression cassettes encoding the polypeptide and vectors comprising the expression cassettes.

The particular vector used to transport the genetic information into the cell is also not particularly critical. Any of the conventional vectors used for expression of recombinant proteins in prokaryotic and eukaryotic cells may be used.

V. Methods of Using the Polypeptides of the Invention

The present disclosure is also directed to uses and methods for immunizing an animal, including a human, other mammal, or bird, with the immunogenic compositions of the invention to inhibit, control, or prevent influenza infection.

In an embodiment, the method comprises administering to an animal an immunogenic effective amount of an immunogenic composition. An immunogenic effective amount is an amount of polynucleotide and/or polypeptide that induces an immune response to the encoded polypeptide when administered to a host, for example an animal. In an embodiment, the animal is a human, pig, horse, birds including domestic birds, or other animals, especially those used in animal models such as mouse, rat, ferret, or non-human primate. In an embodiment, the polynucleotides are incorporated into host cells in vivo and an immunogenic effective amount of the encoded polypeptide or fragment thereof is produced in vivo. The actual amount of the immunogenic composition may vary depending on the animal to be immunized, the route of administration and adjuvants.

Immunogenic dosages can be determined by those of skill in the art. The immune response may be indicated by T and/or B cell responses. Typically, the immune response is detected by the presence of antibodies that specifically bind to a particular polypeptide. The immune response can also be determined by detecting the presence of neutralizing antibodies or hemagglutinin inhibiting activity. Methods of detecting antibodies to polypeptides are known to those of skill in the art and include such assays as ELISA assays, western blot assays, virus and cell binding assays, functional and competition assays. Methods of detecting T cell responses include ELISPOT assays, ICS assays, and in-vitro and in-vivo cytotoxicity assays. The particular region of the polypeptide that is stimulating a T cell or antibody response can be mapped using whole genome phage display libraries as described herein.

In some embodiments, the immunogenic composition administered to an animal includes a polynucleotide and/or polypeptides or immunogenic fragments thereof and one or more of variable influenza components, one or more conserved influenza component, or a combination thereof. In an embodiment, the conserved influenza component is M1, NP, PA, PB1, PB2, NS1, NS2, an immunogenic fragment thereof or combination thereof. In some embodiments, the same polynucleotide does not encode an influenza component such as M1 and/or NP. In other embodiments, the polynucleotide does not encode an influenza component selected from the group consisting of M1, NP, PA, PB1, PB2, NS1, NS2, an immunogenic fragment thereof and combinations thereof.

In an embodiment, an animal is immunized with an immunogenic composition of the invention and then boosted one or more times with the immunogenic composition. In an embodiment, the animal is boosted about 2 to about 4 weeks after the initial administration of the immunogenic composition. If the animal is to be boosted more than once, there is about a 2 to 12 week interval between boosts. In an embodiment, the animal is boosted at about 12 weeks and about 36 weeks after the initial administration of the immunogenic composition. In another embodiment, the animal is a mouse and the mouse is boosted 3 times at 2 week intervals. In yet another embodiment, the animal is a primate and the primate is boosted 1 month and 6 months after the initial administration of the immunogenic composition. The dose used to boost the immune response can include one more cytokines, chemokines, or immunomodulators not present in the priming dose of the immunogenic composition.

Viral delivery vectors are known and commercially available. Examples of viral vectors include, but are not limited to, recombinant poxvirus including vaccinia virus, lentivirus, adenovirus, or viral like particles (VLPs). In an embodiment, the viral vector is adenovirus type 5. Examples of commercially available viral delivery vectors include, but are not limited to, VIRAPOWER™ lentivirus expression system, VIRAPOWER™ adenovirus expression system (Invitrogen, Carlsbad, Calif.), and ADENO—X adenovirus expression system (Clontech, Mountain View, Calif.).

Any mode of administration can be used in the methods of the inventions so long as the mode results in the delivery or expression of the desired peptide or protein, in the desired tissue, in an amount sufficient to generate an immune response to influenza (e.g., influenza A) and/or to generate a prophylactically or therapeutically effective immune response to influenza in an animal. The immunogenic compositions of the invention can be administered by intramuscular (i.m.), intra-nasally (i.n.), subcutaneous (s.c.), intradermally or intrapulmonary route in dosage unit formulations containing conventional non-toxic pharmaceutically acceptable carriers, adjuvants, or vehicles. Other suitable routes of administration include, but are not limited to intratracheal, transdermal, intraocular, intranasal, inhalation, intracavity, and intravenous (i.v.) administration. Transdermal delivery includes, but is not limited to intradermal, transdermal, and transmucosal administration. Intracavity administration includes, but is not limited to administration into oral or nasal cavities. The immunogenic compositions can be coated onto particles or nanofibers for delivery or formulated in liposomes.

Administration modes of the present invention include needle injection; catheter infusion; biolistic injectors; particle accelerators such as, for example, "gene guns" or pneumatic "needleless" injectors such as Med-E-Jet (Vahlsing et al., 1994, *J. Immunol. Methods*, 171:11-22), Pigjet (Schrijver et al., 1997, *Vaccine*, 15:1908-1916), Biojector (Davis et al., 1994, *Vaccine*, 12:1503-1509; Gramzinski et al., 1998, *Mol. Med.*, 4: 109-118), AdvantaJet (Linmayer et al., 1986, *Diabetes Care*, 9:294-297), or Medi-jector (Martins and Roedl, 1979, *Occup. Med.*, 21:821-824); gelfoam sponge depots; other commercially available depot materials such as, for example, hydrogels, osmotic pumps, oral or suppositorial solid (tablet or pill) pharmaceutical formulations, topical skin creams, and decanting, polynucleotide coated suture (Qin, Y., et al., 1999, *Life Sci.*, 65: 2193-2203), or topical applications during surgery. Certain modes of administration are intramuscular needle-based injection and pulmonary application via catheter infusion. Energy-assisted plasmid delivery (EAPD) methods may also be employed to administer the compositions of the invention. One such method involves the application of brief electrical pulses to injected tissues, a procedure commonly known as electroporation. See generally Mir et al., 1999, *Proc. Natl. Acad. Sci USA*, 96:4262-7; Hartikka et al., 2001, *Mol. Ther.*, 4:407-15; Mathiesen, 1999, *Gene Ther.*, 6:508-14; Rizzuto et al., 2000, *Hum. Gen. Ther.* 11:1891-900.

The present disclosure is also directed to kits for practicing the methods of the invention.

VI. Compositions

The polypeptides or nucleic acids of the present invention can be used in pharmaceutical and vaccine compositions that are useful for administration to animals, including but not limited to humans, to block transmission of a variety of infectious diseases. The compositions are suitable for single administrations or a series of administrations. When given as a series, inoculations subsequent to the initial administration are given to boost the immune response and are typically referred to as booster inoculations.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient and, in some embodiments, e.g., at a concentration of 25%-75%.

For aerosol administration, the polypeptides or nucleic acids are supplied in finely divided form along with a surfactant and propellant. The surfactant must, of course, be non-toxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery.

Compositions may include a carrier, excipient or adjuvant. Adjuvants include, for example, aluminum hydroxide, lipid A, killed bacteria, polysaccharide, mineral oil, Freund's incomplete adjuvant, Freund's complete adjuvant, aluminum phosphate, iron, zinc, a calcium salt, acylated tyrosine, an acylated sugar, a CpG oligonucleotide, a cationically derivatized polysaccharide, an anionically derivatized polysaccharide, a polyphosphazine, a biodegradable microsphere, TLR agonists, a monophosphoryl lipid A, MF59, oil in water emulsions AS03 and AS04, ISCOM, and quil A.

An embodiment provides an immunogenic composition comprising at least one naked DNA or a naked RNA encoding at least one polypeptide according to the disclosure. Naked DNA or RNA is DNA or RNA that does not have proteins or lipids associated with it.

Detection of Influenza Virus

The polypeptides of the invention are also useful for detecting influenza antibodies. Thus, for example, one can detect antibody response of an animal (e.g., a human) to a vaccine or to infection by a virus.

Essentially any assay can be used that detects the interaction of a polypeptide of the invention with an antibody or fragment thereof in a biological sample. Biological samples include blood, serum, tissue, urine samples, and biopsy samples. One or more of the polypeptides may be attached to a solid substrate such as a bead, ELISA plate, dipstick, or microarray.

The presence or absence of the antibody in the biological sample can be determined using methods known to those of skill in the art to detect the antigen antibody complex. Such methods include contacting the antibody antigen complex with a detectably labeled moiety that will bind to the antigen antibody complex and not to antibody or antigen alone. In some embodiments, the polypeptide of the invention and the biological sample are contacted in a single radial immunodiffusion (SRID) assay or a potency assay based on antigen alone or antigen-antibody complex. SRIDs are described in, e.g., Rodda, *J. Guth. Microbiol.* 14(5):479-482 (1981).

EXAMPLES

The following examples are offered to illustrate, but not to limit the claimed invention.

Example 1

We studied expression of truncated influenza Hemagglutinin protein in *E. coli* in an attempt to identify a fragment of Hemagglutinin that would fold properly following bacterial expression. Prior to this work, in spite of many years of study, those in the art have not successfully expressed properly folded trimeric functional Hemagglutinin protein in bacteria.

We initially prepared a set of Hemagglutinin truncations of H5N1 Hemagglutinin. Various HA fragments and their reactivity in binding, biophysical and functional assay is summarized in FIG. 13.

We subsequently successfully expressed in *E. coli* a truncated novel H1N1 ("swine" flu) Hemagglutinin fragment comprising only the HA-1 domain. This protein was designated H1N1-HA1 (1-330). Proteins were expressed in *E. coli* and were isolated as inclusion bodies. These inclusion bodies were partially purified by using detergents, and completely denatured using 6M guanidium. HCl and DTE. A variety of denaturing reagents can be used for denaturation of the proteins. The denatured proteins were then allowed to refold by dilution in renaturation buffer under redox condition. Then this renatured protein solution was dialyzed under controlled conditions to allow removal of denaturants, which in turn helped formation of disulfide bonds in the protein. Following dialysis, proteins were purified by affinity chromatography, ion-exchange and gel-filtration columns to obtain >90% pure proteins.

H1N1-HA1 (1-330) had proper folding and higher order quartnary structures as measured by gel filtration and reacted with red blood cells in a Hemagglutination assay. Plasmon resonance (SPR) analysis of antibody kinetics of H1N1-infected ferret response to bacterially expressed H1N1-HA1 (1-330) was determined. The kinetics of the response to H1N1-HA1 (1-330) was comparable to the ferret response to a mammalian-expressed (and thus properly folded) highlighting that properly folded bacterially expressed HA-1 can be used in lieu of mammalian expressed HA molecule for analysis of antibody responses following vaccination or infection and help develop tools for potency assays.

Figure 4:
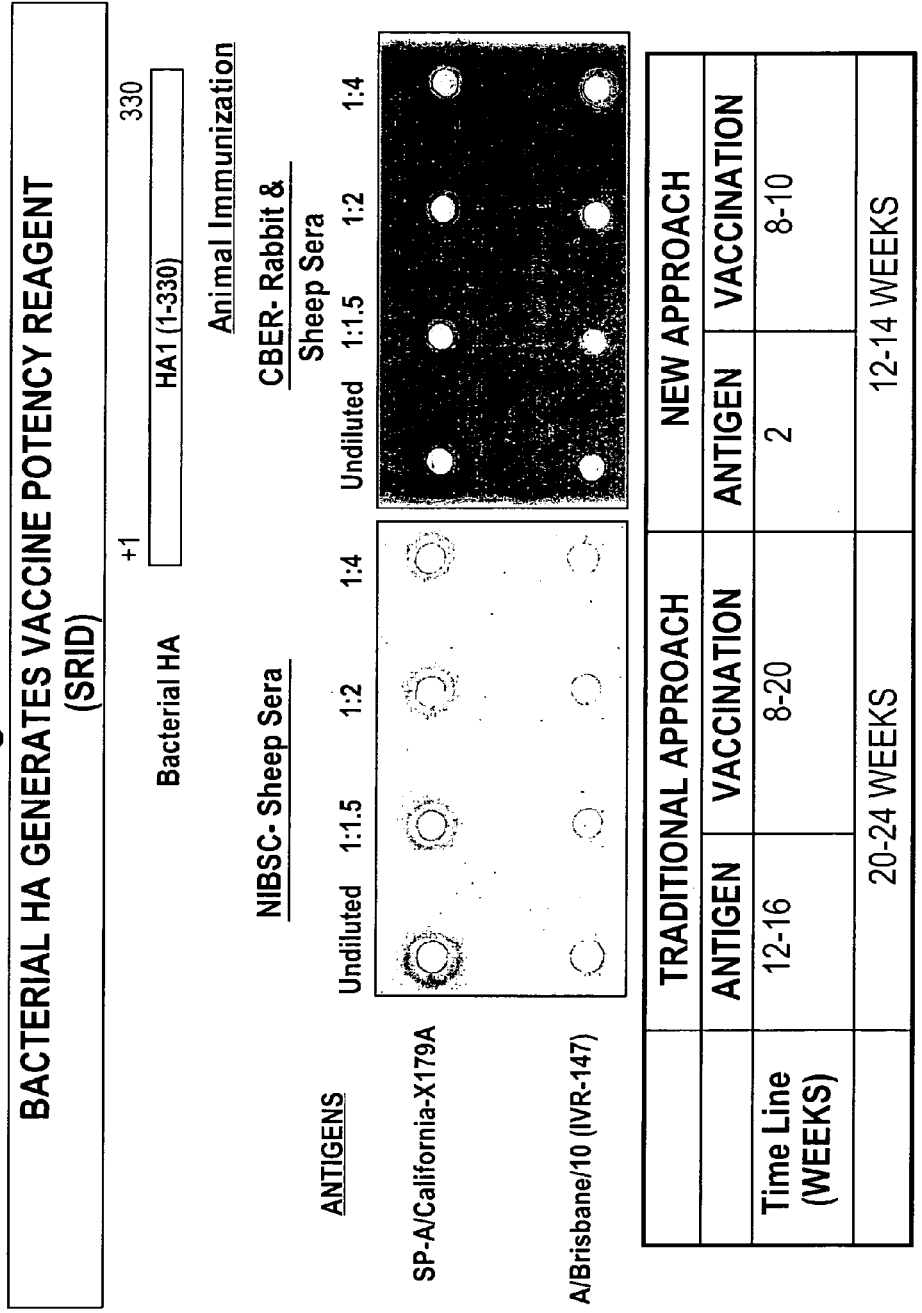
FIG. 4 illustrates that bacterial HA generates vaccine potency reagent (SRID).

We immunized these properly folded proteins in rabbits and sheep. The rabbit and sheep sera show a comparable specific activity in a Single Radioimmunodiffusion (SRID) assay as seen for the sheep sera immunized with HA protein isolated from H1N1 virus (FIG. 4). SRID assay is used every year for HA quantification, which is important for vaccine potency and lot release. Properly folded HA1 proteins produced in bacteria can generate reagents in shorter time and help develop these reagent for vaccine potency. Notably, HA-1 administered to rabbits or sheep, the animals generated strong neutralizing antibody response.

In summary, bacterial expression systems can be used for production of properly folded HA proteins. This was shown in our hands for each of:

H5N1—A/Vietnam/1203/2004
H5N1—A/Indonesia/5/2005
H1N1—A/California/06/2009
H3N2—A/Victoria/210/2009
H3N2—A/Wisconsin/15/2009
H7N7—A/Netherlands/219/03(H7N7)

H1N1-HA1 protein (lacking HA2 and transmembrane domain) expressed in *E. coli* and folded in-vitro forms trimers and oligomers, and binds specifically to its receptor and also causes hemagglutination. Bacterially expressed HA1 generated potent neutralizing antibodies against novel H1N1 virus and H5N1 viruses. Strong specific SRID was generated following bacterial HA1 immunization in rabbits and sheep.

We have thus developed an economical and rapid method for generation of properly folded trimeric receptor binding HA molecules in a prokaryotic system. This simple approach could help to develop better cross-protective vaccine candidates and reduce the timeline for generating vaccines by several months. The protein produced contains only an HA1 segment, which contains most Flu-neutralizing epitopes. The protein does not contain the HA2 sequence.

We anticipate that the HA1 proteins described herein will be useful, among other things:

As standards for quantification of HA in vaccine lots
To generate SRID sera (e.g., from sheep), helping to develop reagents to assess vaccine potency; and
Will result in reduced manufacturing timelines Example 2

In April 2009, the Centers for Disease Control and Prevention (CDC) announced the detection of a novel strain of influenza virus in humans. The novel virus derived its genes from viruses circulating in the pig population (Smith, G. J. et al., *Proc Natl Acad Sci USA* 106:11709-11712 (2009); Smith, G. J. et al., *Nature* 459:1122-1125 (2009); Shinde, V. et al., *N Engl J Med* 360:2616-2625 (2009)). Due to sustained human-to-human transmission of this novel virus throughout the world, on June 11th the World Health Organization (WHO) raised the worldwide pandemic alert level to Phase 6.

The most effective way to curtail pandemics is by mass vaccination (Smith, N. M. et al., *MMWR Recomm Rep* 55:1-42 (2006); Monto, A. *S Emerg Infect Dis* 12:55-60 (2006)). At the moment there are two types of licensed vaccines against seasonal influenza in the US: subunit (split) inactivated vaccines (IV) and live cold adapted attenuated influenza vaccine (LAIV) (Fiore, A. E. et al., *Curr Top Microbiol Immunol* 333:43-82 (2009)) (Cheng, X. et al., *PLoS ONE* 4:e4436 (2009); Ohmit, S. E. et al., *N Engl J Med* 355:2513-2522 (2006)). Both vaccines are grown in chicken eggs. The process of constructing a new vaccine strain based on newly circulating viruses is quite lengthy. It involves in vivo (in chicken eggs) or in vitro (in cell culture using reverse genetics techniques) reassortment between the internal genes of a donor virus such as A/PR/8/34 with the hemagglutinin (HA) and neuraminidase (NA) of the new influenza strain. The candidate vaccine strains must be further selected based on their high growth capability in eggs before they can be used for production of vaccines. Moreover, the manufacturing process is limited in scalability by the use of eggs and the amount of purified virus that can be produced. This process is used for the production of seasonal influenza vaccines every year, but it may pose a clear impediment to initiation of rapid mass vaccination against spreading pandemic influenza, as was evident for the 2009 H1N1 virus.

Recombinant HA based vaccines provide an alternative that could save several months of manufacturing time, since the HA gene of the newly circulating strain is available shortly after virus isolation. Expression of HA in insect cells and mammalian cells are under development and/or clinical trials (Treanor, J. J. et al., *J Infect Dis* 173:1467-1470 (1996); Treanor, J. J. et al., *J Infect Dis* 193:1223-1228 (2006); Wei, C. J. et al., *J Virol* 82:6200-6208 (2008)). The main challenge to the recombinant technology is to ensure that the HA products resemble the native virion-associated trimeric spike proteins and can elicit robust immune responses targeting protective conformational epitopes in the globular domain of HA.

In previous studies, we constructed H5N1 whole-genome-phage-display libraries (GFPDL) and used them to map the antibody responses following human infection with highly pathogenic H5N1 (A/Vietnam/1203/2004), as well as post-H5N1 vaccination sera. We identified large HA1 fragments, encompassing the receptor binding domain (RBD), that were bound by broadly neutralizing human monoclonal antibodies from H5N1 recovered individuals and by polyclonal convalescent sera. Several HA1 fragments were expressed and purified from *E. coli* inclusion bodies, and were shown to be properly folded and presented conformational epitopes (Khurana, S. et al., *PLoS Med* 6:e1000049 (2009)). The bacterially expressed HA1 proteins were also shown to absorb most of the neutralizing activity in post-H5N1 infection and post-H5N1 vaccination sera (Khurana, S. et al., *PLoS Med* 6:e1000049 (2009); Khurana, S. et al., *Science Translational Medicine* 2:15ra15-15ra15 (2010)). Based on these studies, it was predicted that HA1 fragments that contain most of the neutralizing antibody targets may generate protective immunity against emerging influenza strains.

Compared with insect or mammalian cells, expression of recombinant proteins in bacteria could present a viable alternative in terms of large scale vaccine production and a short time line suitable for rapid response in influenza pandemic. Several studies with bacterially expressed HA proteins based on the H5N1 avian influenza virus (AIV) were reported (Shen, S. et al., *J Med Virol* 80:1972-1983 (2008); Chiu, F. F. et al., *Biochem Biophys Res Commun* 383:27-31 (2009); Biesova, Z. et al., *Vaccine* 27:6234-6238 (2009)), and one clinical trial with a bacterially expressed fusion protein between the HA fragment and flagellin from *Salmonella typhimurium* type 2 (STF2), a TLR5 agonist is underway (Song, L. et al., *PLoS ONE* 3:e2257 (2008)). However, bacterially expressed HA proteins are not subjected to the post-translational modifications that takes place in eukaryotic cells, including step-wise glycosylation process important for proper folding of the HA protein, as well as trimerization and transport to the cell membrane (Copeland, C. S. et al., *J Cell Biol* 103:1179-1191 (1986); Ceriotti, A. et al., *J Cell Biol* 111:409-420 (1990); Roberts, P. C. et al., *J Virol* 67:3048-3060 (1993)). Indeed it was argued that in the absence of glycosylation, the newly synthesized HA proteins are not likely to fold properly or trimerize like native HA molecules, and may not present native conformational epitopes, which are important for generation of an effective protective immune response. Indeed the majority of the previous studies did not demonstrate proper folding and/or oligomerization of the HA proteins produced in prokaryotic systems (Shen, S. et al., *J Med Virol* 80:1972-1983 (2008); Chiu, F. F. et al., *Biochem Biophys Res Commun* 383:27-31 (2009); Biesova, Z. et al., *Vaccine* 27:6234-6238 (2009); Curtis-Fisk, J. et al., *Protein Expr Purif* 61:212-219 (2008); Xie, Q. M. et al., *Poult Sci* 88:1608-1615 (2009)). To address this concern, we established multiple assays to monitor the integrity of bacterially expressed HA proteins for proper folding, formation of trimers and oligomers, receptor binding, and agglutination of red blood cells (RBC). Here, we describe the properties of two novel H1N1 swine-like HA proteins, HA1 (1-330) and HA (1-480), expressed in *E. coli* and provide the first report of properly folded, trimeric, functional HA1 molecules capable of RBC agglutination reminiscent of native HA spike on influenza virion. Notably, vaccination of ferrets with both proteins resulted in reduced viral loads in nasal washes following challenge with novel H1N1 A/California/07/2009. However, HA1 (1-330) that causes hemagglutination is more easily produced, and shows better reduction of morbidity (body temperature elevation and weight loss) compared with HA (1-480) in vivo.

Results

Properties of Bacterially Expressed H1N1 HA1 (1-330) and HA (1-480)

DNA fragments encoding amino acid sequence 1-330 and 1-480 of HA from A/California/07/2009 were cloned as NotI-PacI inserts in the T7 promoter based expression vector with His6 (SEQ ID NO:48)tag at the C-terminus (Khurana, S. et al., *Science Translational Medicine* 2:15ra15-15ra15 (2010)). Both fragments of H1N1 HA expressed in *E. coli* Rosetta Gami cells (Novagen) localized to insoluble fraction (inclusion bodies). IBs were refolded in vitro under controlled redox conditions and purified by His Trap Fast flow chromatography. This process was previously shown to generate highly purified properly folded HA1 fragments from H5N1 (Khurana, S. et al., *Science Translational Medicine* 2:15ra15-15ra15 (2010)). The purified HA1 (1-330) and HA (1-480) proteins ran as a single band on SDS-PAGE with the anticipated MW of approximately 30 and 50 kDa, respectively (FIG. 2A)

To determine if the bacterially expressed (unglycosylated) HA1 (1-330) and HA (1-480) proteins are properly folded they were analyzed by CD spectroscopy. The change in ellipticity at 222 nm, which monitors unfolding of α-helix structures over a range of temperatures (CD melt), confirmed that both HA1 (1-330) and HA (1-480) behaved as properly folded proteins with a melting temperature around 52° C. (FIG. 2B-C).

We next determined if the bacterially expressed proteins oligomerized into higher molecular forms, using gel filtration chromatography on Superdex S200 XK 16/60 column (GE-Healthcare). Surprisingly, the HA1 (1-330) protein contained at least 50% of trimers and oligomers (FIG. 2D), while the larger HA (1-480) contained only monomers (FIG. 2E).

Bacterially Expressed HA (1-330) but not HA (1-480) can Agglutinate Human Red Blood Cells Hemagglutination of red blood cells (RBC) is a surrogate assay to measure the functionality of the influenza hemagglutinin. RBC agglutination requires properly folded HA with receptor binding domains that can bind to sialyloligosaccharide moieties on the RBC surface oligosaccharides. In addition, the presence of trimers and oligomers (mimicking the virion spikes) is required for the formation of RBC lattice (Matrosovich, M. et al., *Rev Med Virol* 13:85-97 (2003)). Therefore, it was important to determine the capacity of the HA1 (1-330) and HA (1-480) to agglutinate RBC. As seen in FIG. 2F, both H1N1 virions (positive control) and bacterially expressed H1N1 HA1 (1-330) protein very efficiently agglutinated human RBC. On the other hand, the HA (1-480) did not agglutinate human RBC. These difference in hemagglutination most likely reflected the presence of stable trimers and oligomers in the HA1 (1-330) but not HA (1-480) protein preparations.

Bacterially Expressed H1N1 HA (1-330) and HA (1-480) are Recognized by Sera From Ferrets Infected with A/California/07/2009

Figure 3:
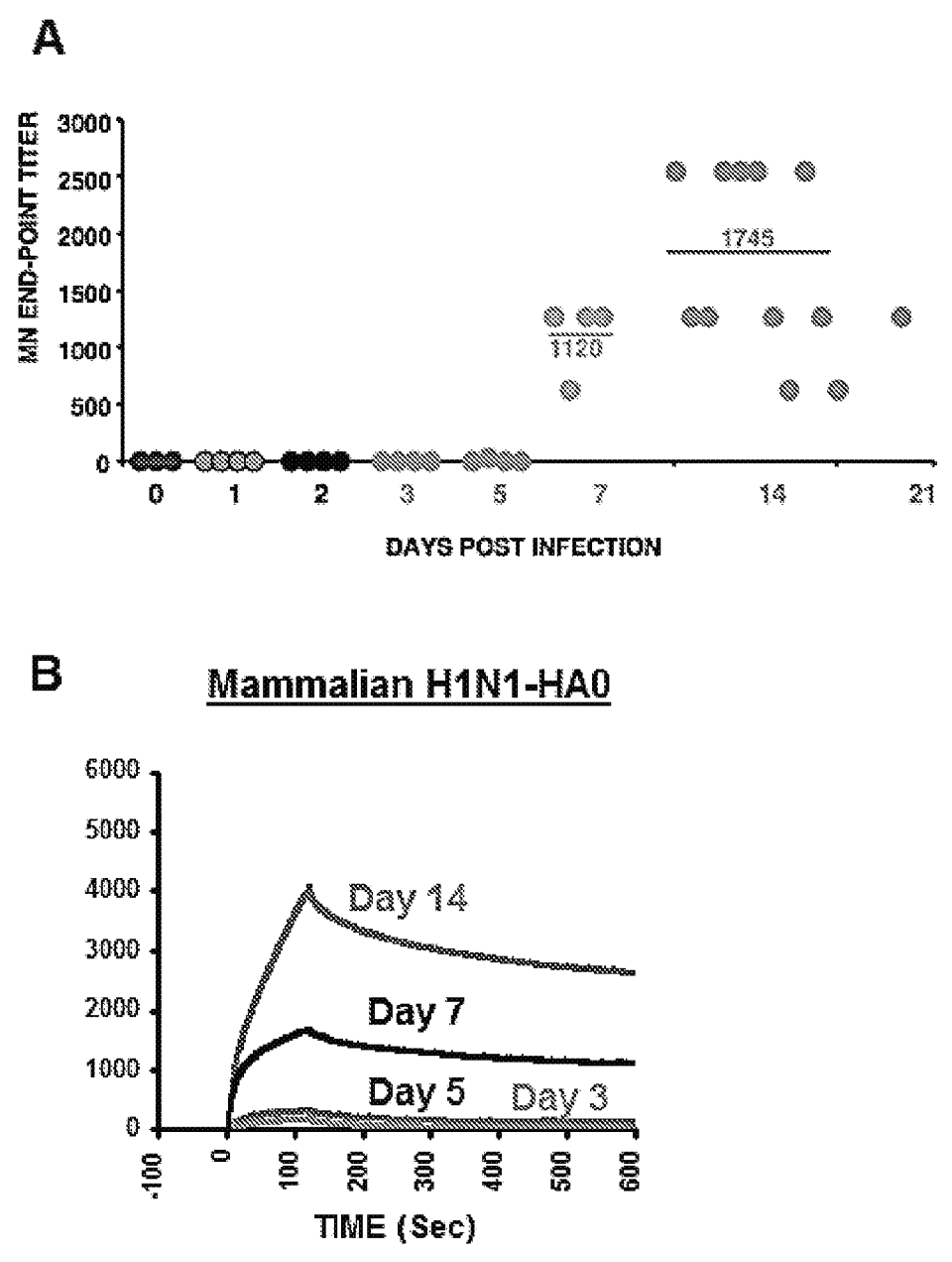

Ferrets are a good animal model for influenza virus pathogenesis. Following H1N1 infection, ferrets undergo transient loss of body weight, elevation in body temperature, and extensive viral replication in the upper and lower respiratory track on days 1-5, followed by viral clearance and recovery between Days 7-14 (Rowe et al. *Virology*, in press). Consecutive post-H1N1 infection ferret sera were evaluated for virus neutralizing antibody titers (FIG. 12A) and binding to recombinant H1N1 HA by surface plasmon resonance (SPR), using either mammalian cell expressed HA (Immune Technologies, NY) or the bacterially expressed H1N1 HA1 (1-330) and HA (1-480) proteins (FIG. 3B-D). MN titers were <20 during the first 5 days, followed by a rapid rise on days 7 and 14, and started to decline there after (FIG. 3A). In SPR, HA binding antibodies appeared as early as day 5 post infection and peaked on day 14. Importantly, binding of post-H1N1 infection ferret sera to whole HA from mammalian cells and to the bacterially expressed HA1 (1-330) and HA (1-480) proteins, demonstrated similar kinetics and binding avidity profiles (FIG. 3B-D), suggesting that the bacterially expressed proteins were antigenically similar to the mammalian cell derived HA. The increase in binding to properly folded H1N1-HA proteins correlated with an increase in the neutralization of A/California/07/2009 observed in sera from the post-H1N1 infected ferret sera on Day 7 and 14 when compared with sera from Day 5 post-H1N1 infection (FIG. 3A-D).

Properly Folded Bacterial H1N1 HA Proteins Adsorb Neutralizing Activity in Post-H1N1 Vaccination and Post-H1N1 Infection Sera The functional relevance of binding to properly folded bacterially expressed H1N1-HA protein was further confirmed in adsorption experiments (FIG. 5). Both HA1 (1-330) and HA (1-480) proteins adsorbed most of the neutralizing activity of post-H1N1 vaccinated immune sheep sera (NIBSC), reducing the MN titer from 1:6,400 to <1:40 (FIG.

5, top panel). Similar results were obtained with post-H1N1 infection ferret sera from day 21. The H1N1-HA1 (1-330) reduced the neutralizing activity of the convalescent sera from 1:1,280 to <1:40, while residual neutralizing activity (1:80) was observed after adsorption of sera with the larger H1N1-HA (1-480) (FIG. 5, lower panel). The combined data from the analytical and functional assays demonstrated that both bacterially expressed proteins are properly folded and express antigenically relevant conformational neutralizing epitopes.

Immunization of Rabbits with Bacterially Expressed H1N1 HA1 (1-330) and HA (1-480) Elicit Potent Neutralizing Antibodies To evaluate the immunogenicity of the bacterially expressed proteins, we immunized rabbits after mixing of HA1 (1-330) or HA (1-480) with Titermax adjuvant. The pre- and post vaccination sera were evaluated by microneutralization assay. Even after a single immunization with HA1 (1-330), rabbits had a MN titer of 1:40. After second and third immunizations high MN titers were measured (6,400 and 25,600, respectively) (FIG. 6, top panel). The HA (1-480) elicited H1N1 neutralizing antibodies only after the second and third boosts, and the peak MN titers (3,200 and 6,400, respectively) were lower compared with the HA1 (1-330) immunized rabbits (FIG. 6, lower panel).

Vaccination and Challenge Studies in Ferrets

Figure 7:
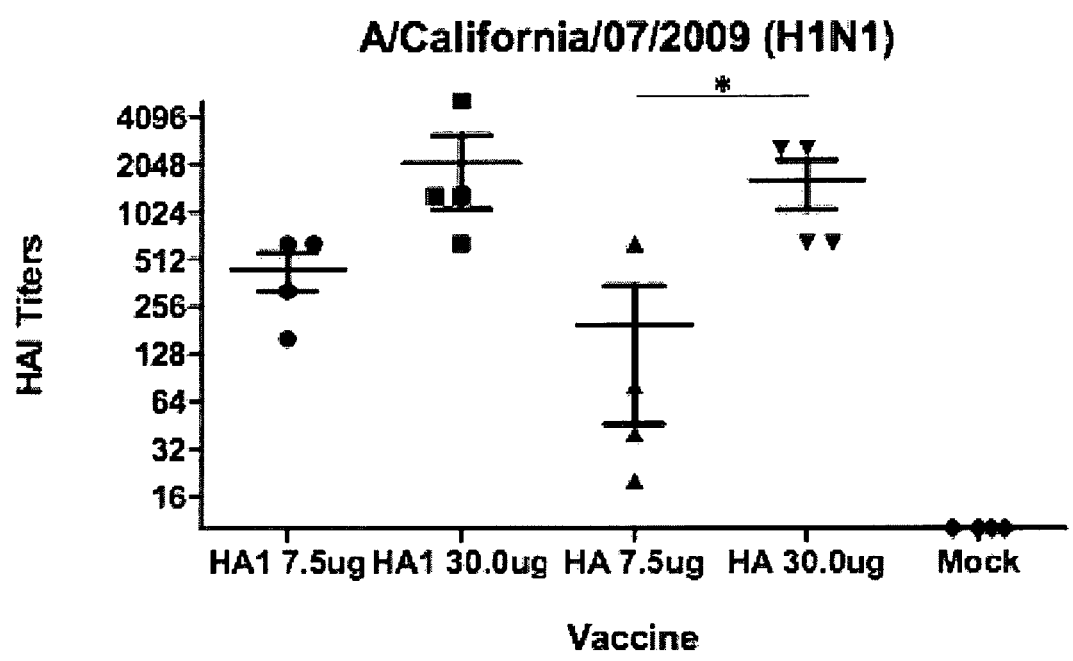

Female Fitch ferrets (n=4 in each group) were vaccinated intramuscularly in the quadricep muscle on day 0 and boosted on day 21 with either H1N1-HA1 (1-330) or HA (1-480) proteins at 7.5 and 30 µg dose combined with Titermax adjuvant. All animals were challenged with wild type A/California/07/2009 virus on day 35. Serum samples were collected after vaccinations and analyzed in HAI (FIG. 7). The 30 µg dose induced 2-4 fold higher titers compared with the 7.5 µg dose for both bacterially expressed proteins (FIG. 7). However, at the lower dose of 7.5 µg, the HA1 (1-330) consistently elicited higher HAI titers compared with the HA (1-480) at the same dose.

Following second vaccination, ferrets were challenged intranasally with $1 \times 10^6$ 50% egg infectious doses ($EID_{50}$) ($\sim 1 \times 10^{5.75}$ $TCID_{50}$/ml) of A/California/07/2009 virus in a volume of one milliliter. To determine viral loads in nasal washes, each ferret was administered each day post-challenge with 1.5 ml of 0.9% saline to each nare and washes were collected for virus titer determinations using the plaque assay.

In unvaccinated animals (naïve), viral loads in the nasal washes were highest on day 1, gradually declining on days 3 and 5 (FIG. 8A) and were back to baseline on day 7 as previously described (Rowe et al. *Virology* in press). Among the vaccinated animals, the high dose groups (30 µg), receiving either HA1 (1-330) or HA (1-480), reduced viral titers by >2 logs as early as day 1 post challenge. In the 7.5 µg vaccinated animals, virus replication on day 1 was observed, followed by a more rapid decline compared with the unvaccinated animals (FIG. 8A). Between day 3 and 5, a more rapid virus clearance was observed in the HA1 (1-330) vaccinated groups compared with the HA (1-480) vaccinated group or the naïve group (FIG. 8A).

In terms of morbidity, sustained elevation in body temperatures were measured in the naïve group post H1N1 virus challenge between days 1-4 (FIG. 8B). Inactivity and weight loss were also recorded up to day 7, followed by a slow recovery that did not reach normal weights by day 13 (termination) (FIG. 8C and data not shown). The HA1 (1-330) vaccinated animals that received 30 µg protein showed no temperature elevation and no weight loss (FIG. 8B-C). The 7.5 µg HA (1-330) vaccine dose also showed no weight loss and only a brief mild increase in body temperature on Day 2 (FIG. 8B-C). The HA (1-480) vaccinated animals at the 30 µg dose also showed no weight loss, and a transient elevation in body temperature on days 1-3 (not as high as in the naïve group). But the animals that received HA (1-480) at the lower dose (7.5 µg) showed an increase in body temperature similar to the naïve group and some weight loss on days 2-6 post challenge.

Together, these data demonstrate that properly folded bacterially expressed unglycosylated H1N1 HA proteins, elicited high neutralizing antibody titers in ferrets and significantly curtailed virus replication and morbidity following infection with the H1N1 A/California/07/2009 virus. Importantly, at the lower vaccine dose of 7.5 µg, the HA1 (1-330) that contained both trimers and oligomers protected ferrets from morbidity more efficiently than the HA (1-480), which only contain monomers. The clinical symptoms correlated with the observed HAI titers prior to challenge.

Discussion

The recent 2009-H1N1 swine-like virus influenza pandemic highlighted the need to rapidly produce enough vaccine doses for global vaccination brought to light the shortcomings of the traditional process of manufacturing influenza vaccines and the need to use alternative approaches for a more rapid generation of vaccine for global immunization in response to impending influenza pandemic. Bacterially expressed HA proteins can be manufactured rapidly and are amenable to mass production that can fulfill global vaccine needs. The main challenge to the prokaryotic production system is to ascertain proper refolding of expressed HA proteins representative of native HA spike structures on influenza virus. In addition to properly folded HA monomers, higher MW structures (i.e., trimers and oligomers) are important and likely to contribute to the optimal immunogenicity of the HA, since all influenza neutralizing antibodies are conformation dependent and some trimer specific antibodies have potent neutralizing activity (Wilson, I. A. *Annu Rev Immunol* 8:737-771 (1990)). In eggs and mammalian cells, post-translational glycosylation contribute to the proper folding, trimerization and transport of the newly synthesized HA molecules to the cell membrane (Copeland, C. S. et al., *J Cell Biol* 103:1179-1191 (1986)). However, in the case of recombinant HA proteins, trimerization is not always found even in eukaryotic cell substrates (Wei, C. J. et al., *J Virol* 82:6200-6208 (2008)).

The main findings in the current study are: (a) bacterially expressed H1N1 HA1 (1-330) and HA (1-480) can be purified as properly folded proteins as determined by CD spectroscopy, SPR analyses and adsorption of neutralizing activity from convalescent ferret sera; (b) the HA1 (1-330) contained >50% trimeric and oligomeric forms and could agglutinate human RBC, while the HA (1-480) was predominantly monomeric and did not agglutinate RBC; (c) both HA1 (1-330) and HA (1-480) induced H1N1-neutralizing antibodies in rabbits after two vaccinations; (d) in the ferret H1N1 challenge model, vaccination with bacterially expressed HA1 (1-330) and HA (1-480) at 30 µg HA induced high titers of neutralizing antibodies and protected animals from morbidity (elevated body temperature and weight loss) following challenge with novel H1N1 A/California/07/2009 virus; (e) following vaccination of ferrets with a lower dose (7.5 µg HA), the HA1 (1-330) vaccinated group demonstrated lower morbidity and more rapid virus clearance compared with the HA (1-480) vaccinated group.

This example extends our previous reports with the H5N1 highly pathogenic virus, in which we have used whole-genome-phage display libraries (GFPDL) to map the antibody responses following human infection or vaccination. We have identified large HA1 fragments, encompassing the receptor binding domain (RBD), that were bound by broadly neutralizing human monoclonal antibodies from H5N1 recovered individuals and by their polyclonal convalescent sera (Khurana, S. et al., *PLoS Med* 6:e1000049 (2009)). In a subsequent study, we found that following vaccination with inactivated H5N1 (A/Vietnam/1203/2004) influenza vaccine the immune sera from the MF59-adjuvanted vaccinated individuals bound with much higher avidity to bacterially expressed properly folded H5 HA1 proteins compared with unadjuvanted vaccine sera (Khurana, S. et al., *Science Translational Medicine* 2:15ra15-15ra15 (2010)). Importantly, the bacterially expressed HA1 proteins were also shown to absorb most of the neutralizing activity in post infection and post vaccination sera (Khurana, S. et al., *PLoS Med* 6:e1000049 (2009); Khurana, S. et al., *Science Translational Medicine* 2:15ra15-15ra15 (2010)). Based on these studies, it was predicted that bacterially-expressed HA1 fragments if properly folded, could be useful as vaccines against emerging influenza strains.

In the current example, we found that expression and purification of properly folded H1N1 HA1 (1-330) in bacterial system was more efficient and gave higher yield compared with the larger HA (1-480). While 50-60 mg of >90% purified HA (1-330) protein can be obtained from 1 liter of bacterial culture, the yield for HA (1-480) was only 10 mg/L. Interestingly, the HA (1-480) was less efficient in RBC agglutination and contained primarily monomers. The difference in adsorption of neutralizing antibodies in post-H1N1 infection sera for the two proteins, might be due to the presence of some trimer-specific neutralizing antibodies in the post-H1N1 infection ferret sera that can be only bound and adsorbed by the H1N1-HA (1-330), since it contains trimers while the H1N1-HA (1-480) is only present in a monomeric form. This is in agreement with previous reports on full length HA ectodomain proteins expressed in variety of cell substrates wherein peptide linkers were introduced to facilitate oligomerization (Wei, C. J. et al., *J Virol* 82:6200-6208 (2008)). Moreover, oligomerized product showed better vaccine efficacy than its monomeric counterpart (Wei, C. J. et al., *J Virol* 82:6200-6208 (2008)).

While both proteins were immunogenic in ferrets at the high dose of 30 µg, the HA1 (1-330) was more immunogenic and protected ferrets from H1N1 morbidity more efficiently at a lower dose (7.5 µg) compared with the HA (1-480) protein. In the case of mass vaccination, dose sparing is likely to be of great impact.

Our study describes the production of globular HA1 domain lacking the HA2 transmembrane protein, followed by controlled redox refolding conditions, resulting in a protein that contains functional trimers and oligomers without the addition of external trimerization sequences. The oligomeric HA1 mimics the trimeric globular heads on the virion spikes and generated neutralizing antibodies at the protective range (≥1:40) after a single vaccination of rabbits and ferrets. In our recent study on the antibody repertoires elicited by inactivated H5N1 vaccines, we noted that pre-vaccination sera contained antibodies against H5N1 HA1 segments that had 98% homology with the seasonal H1N1 HA2. Furthermore, following vaccination with the inactivated vaccine the majority of antibodies in the post second boost immune sera were against HA2 rather than HA1 epitopes. Since most of "protective" antigenic sites are mapped to the globular domain, surrounding the RBS, using an HA1 immunogen rather than intact HA (or inactivated subunit vaccine) is likely to generate a more focused antibody repertoires with enhanced kinetics. This approach could provide a simple and fast alternative for the current process of vaccine production in response to an impending pandemic.

In summary, in the face of an impending influenza pandemic, HA1 proteins derived from the newly spreading virus can be rapidly expressed in bacterial systems several months before the traditional approach using vaccine strains generated via either gene reassortment or reverse genetics, followed by adaptation to growth in eggs. With appropriate testing methods in place to monitor proper folding and biological activity (hemagglutination assay), this simple and efficient approach may provide an early vaccine for large scale production to fulfill global vaccine needs in a much shorter time frame. Moreover, bacterially produced HA vaccines may also be an alternative for humans with known egg allergies that cannot be immunized with traditional influenza vaccines produced in eggs.

Materials and Methods

Expression Vector and Cloning of H1N1-HA1 (1-330) and HA (1-480)

cDNA corresponding to the HA gene segment of A/California/07/2009 was generated from RNA isolated from egg-grown virus strain, and was used for cloning. pSK is a T7 promoter based expression vector where the desired polypeptide can be expressed as fusion protein with His6 tag at the C-terminus. DNA encoding HA1 (1-330) and HA (1-480) were cloned as NotI-PacI inserts in the pSK expression vector.

Protein Expression, Refolding and Purification

*E. coli* Rosetta Gami cells (Novagen) were used for expression of H1N1-HA1 (1-330) and HA (1-480). Following expression, inclusion bodies (IB) were isolated by cell lysis and multiple washing steps with 1% Triton X-100. The final IB pellets were resuspended in denaturation buffer containing 6M Guanidine Hydrochloride and dithioerythreitol (DTE) at final protein concentration of 10 mg/ml, and were centrifuged to remove residual debris. For refolding, supernatants were slowly diluted 100-fold in redox folding buffer (Khurana, S. et al., *Science Translational Medicine* 2:15ra15-15ra15 (2010)). The renaturation protein solution was dialyzed against 20 mM Tris HCl pH 8.0 to remove the denaturing agents. The dialysates were filtered through 0.45 µm filters, and were subjected to purification by HisTrap Fast flow chromatography. This process was previously shown to generate highly purified properly folded HA1 fragments from H5N1 (Khurana, S. et al., *Science Translational Medicine* 2:15ra15-15ra15 (2010)).

Circular Dichroism (CD)-Monitored Equilibrium Unfolding Experiment

To demonstrate that the bacterially expressed HA fragments are properly folded they were analyzed by CD spectroscopy (Khurana, S. et al., *Science Translational Medicine* 2:15ra15-15ra15 (2010)). For CD spectroscopy in solution, H1N1-HA proteins were dissolved in 20 mM PBS, pH 7.4, at 0.1 mg/ml. The change in elipticity at 222 nm (to follow unfolding of α-helices) during unfolding was monitored using a J-715 Circular Dichroism system (JASCO). The unfolding reaction was initiated by subjecting the protein in PBS to 10 C/min increments. The experiments were carried out in triplicate.

Gel Filtration Chromatography

H1N1-HA1 (1-330) and HA (1-480) at a concentration of 5 mg/ml were analyzed on Superdex S200 XK 16/60 column (GE-Healthcare) pre-equilibrated with PBS, and the protein elution monitored at 280 nm. Protein molecular weight marker standards (GE healthcare) were used for column calibration and generation of a standard curve to identify the molecular weights of the test protein sample.

Affinity Measurements by Surface Plasmon Resonance

Steady-state equilibrium binding of post-H1N1 vaccine or post-H1N1 infection sera was monitored at 25° C. using a ProteOn surface plasmon resonance biosensor (BioRad Labs). The H1N1-HA proteins were coupled to a GLC sensor chip (BioRad Labs) with amine coupling with 500 resonance units (RU) in the test flow cells. Ten-fold dilution of animal sera (60 μl) was injected at a flow rate of 30 μl/min (120-sec contact time). Flow was directed over a mock surface to which no protein was bound, followed by the HA protein coupled surface. Responses from the protein surface were corrected for the response from the mock surface and for responses from a separate, buffer only, injection. MAb 2D7 (anti-CCR5) and naïve ferret sera were used as a negative control antibody in the experiments. Binding kinetics for the animal sera and the data analysis were performed with Bio-Rad ProteON manager software (version 2.0.1). Similar binding studies were previously conducted with H5N1 HA1 proteins. Human monoclonal antibodies with conformation-dependent epitopes bound only to the properly folded HA proteins that were purified at pH 7.2 (identical to the current study) but not to unfolded HA1 proteins, purified at pH 3.0 (Khurana, S. et al., Science Translational Medicine 2:15ra15-15ra15 (2010)).

Hemagglutination Assay

Human erythrocytes were separated from whole blood (Lampire Biologicals). After isolation and washing, 30 μl of 1% human RBC suspension (vol/vol in 1% BSA-PBS) was added to 30 μl serial dilutions of HA protein or influenza virus in 1% BSA-PBS in a U-bottom 96-well plate (total volume, 60 μl). Agglutination was read after incubation for 30 min at room temperature.

Neutralizing Antibodies Adsorption with HA Proteins

Five-fold diluted post-H1N1 vaccination (NIBSC) sera or post-H1N1 infection ferret sera (500 μl) were added to 0.5 mg of purified HA-His$_6$ or to control GST-His$_6$ protein, and incubated for 1 hr at RT. Nickel-nitrilotriacetic acid (Ni-NTA) magnetic beads (200 μl) (Qiagen) were added for 20 min at RT on end-to-end shaker, to capture the His-tagged proteins and the antibodies bound to them, followed by magnetic separation. Supernatants containing the unbound antibodies were collected. The pre- and post-adsorbed sera were subjected to virus microneutralization assay.

Rabbit Immunization and Virus Neutralization Assays

White New Zealand rabbits were immunized three times intramuscularly at 21-day intervals with 100 μg of purified H1N1-HA1 (1-330) or HA 1-480) proteins with Titermax adjuvant (Titermax Inc). Virus-neutralizing titers of pre- and post vaccination rabbit sera were determined in a microneutralization assay based on the methods of the pandemic influenza reference laboratories of the Centers for Disease Control and Prevention (CDC). Low pathogenicity H1N1 virus, generated by reverse genetics, was obtained from CDC(X-179A). The experiments were conducted with three replicates for each serum sample and performed at least twice.

Vaccination of Ferrets and Blood Collection

Ferrets used in the study were tested to be sero-negative for circulating seasonal influenza A (H1N1 and H3N2) and influenza B viruses by HAI. Female Fitch ferrets (n=4 in each group) were vaccinated intramuscularly in the quadriceps muscle on day 0 and boosted on day 21 and then challenged with virus on day 35. Control animals (n=4) were mock vaccinated with phosphate buffered saline (PBS; pH 7.2). Each animal was vaccinated with one of two doses (30 μg or 7.5 μg) of recombinant HA in sterile 0.9% saline. Each vaccine was mixed with the adjuvant formulation, TiterMax (TiterMax USA, Inc, Norcross, Ga., US) at a 1:1 ratio. The volume for all intra-muscular vaccinations was 0.5 ml. The first and second vaccinations were given in the left and right hind legs, respectively. Blood was collected from anesthetized ferrets via the anterior vena cava. The collected blood was transferred to a tube containing a serum separator and clot activator and allowed to clot at room temperature. Tubes were centrifuged at 6000 rpm for 10 minutes; serum was separated, aliquoted and stored at −80±50 C. All procedures were in accordance with the National Research Council (NRC) Guidelines for the Care and Use of Laboratory Animals, the Animal Welfare Act, and the Centers for Disease Control (CDC)/National Institutes of Health (NIH) Bio-Safety Guidelines in Microbiological and Biomedical Laboratories and approved by the Institutional Animal Care and Use Committee (IACUC).

Infection and Monitoring of Ferret

Animal experiments with virus A/California/07/2009 were performed in the AALAC-accredited ABSL-3 enhanced facility. Animals were infected and monitored as previously described (Zitzow, L. A. et al., *J Virol* 76:4420-4429 (2002)), except using 5% isofluorane anesthesia. Briefly, ferrets were anesthetized with isofluorane and infected intranasally with $1\times10^6$ 50% egg infectious doses ($EID_{50}$) (~$1\times10^{5.75}$ $TCID_{50}$/ml) of A/California/07/2009 in a volume of one milliliter. Animals were monitored for temperature, weight loss, loss of activity, nasal discharge, sneezing and diarrhea daily following viral challenge. To determine viral load from nasal washes, 1.5 ml of 0.9% saline was administered to each nare and the wash was collected each day post-challenge of each ferret. Temperatures were measured through use of an implantable temperature transponder (BMDS, Sayre, Pa.) and were recorded at approximately the same time each day. Pre-infection values were averaged to obtain a baseline temperature for each ferret. Clinical signs of sneezing and nasal discharge, inappetence, dyspnea, neurological signs, respiratory distress, and level of activity were assessed daily. A scoring system was used to assess activity level where 0=alert and playful; 1=alert but playful only when stimulated; 2=alert but not playful when stimulated; 3=neither alert nor playful when stimulated. Based on the daily scores for each animal in a group, a relative inactivity index was calculated (Zitzow, L. A. et al., *J Virol* 76:4420-4429 (2002)).

Hemagglutinination Inhibition (HAI) Assay

RDE-treated ferret sera were serially diluted in v-bottom 96-well microtiter plates followed by the addition of 8 hemagglutination units (HAU) of influenza virus. Following an incubation of approximately 20 minutes, 0.5% suspension of turkey RBC (TRBC) in PBS (pH 7.2) were added and mixed by agitation. The TRBCs were allowed to settle for 30 minutes at room temperature and HAI titers were determined by the reciprocal value of the last dilution of sera which completely inhibited hemagglutination of TRBC. A negative titer was defined as 1:10.

Determination of Viral Loads

Viral loads in nasal washes were determined by the plaque assay. Briefly, MDCK cells plated in 6-well tissue culture plates were inoculated with 0.1 ml of virus-containing sample, serially diluted in Dulbecco's modified Eagle's medium (DMEM). Virus was adsorbed to cells for 1 h, with shaking every 15 min. Wells were overlaid with 1.6% w/v Bacto agar (DIFCO, BD Diagnostic Systems, Palo Alto, Calif., USA) mixed 1:1 with L-15 media (Cambrex, East Rutherford, N.J., USA) containing antibiotics and 0.6 mg/ml trypsin (Sigma, St. Louis, Mo., USA). Plates incubated for 5 days. Cells were fixed for 10 minutes using 70% v/v Ethanol and then overlaid with 1% w/v crystal violet. Cells were then washed with deionized water to visualize plaques. Plaques were counted and compared to uninfected cells.

Example 3

The recent global spread of swine-origin H1N1 highlighted the need for rapid development of effective vaccines against pandemic influenza viruses. Much of our recent knowledge was derived from studies with the highly pathogenic (HP) H5N1 avian influenza A viruses (AIV) (Treanor et al., *N Engl J Med* 354:1343-51 (2006)). The H5N1 viruses still cause severe human disease with >60% mortality, and may undergo adaptation for human-to-human transmission.

Antibodies specific to hemagglutinin (HA) are believed to be the best correlate of protection against influenza virus infection and are the primary end point used to evaluate vaccine immunogenicity. Production of hemagglutinin using recombinant technology could overcome the constraints of traditional influenza vaccine manufacturing that require several months for generation of vaccine viruses using reassortment/reverse genetics, and adaptation for high growth in eggs, suffer from bottlenecks at every step, expensive and dependent on supply of eggs. But using recombinant HA proteins pose several challenges; in addition to proper folding of the HA monomers, trimer formation is an important property of native HA spike proteins required for cell attachment (Wilson et al., *Nature* 289:366-73 (1981)) and for optimal immunogenicity (Wei et al., *J Virol* 82:6200-8 (2008)). On virions, the trimeric HA complex is stabilized by three 76 Å long helices that form a triple coiled-coil structure and consists of residues primarily from the HA2 region. Stability studies indicated that the HA2 tails contribute 28.4 kcal mol$^{-1}$ and the HA1 heads only 5.3 kcal mol$^{-1}$ to the stability of the trimers (Eisenberg, D., and A. D. McLachlan, *Nature* 319: 199-203 (1986); Wilson, I. A., and N. J. Cox, *Annu Rev Immunol* 8:737-71 (1990)). The expression of recombinant HA ectodomain in mammalian cells required the addition of multimerization "foldon" at the C-terminus in order to produce stable oligomeric structures (Wei et al., *J Virol* 82:6200-8 (2008)). Therefore, the prediction was that HA1 globular head (without HA2) will not form stable trimers (Bizebard et al., *Nature* 376:92-4 (1995)).

Expression of recombinant HA proteins in bacterial systems could provide a rapid and economical approach for early response to impending influenza pandemic. However, it was not clear that unglycosylated proteins will present antigenically relevant epitopes. Most of the influenza protective antigenic sites are conformation dependent and map primarily to HA1 globular head (Stevens et al., *Science* 303:1866-70 (2004); Wiley et al., *Nature* 289:373-8 (1981)). Previously, we used H5N1 whole-genome-phage-display libraries (GF-PDL) to map the antibody repertoires following human infection with highly pathogenic (HP) H5N1 (A/Vietnam/1203/2004) AIV as well as in post-H5N1 vaccination sera (Khurana et al., *Sci Transl Med* 2:15ra5; Khurana et al., *PLoS Med* 6:e1000049 (2009)). We identified large HA1 fragments, encompassing the receptor binding domain (RBD) that bound broadly neutralizing human monoclonal antibodies and polyclonal sera from H5N1 recovered individuals. Furthermore, in a recent study in our laboratory, bacterially expressed globular HA1 (1-330) and HA ectodomain (1-480) derived from novel H1N1 A/California/04/2009 were compared. Both proteins were properly folded. However, only the HA1 globular head (1-330) formed oligomers and agglutinated human RBC. In contrast, the HA ectodomain (1-480) contained only monomers and did not agglutinate RBC (Khurana et al., *PLoS One* 5:e11548).

To better understand the phenomenon of oligomerization of HA1 globular domain in absence of HA2 sequence, we expressed a series of H5N1-derivd HA1 proteins with N- and C-terminal deletions and point mutations, and correlated their ability to form oligomers with functional hemagglutinin properties including receptor binding and agglutination of red blood cells (RBC). Furthermore to figure out the importance of oligomerization for immunogenicity and cross-protection, these HA1 proteins were used in rabbit vaccination and in the ferret influenza HP H5N1 virus challenge model. Our findings show that functional oligomeric rHA1 proteins can be produced efficiently in bacterial systems and provide rapid response for development of effective vaccines against emerging influenza strains.

Materials and Methods:
Expression Vector and Cloning of H5N1-HA1 Derivatives cDNA corresponding to the HA gene segment of H5N1-A/Vietnam/1203/2004 was generated from RNA isolated from egg-grown virus strain, and were used for cloning. pSK is a T7 promoter based expression vector where the desired polypeptide can be expressed as fusion protein with His6 (SEQ ID NO:48)tag at the C-terminus (Khurana et al., *PLoS Med* 6:e1000049 (2009)). DNA encoding HA1 (1-330) of the A/Vietnam/1203/2004 and its various amino- and carboxytermini deletions were cloned as NotI-PacI inserts in the pSK expression vector.

Protein Expression, Refolding and Purification

*E. coli* Rosetta Gami cells (Novagen) were used for expression of various H5N1-A/Vietnam/1203/2004 HA1 and its various deletions. Following expression, inclusion bodies were isolated by cell lysis and multiple washing steps with 1% Triton X-100. Final Inclusion Bodies (IBs) pellet was resuspended in denaturation buffer containing 6 M Guanidine Hydrochloride and dithioerythreitol (DTE) at final protein concentration of 10 mg/ml and was centrifuged to remove residual debris. For refolding, supernatant was slowly diluted 100-folds in redox folding buffer. The renaturation protein solution was dialyzed against 20 mM Tris HCl pH 8.0 to remove the denaturing agents. The dialysate was filtered through 0.45 μM filter and was subjected to purification by H isTrap Fast flow chromatography.

Circular Dichroism (CD)-Monitored Equilibrium Unfolding Experiment

To demonstrate that the bacterially expressed HA fragments are properly folded they were analyzed by CD melt spectroscopy. For CD spectroscopy in solution, H1N1-HA proteins were dissolved in 20 mM PBS, pH 7.4, at 0.5 mg/ml. The change in elipticity at 222 nm (to follow unfolding of α-helices) during unfolding was monitored using a J-715 Circular Dichroism system (JASCO). The unfolding reaction was initiated by subjecting the protein in PBS to 1° C./min increments. The experiments were carried out in triplicate.

Gel Filtration Chromatography

Proteins at a concentration of 5 mg/ml were analyzed on Superdex S200 XK 16/60 column (GE-Healthcare) pre-equilibrated with PBS, and the protein elution was monitored at 280 nm. Protein molecular weight marker standards (GE healthcare) were used for column calibration and generation of standard curve to identify the molecular weights of the test protein sample.

Hemagglutination Assay

Human erythrocytes were separated from whole blood (Lampire Biologicals). After isolation and washing, 30 μl of 1% human RBC suspension (vol/vol in 1% BSA-PBS) were added to 30 µl serial dilutions of purified HA1 proteins or influenza virus in 1% BSA-PBS in a U-bottom 96-well plate (total volume, 60 µl). Agglutination was read after incubation for 30 min at room temperature Agglutination inhibition experiments were performed by using anti-H5N1 human MAb FLA5.10. Experiments were performed as described earlier, except that before addition to RBCs, HA proteins were preincubated for 15 min at room temperature with the human MAb.

Receptor Binding Assay Using Surface Plasmon Resonance

Binding of different HA1 derivatives to fetuin (natural homolog of sialic acid cell surface receptor proteins) and its asialylated counterpart (Asialo-fetuin) was analyzed at 25° C. using a ProteOn surface plasmon resonance biosensor (Bio-Rad Labs). Fetuin or Asialo-fetuin (Sigma) were coupled to a GLC sensor chip with amine coupling at 1000 resonance units (RU) in the test flow cells. Samples of 60 µl freshly prepared H5N1-HA1 proteins at 10 µg/ml were injected at a flow rate of 30 µl/min (120-sec contact time). Flow was directed over a mock surface to which no protein was bound, followed by the fetuin or asialo-fetuin coupled surface. Responses from the protein surface were corrected for the response from the mock surface and for responses from a separate, buffer only, injection. Binding kinetics and data analysis were performed with BioRad ProteON manager software (version 2.0.1).

Microneutralization Assay

Viral-neutralizing activity was analyzed in a microneutralization assay based on the methods of the pandemic influenza reference laboratories of the Center for Disease Control and Prevention (CDC). Low pathogenicity H5N1 viruses, generated by reverse genetics, were obtained from CDC: A/Vietnam/1203/2004 (SJCRH, clade 1), A/Indonesia/5/2005 (PR8-IBCDC-RG2; clade 2.1), A/Turkey/1/05 (NTBRG-23; clade 2.2), A/Anhui/1/05 (IBCDC-RG5, clade 2.3.4). The experiments were conducted with three replicates for each serum sample and performed at least twice.

Rabbit Immunization

New Zealand rabbits were immunized thrice intra-muscularly at 21-days interval with 100 µg of purified HA1 proteins and its derivatives with Titermax adjuvant (TiterMax Inc).

Ferret Immunization and Challenge Studies

Vaccination of Ferrets and Blood Collection

Ferrets (Marshall Farms, used in the study were tested to be sero-negative for circulating seasonal influenza A (H1N1 and H3N2) and influenza B viruses by HAI. Female Fitch ferrets (n=5 in each group) were vaccinated intramuscularly in the quadriceps muscle on day 0 and boosted on day 21 and then challenged with virus on day 35. Control animals (n=5) were mock vaccinated with phosphate buffered saline (PBS; pH 7.2). Each animal was vaccinated with one of two doses (15 µg or 3 µg) of recombinant HA in sterile 0.9% saline. Each vaccine was mixed with the adjuvant formulation, TiterMax (TiterMax USA, Inc, Norcross, Ga., US) at a 1:1 ratio. The volume for all intra-muscular vaccinations was 0.5 ml. The first and second vaccinations were given in the left and right hind legs, respectively. Blood was collected from anesthetized ferrets via the anterior vena cava. The collected blood was transferred to a tube containing a serum separator and clot activator and allowed to clot at room temperature. Tubes were centrifuged at 6000 rpm for 10 minutes; serum was separated, aliquoted and stored at −80±5° C. All procedures were in accordance with the National Research Council (NRC) Guidelines for the Care and Use of Laboratory Animals, the Animal Welfare Act, and the Centers for Disease Control (CDC)/National Institutes of Health (NIH) Bio-Safety Guidelines in Microbiological and Biomedical Laboratories and approved by the Institutional Animal Care and Use Committee (IACUC).

Infection and Monitoring of Ferret

Animal experiments with H5N1 influenza virus were performed in the AALAC-accredited ABSL-3 enhanced facility. Animals were infected and monitored as previously described (Zitzow et al., *J Virol* 76:4420-9 (2002)), except using 5% isofluorane anesthesia. Briefly, ferrets were anesthetized with isofluorane and infected intranasally with $1\times10^6$ 50% egg infectious doses ($EID_{50}$) ($\sim 1\times 10^{5.75}$ TCID50/ml) of A/Vietnam/1203/2004 (clade 1) or A/Whooperswan/Mongolia/244/2005 (clade 2.2) in a volume of one milliliter. Animals were monitored for temperature, weight loss, loss of activity, nasal discharge, sneezing and diarrhea daily following viral challenge. To determine viral load from nasal washes, 1.5 ml of 0.9% saline was administered to each nare and the wash was collected each day post-challenge of each ferret. Temperatures were measured through use of an implantable temperature transponder (BMDS, Sayre, Pa.) and were recorded at approximately the same time each day. Pre-infection values were averaged to obtain a baseline temperature for each ferret. Clinical signs of sneezing and nasal discharge, inappetence, dyspnea, neurological signs, respiratory distress, and level of activity were assessed daily. A scoring system was used to assess activity level where 0=alert and playful; 1=alert but playful only when stimulated; 2=alert but not playful when stimulated; 3=neither alert nor playful when stimulated. Based on the daily scores for each animal in a group, a relative inactivity index was calculated (Zitzow et al., *J Virol* 76:4420-9 (2002)).

Determination of Viral Loads

Viral loads in nasal washes were determined by the plaque assay. Briefly, MDCK cells plated in 6-well tissue culture plates were inoculated with 0.1 ml of virus-containing sample, serially diluted in Dulbecco's modified Eagle's medium (DMEM). Virus was adsorbed to cells for 1 h, with shaking every 15 min. Wells were overlaid with 1.6% w/v Bacto agar (DIFCO, BD Diagnostic Systems, Palo Alto, Calif., USA) mixed 1:1 with L-15 media (Cambrex, East Rutherford, N.J., USA) containing antibiotics and 0.6 mg/ml trypsin (Sigma, St. Louis, Mo., USA). Plates incubated for 5 days. Cells were fixed for 10 minutes using 70% v/v Ethanol and then overlaid with 1% w/v crystal violet. Cells were then washed with deionized water to visualize plaques. Plaques were counted and compared to uninfected cells.

Hemagglutinination Inhibition (HAI) Assay

RDE-treated ferret sera were serially diluted in v-bottom 96-well microtiter plates followed by the addition of 8 hemagglutination units (HAU) of influenza virus. Following an incubation of approximately 20 minutes, 0.5% suspension of horse RBC(HRBC) in PBS (pH 7.2) were added and mixed by agitation. The HRBCs were allowed to settle for 30 minutes at room temperature and HAI titers were determined by the reciprocal value of the last dilution of sera which completely inhibited hemagglutination of HRBC. A negative titer was defined as 1:10.

Results

Bacterially-expressed HA1 proteins with N- and C-terminal deletions are properly folded and bind H5N1-neutralizing human MAb FLA5.10.

To better understand the role of HA1 structure-function and its effect on generating protective immunity following immunization, we expressed a series of H5N1-derived HA1 proteins with N- and C-terminal deletions and evaluated their ability to form oligomers and to agglutinate red blood cells (RBC). The intact H5N1 HA1 and a series of truncated proteins were expressed in *E. coli* and isolated from inclusion bodies by denaturation and slow renaturation under controlled redox refolding conditions as previously described (Khurana et al., *Sci Transl Med* 2:15ra5; Khurana et al., *PLoS Med* 6:e1000049 (2009)). The His6 (SEQ ID NO:48)tagged fusion proteins were purified using Ni-NTA chromatography to >95% purity (FIG. 9A). Proper folding was confirmed by binding to a panel of H5N1-neutralizing human monoclonal antibodies (MAbs) that recognize conformational epitopes in the HA-RBD (Khurana et al., *PLoS Med* 6:e1000049 (2009)) and do not bind to unfolded HA proteins (Khurana et al., *Sci Transl Med* 2:15ra5). As shown in FIG. 9B, all bacterially expressed HA1 proteins containing receptor binding domain (RBD) bound human MAb FLA5.10 (as well as huMAbs FLD21.140 and FLD.3.14) with similar kinetics as determined by Surface Plasmon Resonance (SPR). HA (1-104) which does not contain the RBD did not bind to three huMAbs.

The interaction between individual HA RBD and the sialyloligosaccharides moieties is rather weak ($K_{diss}$>$10^{-4}$ M) (Matrosovich, M., and H. D. Klenk, *Rev Med Virol* 13:85-97 (2003)) and increased avidity is accomplished by binding of multimeric HA spikes to multiple cell receptors. To determine whether the recombinant HA1 proteins contain functionally active forms they were evaluated in human RBC hemagglutination assay. As positive controls we used the H5N1 vaccine strain rgA/Vietnam/1203/2004 and the licensed H5N1 inactivated vaccine (FIG. 9C). Both HA1 (1-330) and the HA1 (1-320) proteins agglutinated RBC, with endpoints of 97 and 4 ng/ml, respectively. CD melt spectroscopy demonstrated that the HA1 (1-320) protein was some what more stable than the HA1 (1-330) (melting temperatures of 54.3° C. and 51.8° C., respectively). Therefore, the deletion of 10 amino acid sequence at the carboxy-terminus of HA1 had a stabilizing effect on the HA1 protein, and improved hemeagglutination (FIG. 9C). In contrast, all the N-terminal deletions (5-320, 9-330, 17-330, and 28-330, and 28-320) did not agglutinate RBC (FIG. 9C).

The hemagglutination mediated by HA1 (1-330) and HA1 (1-320) was specific since it was blocked in a concentration dependent manner by preincubation with the H5N1-neutralizing huMAb FLA5.10 (but not by irrelevant MAb 2D7; not shown) (FIG. 9D).

Recombinant Ha1 Globular Domains Contain Oligomers

Figure 10:
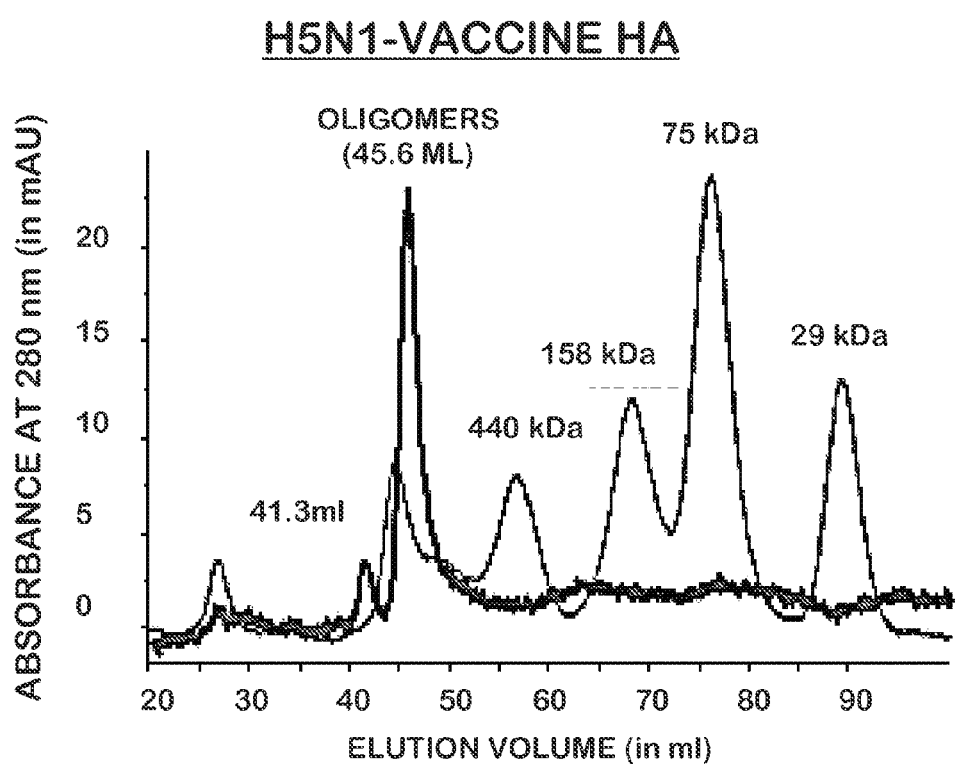
FIG. 10. Characterization of purified H5N1 HA proteins from E. coli and H5N1 vaccine by gel filtration chromatography, reducing and native gel electrophoresis and analytical centrifugation. Superdex S-200 gel filtration chromatography of bacterial H5N1 HA proteins and H5N1 vaccine. Purified H5N1 HA1 proteins with intact N-terminus (1-320) (A), HA1 with N-termini deletions (5-320) (B) and (28-320) (C), HA1 N-terminal peptide (1-104) (D), and H5N1 vaccine from the reassorted virus rgH5N1×PR8 (2:6) A/Vietnam/1203/2004 (clade 1) from Sanofi Pasteur (E) were subjected to gel filtration. The panels present superimposed elution profiles of purified HA proteins (red line) overlaid with calibration standards (grey line). The elution volumes of protein species are shown in parenthesis. SDS-PAGE analysis of bacterially purified H5N1 HA1 protein forms, and H5N1 vaccine in SDS-reducing (F), and Native gel (G). Different forms of bacterial produced H5N1 HA1-320 were purified from Superdex S200 XK 26/60 column (GE-Healthcare) and subjected to gel analysis along with the H5N1 vaccine from the reassorted virus rgH5N1×PR8 (2:6) A/Vietnam/1203/2004.

The hemagglutination results suggested that the intact HA1 (1-330 and 1-320), but not the N-terminus-deleted HA1 proteins, contain higher order quartenary forms required for RBC lattice formation. To address this possibility, the HA1 derivatives were subjected to gel filtration (FIG. 10 and FIG. 13) It was found that HA1 (1-320) contained ~80% high molecular weight (MW) oligomeric forms (FIG. 10A). In comparison, all the N-terminus deleted mutants appeared as monomers only (FIG. 10B-C, and FIG. 13). The H5N1 inactivated subunit vaccine (Sanofi Pasteur) contained only oligomers (FIG. 10E). Interestingly, HA1 (1-104) segment, devoid of the RBD, also formed oligomers (FIG. 10D). In addition to size chromatography, the monomeric and oligomeric peaks of HA1 (1-320) were isolated from the gel filtration and were analyzed by native SDS-PAGE (FIG. 10F) as well as reduced SDS-PAGE gel (FIG. 10G). H5N1 vaccine was included as a positive control. In the native gel, monomeric fraction of HA1 (1-320) ran at the expected MW (FIG. 10F lane 1), while the oligomeric fraction contained multiple high MW species, similar to the H5N1 inactivated vaccine (FIG. 10F lanes 2 and 3). In SDS-PAGE under reducing conditions, the bacterially expressed HA1 monomeric and oligomeric fractions all ran as monomers (FIG. 10G lanes 1-2). As expected, the vaccine H5N1 HA was dissociated into HA1 and HA2 (FIG. 10G lane 3). Sedimentation velocity data collected by analytical centrifugation suggested that the oligomeric fraction of the rHA1 (1-320) contained multiples of trimers with majority of oligomers consisting of 4-6 trimers (data not shown).

Oligomeric Forms of HA1 are Required for Receptor Binding and Hemagglutination

To further investigate which HA1 forms are required for receptor binding and RBC agglutination, we established a fetuin based Surface Plasmon Resonance (SPR) assay that mimics the simultaneous interactions between the virion HA spikes with sialic acid moieties (Takemoto et al., *Virology* 217:452-8 (1996)). All H5N1-HA1 mutants and truncated proteins were tested for binding to fetuin coated on biosensor chips. As shown in FIG. 12A, HA1 (1-320) showed higher binding to fetuin coated surface, than HA1 (1-330). The H5N1 vaccine bound fetuin at similar rate to HA1 (1-320), but dissociated slower (FIG. 12A). The levels of fetuin binding by HA1 (1-320) vs. HA1 (1-330) correlated well with the RBC agglutinations demonstrated in FIG. 9C (top 2 rows) and confirmed that the 10 aa C-terminus deletion stabilized the functional oligomeric HA1. No binding to asialo-fetuin was observed, confirming the binding specificity of these proteins to sialyated glycoproteins (FIG. 12B). To better understand the role of monomers and oligomers in receptor binding and hemagglutination, a preparative gel filtration column was used to isolate monomers and oligomers of HA1 (1-320). Only fractions containing oligomers, but not monomers, bound to fetuin in the SPR assay (FIG. 12C, curves), and agglutinated RBC (FIG. 12D), while both monomeric and oligomeric forms were properly folded as determined by binding to three conformation dependent H5N1 neutralizing human MAbs in SPR (data not shown). All the HA1 proteins with N-terminal deletions or mutations, consist only of monomers, and did not bind fetuin (FIG. 12A and FIG. 13). The N-terminal (1-104) formed oligomers (FIG. 10D), but did not bind fetuin and did not agglutinate RBC as it did not contain the receptor binding domain (FIG. 13).

N-Terminal Amino Acids Ile-Cys-Ile are Required for HA1 Oligomerization.

Alignment of the N-terminal amino acids of the HA protein from representative strains of 16 different influenza A hemagglutinin subtypes identified amino acids $I_3C_4I_5G_6$ (SEQ ID NO:46)as highly conserved. Since deletion of only four residues in the N-terminus of HA1 (HA 5-320) was sufficient to prevent RBC agglutination (FIG. 9), we constructed two mutants of HA1 ($I_3C_4I_5$>$A_3A_4A_5$) and ($I_3C_4I_5$>$G_3A_4G_5$). These mutations did not affect protein folding as determined by binding to huMAb FLA5.10. However, both mutated proteins contained only 20 monomers and did not agglutinate RBC (FIG. 13).

These data suggested that in the absence of HA2, the HA1 globular domain can use an oligomerization signal in the N-terminus that encompass the highly conserved amino acid residues at position 3-5 of influenza hemagglutinin.

Oligomers-Containing HA1 Proteins Elicit Broadly Cross-Neutralizing Antibodies in Rabbits We next compared the immunogenicity of bacterially-expressed monomeric HA1 (28-320) with that of HA1 (1-320) protein (~80% oligomers) in rabbits. Microneutralization assay was used to evaluate both homologous and heterologous neutralizing capacity of post-vaccination rabbit sera following 3-4 consecutive immunizations (100 µg protein per dose) (FIG. 14). After two immunizations, the monomeric HA1 (28-320) elicited modest neutralizing antibody titers (1:80) against homologous virus (A/Vietnam/1203/2004;

clade 1), which increased 4 fold by the 4th immunization. Cross neutralization of A/Turkey/1/2005 (clade 2.2) and A/Anhui/1/2005 (clade 2.3.4), but not of AJIndonesia/5/2005 (clade 2.1) was also observed (FIG. 14A, top panel). In contrast, rabbits immunized with oligomeric HA1 (1-320), showed a faster kinetics of immune response and broader cross-clade neutralization. A titer of 1:160 against A/Vietnam/1203/2004 was measured after the second immunization, and increased dramatically to 1:5,120 after the third vaccination. Importantly, cross-clade neutralizing titers were also very robust against heterologous HP H5N1 AIV including A/Indonesia/5/2005 (clade 2.1), which is more difficult to cross neutralize (FIG. 14A, bottom panel).

In order to determine if vaccination with oligomeric HA1 elicit antibodies which are oligomer-specific, post vaccination sera from K1 rabbit (vaccinated with HA1 1-320) and K3 rabbit (vaccinated with HA1 28-320) were absorbed with the monomeric (28-320) or oligomeric (1-320) proteins followed by binding to SPR sensor chips coated with oligomeric fraction of HA1. (FIG. 11A), or monomeric fraction of HA1 (1-320) (FIG. 11B). Adsorption of either sera with the HA1 (1-320) removed SPR binding to the two proteins (FIG. 11). On the other hand, $K_1$ serum that was adsorbed with the monomeric fraction of HA1 (1-320), still bound at low level to the chip coated with the oligomeric HA1 (1-320) protein (FIG. 11A) but not to the chip coated with the monomeric protein (FIG. 11B). These findings suggested the presence of oligomeric-specific antibodies in the sera of K1 rabbit, which were not adsorbed by the monomeric HA1 (28-320) protein. The presence of trimer-specific anti-HA antibodies (seasonal), has been previously suggested (Copeland et al., *J Cell Biol* 103:1179-91 (1986)).

Oligomeric but not Monomeric Ha1 Immunogens Protect Ferrets from Homologous and Heterologous Challenge with HP H5N1 AIV To further evaluate the ability to generate protective immunity with bacterially expressed HA1 proteins we used the ferret model, which is extremely susceptible to highly pathogenic H5N1 influenza infections. Since the pattern of influenza virus attachment to the lower respiratory tract resulting in influenza-associated pneumonia in ferrets resembles influenza infections in humans, this model has been widely used to evaluate influenza pathogenesis and vaccines (Maher, J. A., and J. DeStefano, *Lab Anim* (NY) 33:50-3 (2004); van Riel et al., *Am J Pathol* 171:1215-23 (2007)). Ferrets were vaccinated twice with either 3 μg or 15 μg of either oligomeric HA1 globular protein (HA 1-320) or the N-terminus deleted monomeric HA1 (HA 28-320), on days 0 and 21. The antigen doses were selected based on seasonal influenza vaccines, and the need for dose sparing. Fourteen days after the second immunization, unvaccinated and vaccinated animals were challenged intranasally with highly pathogenic H5N1 ANietnam/1203/2004 (clade 1, homologous to the vaccine stain) or with the H5N1 A/Whooperswan/Mongolia/244/2005 (clade 2.2) AIV at a pre-determined lethal dose (106 EID50). Animals were monitored for 10 days for lethality, weight loss and sickness scores.

Figure 15:
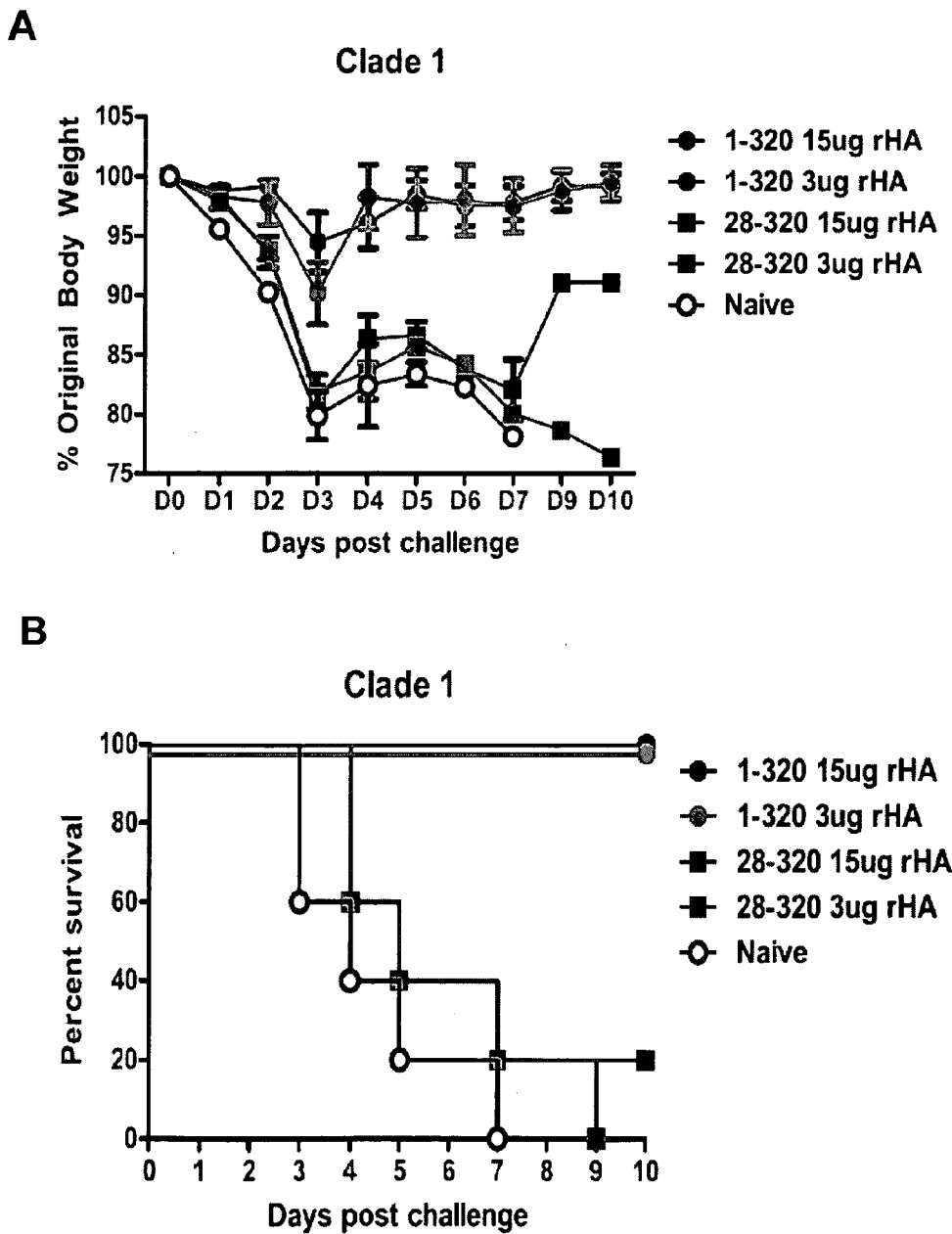
FIG. 15. Challenge of vaccinated and unvaccinated ferrets with H5N1 influenza viruses. Following two immunizations with bacterial H5N1— Vietnam HA1 (1-320) or HA (28-320), ferrets (five animals per group) were infected intranasally with $1 \times 10^6$ 50% egg infectious doses ($EID_{50}$) of A/Vietnam/1203/2004 (clade 1) (A and B) or A/Whooperswan/Mongolia/244/2005 (clade 2.2) (C and D). Animals were scored for percent original body weight (A and C) and percent survival (B and D). Viral loads in nasal washes following challenge of vaccinated and unvaccinated ferrets with H5N1 influenza viruses, A/Vietnam/1203/2004 (clade 1) (E and F) or A/Whooperswan/Mongolia/244/2005 (clade 2.2) (G and H) on day 3 (E and G) or day 5 (F and H) post-virus challenge. Data are presented for individual animals. Horizontal lines represent average pfu of virus from the nasal washes of each group (5 ferrets per group).
Figure 15:
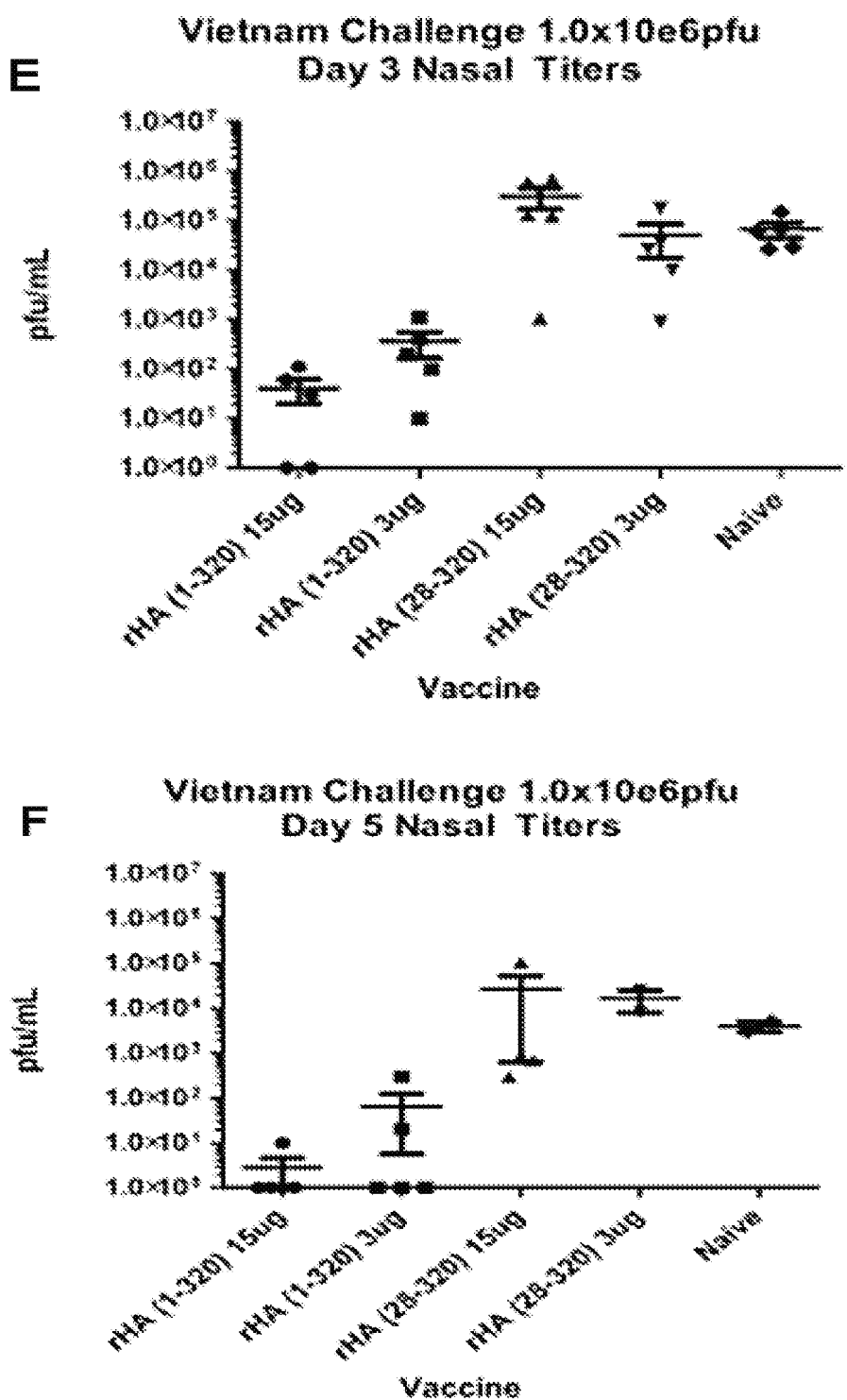

The hemagglutinaton inhibition (HI) titers following two vaccinations with rHA1 (1-320) ranged between 1:40-1:640 (Average: 1:204) and between 1:10-1:320 (Average 1:141) for the 15 μg and 3 μg dose, respectively. The rHA1 (28-320) did not generate HI titers in any of the vaccinated animals. Following intranasal challenge with HP avian viruses A/Vietnam/1203/2004 and A/Whooperswan/244/2005, all unvaccinated ferrets developed severe symptoms, lost weight progressively, and died within 3-7 days following challenge (FIG. 15A-B, black open circles). The N-terminus-deleted HA1 (28-320) that contains only monomers did not protect animals from weight loss and lethality at the 3 μg dose (FIG. 15A-B), and only one animal survived homologous H5N1 A/Vietnam/1203/2004 challenge at the 15 μg vaccine dose (FIG. 15A-B). In contrast, ferrets vaccinated with HA1 (1-320) with either 3 μg or 15 μg dose, were fully protected from lethality (FIG. 15B). These animals showed only a minor transient weight loss on day 3 (≤10%) followed by a full recovery without any signs of symptoms by day 4 after homologous (A/Vietnam/1203/2004) virus challenge (FIG. 15A). Importantly, HA1 (1-320) immunization also protected ferrets against heterologous challenge with highly pathogenic clade 2.2 virus (H5N1 A/Whooperswan/244/2005), resulting in 80% survival rate and <10% weight loss in both the high and low dose vaccinated groups (FIG. 15C-D).

In addition to protection from mortality and morbidity, viral loads in the nasal washes of HA1 (1-320) vaccinated animals were reduced by 2-5 logs on days 3 and 5 post challenge compared with unvaccinated animals or with animals vaccinated with monomeric HA1 (FIG. 15E-H). Reduction in viral loads following heterologous challenge was more modest (1-2 logs). Such reduction in viral loads in the nasal cavities is predicted to also reduce virus transmission.

Together, our data demonstrated that bacterially expressed HA1 proteins that are properly folded and contain functional oligomers, can elicit protective immunity against highly pathogenic vaccine-matched as well as heterologous avian influenza viruses.

Discussion

Expression of recombinant HA proteins in bacteria could provide a rapid and economical approach for early response to impending influenza pandemic. Early studies demonstrated that protective influenza antigenic sites are conformation dependent and map primarily to HA1 globular domain. Therefore, producing HA1 proteins in properly folded state is imperative to eliciting protective antibody responses.

In the current study we have dissected the structure-function requirements of bacterially expressed HA1 proteins and evaluated their potential use as prophylactic vaccines against highly pathogenic H5N1 AIV. The main findings are: (a) a panel of HA1 proteins with N- and C-terminal deletions purified from *E. coli* under careful redox conditions were shown to be properly folded by binding to conformation-dependent huMAb; (b) HA1 with intact N-terminus contained oligomers in addition to monomers, while HA1 with N-terminal deletions contained only monomers; (c) fetuin receptor binding assay demonstrated that only HA1 proteins with intact N-termini, containing oligomers, bound receptors; (d) hemagglutination required oligomeric HA1; (e) site directed mutagenesis of Ile-Cys-Ile residues at positions 3-5 disrupted oligomer formation, fetuin binding and RBC agglutination with no effect on HA1 folding; (f) in rabbits, properly folded HA1 containing oligomers, generated more rapid potent neutralizing antibodies than monomeric HA1 and cross neutralized several H5N1 clades including A/Indoensia/5/2005; (g) vaccination of ferrets with HA1 (1-320) at either 3 or 15 μg protein per dose, protected animals from lethality and morbidity following challenge with homologous (A/Vietnam/1203/2004) or heterologous (A/Whooperswan/Mongolia/244/2005) HP AIV challenge. In contrast, monomeric HA1 (28-320) was not immunogenic in ferrets at the same doses, and did not protect animals from H5N1 challenge.

The structure of HA from highly pathogenic H5N1 A/Vietnam/1203/2004 resembles the 1918 and other human H1 HA (Stevens et al., *J Mol Biol* 355:1143-55 (2006); Xu et al., *Science* 328:357-60 (2010); Xu et al., R., *J Virol* 84:1715-21). Most of the inter subunit salt bridges and hydrophobic interactions are between the HA2 chains due to coiled-coil structure which forms the stem of the HA trimer (Boulay et al., *J Cell Biol* 106:629-39 (1988); Copeland et al., *J Cell Biol* 103:1179-91 (1986); Daniels et al., *Cell* 40:431-9 (1985); Doms et al., *J Virol* 57:603-13 (1986); Doms, R. W., and A. Helenius., *J Virol* 60:833-9 (1986)). These earlier HA-structural studies did not describe the oligomerization signal in the HA1 globular domain identified in the current study, suggesting that in the presence of HA2 the N-terminus β-sheet structure is engaged in HA1-HA2 bridge and not in HA1 oligomerization. This might explain why most recombinantly expressed HA ectodomain proteins exist as monomers, and require the addition of multimerization sequences like "foldon" at the C-terminus in order to produce stable oligomeric structures (Wei et al., *J Virol* 82:6200-8 (2008)). This was further confirmed in a recent study in our laboratory with bacterially expressed HA proteins from the novel H1N1 A/California/04/2009 comparing the composition and immunogenicity of globular HA1 (1-330) with that of the HA ectodomain (1-480). Both proteins were properly folded. However, only the HA1 globular head (1-330) formed oligomers and agglutinate human RBC, while the HA ectodomain (1-480) contained only monomers and did not agglutinate RBC (Khurana et al., *PLoS One* 5:e11548). It is likely that in native spikes the N-terminal β-sheets of the three HA1 globular domains are not in sufficient proximity to form oligomers, but in the absence of HA2 they are free and close enough to provide the needed oligomerization signal. This was confirmed by our finding that a N-terminal fragment HA1 (1-104) without the receptor binding domain appeared primarily as oligomers in gel filtration chromatography (FIG. 10D)

In mammalian and eukaryotic cells, post-translational glycosylation of HA was shown to play an important role in proper folding, trimer stabilization, and transport to the cell outer membrane (Ceriotti, A., and A. Colman, *J Cell Biol* 111:409-20 (1990); Copeland et al., *J Cell Biol* 103:1179-91 (1986); Roberts et al., *J Virol* 67:3048-60 (1993)). On the other hand, we have demonstrated in this and previous studies that bacterially expressed unglycosylated HA can be purified as properly folded proteins as determined by CD spectra analysis and binding to conformation-dependent neutralizing monoclonal antibodies (Khurana et al., *Sci Transl Med* 2:15ra5; Khurana et al., *PLoS Med* 6:e1000049 (2009)).

Importantly, our study demonstrated that in addition to proper folding, HA1 oligomers were required for high avidity receptor (fetuin) binding and for cross-linking of RBC resulting in hemagglutination. Other reports on the production of recombinant HA in mammalian cells, insect cells, or bacterial systems, did not provide information on the presence and function of oligomers vs. monomeric forms of HA (Lakey et al., *J Infect Dis* 174:838-41 (1996); Powers et al., *J Infect Dis* 175:342-51 (1997); Shen et al., *J Med Virol* 80:1972-83 (2008); Song et al., *PLoS One* 3:e2257 (2008); Treanor et al., *Vaccine* 19:1732-7 (2001); Wang et al., *Vaccine* 24:2176-85 (2006)).

Figure 9:
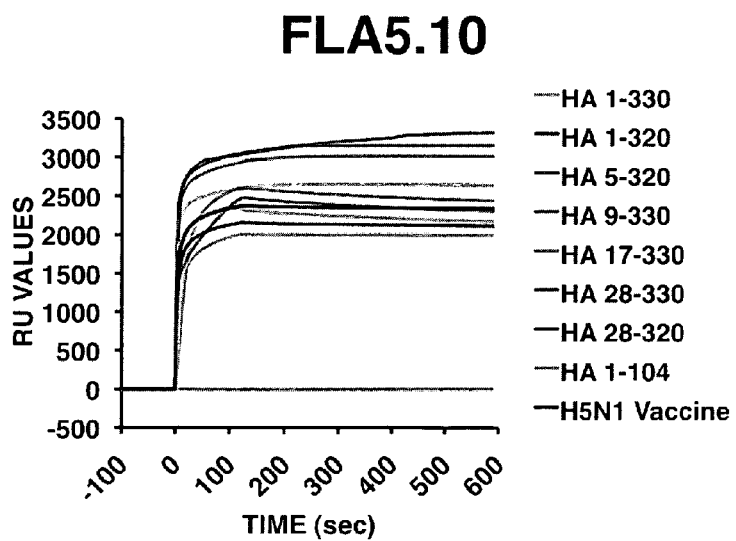
FIG. 9. Biochemical and functional characterization of bacterially expressed and purified H5N1 HA proteins. (A) Panel of A/Vietnam/1203/2004 (H5N1) HA1 domain (aa 1-330) and N- and C-termini deletions were expressed in E. coli as fusion proteins with His6 tag at the C-termini. The purified proteins ran as single bands at the expected molecular weights in reducing SDS-PAGE. (B) Steady-state binding equilibrium analysis of human H5N1 neutralizing MAb FLA5.10 (10 µg/ml) to purified bacterially expressed H5N1 Ha 1 proteins immobilized on a sensor chip through the free amine group, and onto a blank flow cell, free of peptide. H5N1 vaccine from the reassorted virus rgH5N1×PR8 (2:6) A/Vietnam/1203/2004 (clade 1) from Sanofi Pasteur was also analyzed. Binding was recorded using ProteOn system surface plasmon resonance biosensor instrument (BioRad Labs, Hercules, Calif.). Similar results were obtained with two additional broadly neutralizing human Mabs FLD21.140 & FLA3.14 (C) Agglutination of human RBC by properly folded bacterial H5N1 HA1 (1-330) protein and its deletion derivatives along with H5N1 vaccine. Serial dilutions of purified HA1 proteins were mixed with washed RBC and hemagglutination was read after 30 min at RT. Reassorted virus rgH5N1×PR8 (2:6) A/Vietnam/1203/2004 (clade 1.0) was used as a positive control. H5N1 vaccine was used at a starting concentration of 1 µg/ml. (D) H5N1-Neutralizing MAb FLA 5.10 specifically blocks agglutination of human RBC by recombinant HA1 (1-330), and HA1 (1-320) proteins, and of rgH5N1×PR8 virus. Two-fold serial dilutions of MAb FLA5.10 were pre-incubated with purified HA1 proteins or virus before mixing with washed RBC.

Our data on the importance of high MW oligomers for optimal immunogenicity of influenza HA proteins is in agreement with a report on mammalian cell expressed HA ectodomain, which required the addition of multimerization "foldon" at the C-terminus in order to produce stable oligomeric structures (Wei et al., *J Virol* 82:6200-8 (2008)) and to elicit optimal neutralizing antibody titers. However, in the case of bacterially expressed HA1, no requirement for a foldon like sequence was found. Importantly, the traditional inactivated subunit vaccine generated from egg grown virus contains primarily oligomeric forms (FIG. 9). Therefore, our bacterially expressed and properly folded HA1 proteins with intact N-terminus behave similar to inactivated H5N1 subunit vaccines in terms of in vitro functions including receptor binding and RBC agglutination.

The ferret protection data with highly pathogenic avian H5N1 studies provide strong evidence that bacterially expressed HA1 proteins, which are properly folded and contain functional oligomers, are potent inducers of protective immunity against pathogenic influenza viruses. While all H5N1 viruses are between 95 to 98% identical regardless of Glade, there is poor cross-reactivity between antibodies elicited to clade 1 HP H5N1 viruses, such as A/Vietnam/04 and clade 2 H5N1 viruses that predominate the recently transmitted strains resulting in high human lethality. The cross protection against heterologous strains is of importance since it is not certain which of the avian H5N1 influenza strains will adapt to human to human transmission.

Figure 16:
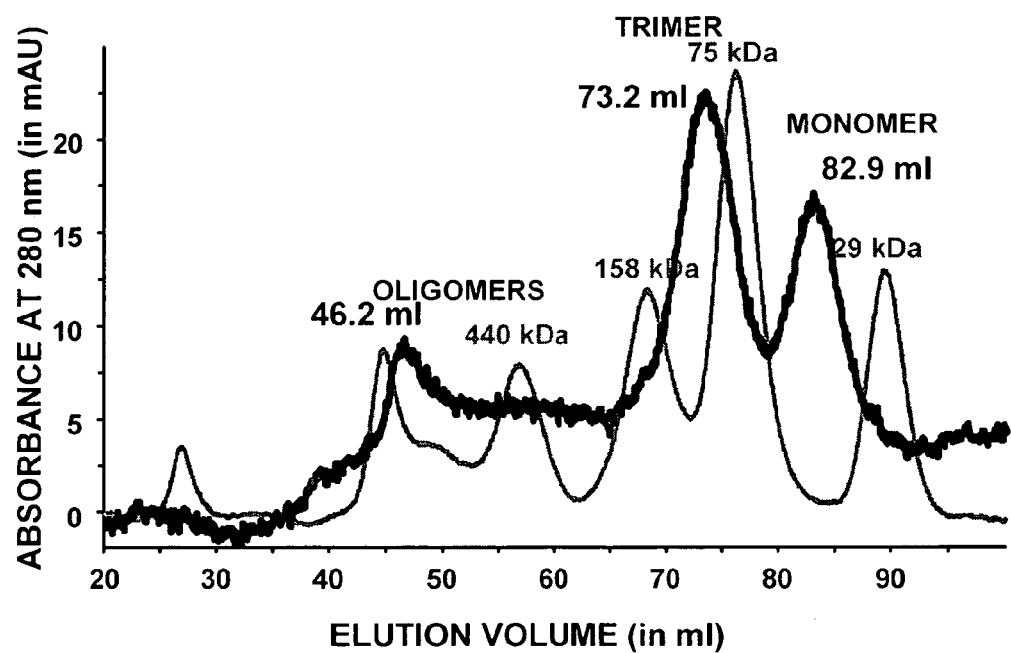
FIG. 16. HA1 Proteins from different Influenza strains form oligomers. Superdex S-200 gel filtration chromatography of purified HA1 proteins from recent Influenza A strains in E. coli. Purified HA1 proteins with intact N-terminus from pandemic strain, A/Indonesia/5/2005, A/California/07/2009 & H7N7 A/Netherlands/219/03 and two recent human influenza strains, H3N2 A/Victoria/210/2009 & H3N2 A/Wisconsin/15/2009. The panels present superimposed elution profiles of purified HA proteins (bolded line) overlaid with calibration standards (less bold line). The elution volumes of protein species are shown in parenthesis.
Figure 18:
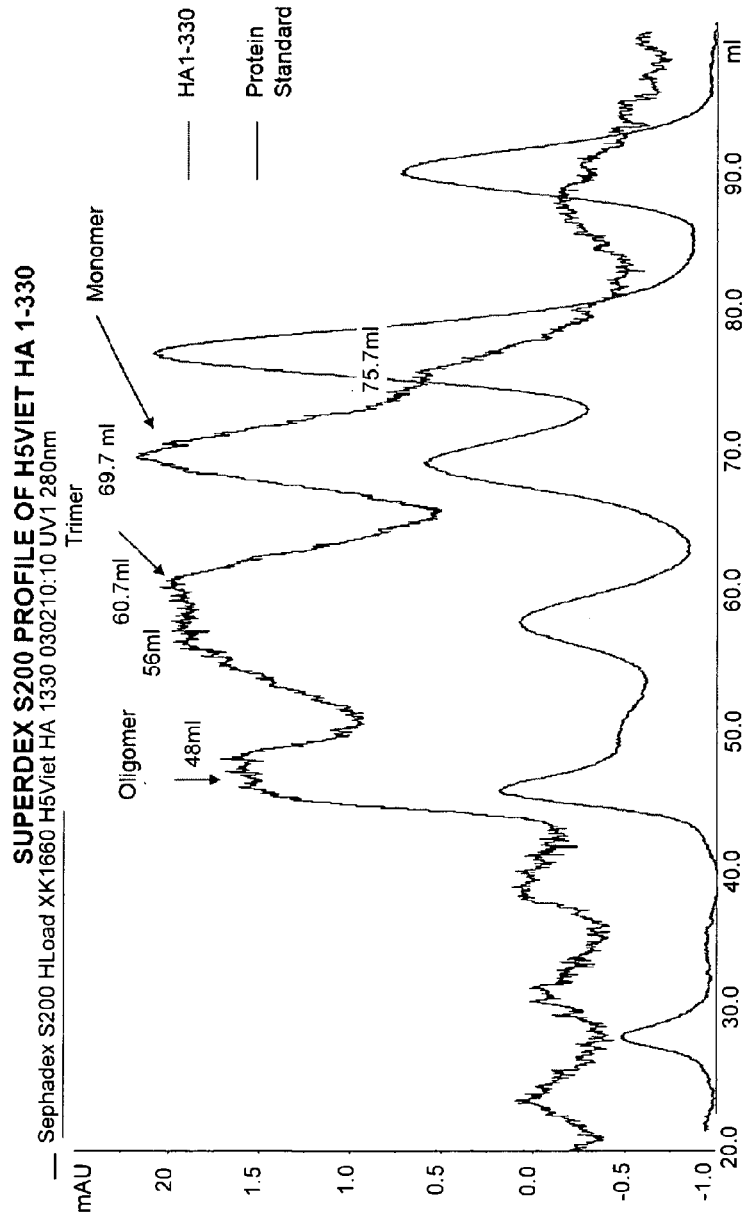
FIG. 18. Superdex S-200 gel filtration chromatography of purified HA1 proteins from A/Vietnam/1203/2004 expressed in Mammalian cells. Purified glycosylated HA1 protein with intact N-terminus (aa 1-330) from A/Vietnam/1203/2004 expressed in 293 cells using a CMV based expression vector represents higher order quarternary structures (including trimeric and oligomeric forms). The panel present superimposed elution profile of purified HA1 protein (top line at left) overlaid with calibration standards (bottom line at left).

The combination of recombinant technology and improved purification approaches, combined with analytical assays to confirm proper folding and higher order quarternary structures will facilitate large scale production of HA in bacterial systems. Within two weeks of pandemic strain isolation high quantities of HA1 proteins can be produced (currently 40-50 mg/Liter in a batch culture; with 8-10 fold higher yields in small scale continuous fermentation culture). Thus far, we have generated bacterially expressed properly folded HA1 from two H5N1 strains (A/Vietnam/1203/2004; clade 1 & A/Indonesia/5/2005; Glade 2.1), novel H1N1 (A/California/04/2009), H3N2 (A/Wisconsin/15/2009 & A/Victoria/210/2009), and H7N7 (A/Netherlands/219/03), and all were shown to form functional oligomers (≥70%), with lot to lot consistency (FIG. 16).

Therefore, production of HA1 (1-320) proteins in bacterial systems is a viable and scalable approach for rapid vaccine production in response to emerging influenza strains with little or no pre-existing immunity (such as H5N1 influenza), especially for individuals with known egg allergies.

The examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Informal Sequence Listing

SEQ ID NO: 1
A/California/04/2009(H1N1) HA1-480
DTLCIGYHANNSTDTVDTVLEKNVTVTHSVNLLEDKHNGKLCKLRGVAPLHLGKCNIAGW

ILGNPECESLSTASSWSYIVETPSSDNGTCYPGDFIDYEELREQLSSVSSFERFEIFPKT

SSWPNHDSNKGVTAACPHAGAKSFYKNLIWLVKKGNSYPKLSKSYINDKGKEVLVLWGIH

-continued

HPSTSADQQSLYQNADTYVFVGSSRYSKKFKPEIAIRPKVRDQEGRMNYYWTLVEPGDKI

TFEATGNLVVPRYAFAMERNAGSGIIISDTPVHDCNTTCQTPKGAINTSLPFQNIHPITI

GKCPKYVKSTKLRLATGLRNIPSIQSRGLFGAIAGFIEGGWTGMVDGWYGYHHQNEQGSG

YAADLKSTQNAIDEITNKVNSVIEKMNTQFTAVGKEFNHLEKRIENLNKKVDDGFLDIWT

YNAELLVLLENERTLDYHDSNVKNLYEKVRSQLKNNAKEIGNGCFEFYHKCDNTCMESVK

SEQ ID NO: 2
A/Vietnam/1203/2004(H5N1) HA1-320
DQICIGYHANNSTEQVDTIMEKNVTVTHAQDILEKKHNGKLCDLDGVKPLILRDCSV

AGWLLGNPMCDEFINVPEWSYIVEKANPVNDLCYPGDFNDYEELKHLLSRINHFEKI

QIIPKSSWSSHEASLGVSSACPYQGKSSFFRNVVWLIKKNSTYPTIKRSYNNTNQEDL

LVLWGIHHPNDAAEQTKLYQNPTTYISVGTSTLNQRLVPRIATRSKVNGQSGRMEFF

WTILKPNDAINFESNGNFIAPEYAYKIVKKGDSTIMKSELEYGNCNTKCQTPMGAINS

SMPFHNIHPLTIGECPKYVKSNRLVLATGLRNS

SEQ ID NO: 3
A/California/04/2009(H1N1) HA1-330
DTLCIGYHANNSTDTVDTVLEKNVTVTHSVNLLEDKHNGKLCKLRGVAPLHLGKCN

IAGWILGNPECESLSTASSWSYIVETPSSDNGTCYPGDFIDYEELREQLSSVSSFERFEI

FPKTSSWPNHDSNKGVTAACPHAGAKSFYKNLIWLVKKGNSYPKLSKSYINDKGKE

VLVLWGIHHPSTSADQQSLYQNADTYVFVGSSRYSKKFKPEIAIRPKVRDQEGRMNY

YWTLVEPGDKITFEATGNLVVPRYAFAMERNAGSGIIISDTPVHDCNTTCQTPKGAIN

TSLPFQNIHPITIGKCPKYVKSTKLRLATGLRNIPSIQSR

SEQ ID NO: 4
A/Indonesia/5/2005(H5N1) HA1-320
DQICIGYHANNSTEQVDTIMEKNVTVTHAQDILEKTHNGKLCDLDGVKPLILRDCSV

AGWLLGNPMCDEFINVPEWSYIVEKANPTNDLCYPGSFNDYEELKHLLSRTNHFEKI

QIIPKSSWSDHEASSGVSSACPYLGSPSFFRNVVWLIKKNSTYPTIKKSYNNTNQEDLL

VLWGIHHPNDAAEQTRLYQNPTTYISIGTSTLNQRLVPKIATRSKVNGQSGRMEFFW

TILKPNDAINFESNGNFIAPEYAYKIVKKGDSAIMKSELEYGNCNTKCQTPMGAINSS

MPFHNIHPLTIGECPKYVKSNRLVLATGLRNS

SEQ ID NO: 5
A/Victoria/210/2009(H3N2) HA1-330
SWNDNSTATLCLGHHAVPNGTIVKTITNDQIEVTNATELVQNSSTGEICDSPHQILDG

KNCTLIDALLGDPQCDGFQNKKWDLFVERSKAYSNCYPYDVPDYASLRSLVASSGT

LEFNNESFNWTGVTQNGTSSACIRRSKNSFFSRLNWLTHLNFKYPALNVTMPNNEQF

DKLYIWGVHHPVTDKDQIFLYAQASGRITVSTKRSQQTVIPNIGSRPRVRNIPTRISIY

WTIVKPGDILLINSTGNLIAPRGYFKMQSGKSSMRSDAPIGKCNSECITPNGSIPNDKP

FQNVNRITYGACPRYVKQNTLKLATGMRNVPEKQTR

SEQ ID NO: 6
A/Wisconsin/15/2009(H3N2) HA1-330
SWNDNSTATLCLGHHAVPNGTIVKTITNDQIEVTNATELVQSSSTGEICDSPHQILDG

KNCTLIDALLGDPQCDDFQNKKWDLFVERSKAYSNCYPYDVPDYASLRSLVASSGT

LEFNNESFNWTGVTQNGTSSACIRRSKNSFFSRLNWLTHLNFKYPALNVTMPNNEQF

DKLYIWGVHHPGTDKDQIFPYAQASGRITVSTKRSQQTAIPNIGSRPRVRNIPSRISIY

WTIVKPGDILLINSTGNLIAPRGYFKIRSGKSSIMRSDAPIGKCNSECITPNGSIPNDKPF

QNVNRITYGACPRYVKQNTLKLATGMRNVPEKQTR

SEQ ID NO: 7

A/Netherlands/219/03(H7N7) HA1-320
DKICLGHHAVSNGTKVNTLTERGVEVVNATETVERTNVPRICSKGKRTVDLGQCGL

LGTITGPPQCDQFLEFSADLIIERREGSDVCYPGKFVNEEALRQILRESGGIDKETMGF

TYSGIRTNGTTSACRRSGSSFYAEMKWLLSNTDNAAFPQMTKSYKNTRKDPALIIWG

IHHSGSTTEQTKLYGSGNKLITVGSSNYQQSFVPSPGARPQVNGQSGRIDFHWLILNP

NDTVTFSFNGAFIAPDRASFLRGKSMGIQSEVQVDANCEGDCYHSGGTIISNLPFQNI

NSRAVGKCPRYVKQESLLLATGMKNV

---

What is claimed is:

1. A composition comprising oligomers of unglycosylated polypeptides, the polypeptides comprising:

a. at least a portion of an influenza Hemagglutinin-1 (HA-1) domain; and b. lacking:

an Hemagglutinin-2 (HA-2) domain; or both an Hemagglutinin-2 (HA-2) domain and an Hemagglutinin transmembrane domain;

wherein administration of the composition to an animal generates neutralizing antibodies against an influenza virus.

2. A physiological vaccine composition comprising, the composition of claim 1; and a physiological excipient.

3. The composition of claim 2, further comprising an adjuvant.

4. A method of inducing an immune response against an influenza Hemagglutinin in an animal, the method comprising, administering an amount of the composition of claim 2 to the animal sufficient to induce said immune response.

5. The composition of claim 1, wherein said portion comprises an influenza amino acid sequence comprising the amino acids isoleucine (I) or leucine (L) at the amino acid corresponding to position 3, the amino acid cysteine (C) at the amino acid corresponding to position 4, the amino acids I, L, or valine (V) at the amino acid corresponding to position 5, and the amino acid glycine (G) at the amino acid corresponding to position 6 of SEQ ID NO:2.

6. The composition of claim 5, wherein the polypeptide comprises a sequence of SEQ ID NO:1, 3, 4, 5, 6, or 7 or a sequence that corresponds to positions 1-259 of SEQ ID NO:2.

7. The composition of claim 5, wherein the polypeptide binds to conformation sensitive influenza neutralizing antibodies.

8. The composition of claim 5, wherein the amino acid sequence is at least 80% identical to positions 1-259 of SEQ ID NOS:1, 2, 3, 4, 5, 6, or 7.

9. The composition of claim 8, wherein the portion comprises positions 1-259 of SEQ ID NOS:1, 2, 3, 4, 5, 6, or 7.

10. The composition of claim 5, wherein the portion consists of an influenza amino acid sequence at least 80% identical to an amino acid sequence corresponding to positions 1-259 of SEQ ID NOS:1, 2, 3, 4, 5, 6, or 7.

11. The composition of claim 5, wherein the portion comprises an influenza amino acid sequence corresponding to positions 1-320 of SEQ ID NOS:1, 2, 3,4 ,5, 6 or 7.

12. The composition of claim 11, wherein the amino acid sequence comprises a sequence of SEQ ID NO:1, 3, 4, 5, 6, or 7 or a sequence that corresponds to positions 1-320 of SEQ ID NO:2.

13. The composition of claim 11, wherein the amino acid sequence is at least 80% identical to positions 1-320 of SEQ ID NOS:1, 2, 3, 4, 5, 6, or 7.

14. The composition of claim 11, wherein the portion comprises positions 1-320 of SEQ ID NOS:1, 2, 3, 4, 5, 6, or 7.

15. The composition of claim 11, wherein the portion consists of an amino acid sequence at least 80% identical to positions 1-320 of SEQ ID NOS:1, 2, 3, 4, 5, 6, or 7.

16. The composition of claim 11, wherein the portion consists of an influenza amino acid sequence at least 80% identical to an amino acid sequence corresponding to positions 1-320 of SEQ ID NOS:1, 2, 3, 4, 5, 6, or 7.

17. The composition of claim 5, wherein the portion comprises an influenza amino acid sequence corresponding to positions 1-330 of SEQ ID NO:1.

18. The composition of claim 1, wherein said portion comprises amino acids corresponding to positions 2 to 7 of SEQ ID NO:2 substituted into the corresponding positions of a heterologous HA1 polypeptide selected from: (a) SEQ ID NO:1, 3, 5, 6, or 7, or (b) a sequence that corresponds to positions 1 to 320 of SEQ ID NO:2.

* * * * *

SEQUENCE LISTING

<160> NUMBER OF SEQ ID NOS: 48

<210> SEQ ID NO 1
<211> LENGTH: 480
<212> TYPE: PRT
<213> ORGANISM: Influenza A virus
<220> FEATURE:
<223> OTHER INFORMATION: Influenza A/California/04/2009(H1N1)
      hemagglutinin HA1-480 domain

<400> SEQUENCE: 1

```
Asp Thr Leu Cys Ile Gly Tyr His Ala Asn Asn Ser Thr Asp Thr Val
 1               5                  10                  15

Asp Thr Val Leu Glu Lys Asn Val Thr Val Thr His Ser Val Asn Leu
             20                  25                  30

Leu Glu Asp Lys His Asn Gly Lys Leu Cys Lys Leu Arg Gly Val Ala
         35                  40                  45

Pro Leu His Leu Gly Lys Cys Asn Ile Ala Gly Trp Ile Leu Gly Asn
     50                  55                  60

Pro Glu Cys Glu Ser Leu Ser Thr Ala Ser Ser Trp Ser Tyr Ile Val
 65                  70                  75                  80

Glu Thr Pro Ser Ser Asp Asn Gly Thr Cys Tyr Pro Gly Asp Phe Ile
                 85                  90                  95

Asp Tyr Glu Glu Leu Arg Glu Gln Leu Ser Ser Val Ser Ser Phe Glu
            100                 105                 110

Arg Phe Glu Ile Phe Pro Lys Thr Ser Ser Trp Pro Asn His Asp Ser
        115                 120                 125

Asn Lys Gly Val Thr Ala Ala Cys Pro His Ala Gly Ala Lys Ser Phe
    130                 135                 140

Tyr Lys Asn Leu Ile Trp Leu Val Lys Lys Gly Asn Ser Tyr Pro Lys
145                 150                 155                 160

Leu Ser Lys Ser Tyr Ile Asn Asp Lys Gly Lys Glu Val Leu Val Leu
                165                 170                 175

Trp Gly Ile His His Pro Ser Thr Ser Ala Asp Gln Gln Ser Leu Tyr
            180                 185                 190

Gln Asn Ala Asp Thr Tyr Val Phe Val Gly Ser Ser Arg Tyr Ser Lys
        195                 200                 205

Lys Phe Lys Pro Glu Ile Ala Ile Arg Pro Lys Val Arg Asp Gln Glu
    210                 215                 220

Gly Arg Met Asn Tyr Tyr Trp Thr Leu Val Glu Pro Gly Asp Lys Ile
225                 230                 235                 240

Thr Phe Glu Ala Thr Gly Asn Leu Val Val Pro Arg Tyr Ala Phe Ala
                245                 250                 255
```

```
Met Glu Arg Asn Ala Gly Ser Gly Ile Ile Ser Asp Thr Pro Val
            260                 265                 270

His Asp Cys Asn Thr Thr Cys Gln Thr Pro Lys Gly Ala Ile Asn Thr
275                 280                 285

Ser Leu Pro Phe Gln Asn Ile His Pro Ile Thr Ile Gly Lys Cys Pro
290                 295                 300

Lys Tyr Val Lys Ser Thr Lys Leu Arg Leu Ala Thr Gly Leu Arg Asn
305                 310                 315                 320

Ile Pro Ser Ile Gln Ser Arg Gly Leu Phe Gly Ala Ile Ala Gly Phe
                325                 330                 335

Ile Glu Gly Gly Trp Thr Gly Met Val Asp Gly Trp Tyr Gly Tyr His
            340                 345                 350

His Gln Asn Glu Gln Gly Ser Gly Tyr Ala Ala Asp Leu Lys Ser Thr
        355                 360                 365

Gln Asn Ala Ile Asp Glu Ile Thr Asn Lys Val Asn Ser Val Ile Glu
    370                 375                 380

Lys Met Asn Thr Gln Phe Thr Ala Val Gly Lys Glu Phe Asn His Leu
385                 390                 395                 400

Glu Lys Arg Ile Glu Asn Leu Asn Lys Lys Val Asp Asp Gly Phe Leu
                405                 410                 415

Asp Ile Trp Thr Tyr Asn Ala Glu Leu Leu Val Leu Leu Glu Asn Glu
            420                 425                 430

Arg Thr Leu Asp Tyr His Asp Ser Asn Val Lys Asn Leu Tyr Glu Lys
        435                 440                 445

Val Arg Ser Gln Leu Lys Asn Asn Ala Lys Glu Ile Gly Asn Gly Cys
    450                 455                 460

Phe Glu Phe Tyr His Lys Cys Asp Asn Thr Cys Met Glu Ser Val Lys
465                 470                 475                 480

<210> SEQ ID NO 2
<211> LENGTH: 320
<212> TYPE: PRT
<213> ORGANISM: Influenza A virus
<220> FEATURE:
<223> OTHER INFORMATION: Influenza A/Vietnam/1203/2004(H5N1)
      hemagglutinin HA1-320 domain

<400> SEQUENCE: 2

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Lys His Asn Gly Lys Leu Cys Asp Leu Asp Gly Val Lys
        35                  40                  45

Pro Leu Ile Leu Arg Asp Cys Ser Val Ala Gly Trp Leu Leu Gly Asn
    50                  55                  60

Pro Met Cys Asp Glu Phe Ile Asn Val Pro Glu Trp Ser Tyr Ile Val
65                  70                  75                  80

Glu Lys Ala Asn Pro Val Asn Asp Leu Cys Tyr Pro Gly Asp Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Ser Ser His Glu Ala Ser
        115                 120                 125

Leu Gly Val Ser Ser Ala Cys Pro Tyr Gln Gly Lys Ser Ser Phe Phe
    130                 135                 140
```

Arg Asn Val Val Trp Leu Ile Lys Lys Asn Ser Thr Tyr Pro Thr Ile
145                 150                 155                 160

Lys Arg Ser Tyr Asn Asn Thr Asn Gln Glu Asp Leu Leu Val Leu Trp
                165                 170                 175

Gly Ile His His Pro Asn Asp Ala Ala Glu Gln Thr Lys Leu Tyr Gln
            180                 185                 190

Asn Pro Thr Thr Tyr Ile Ser Val Gly Thr Ser Thr Leu Asn Gln Arg
            195                 200                 205

Leu Val Pro Arg Ile Ala Thr Arg Ser Lys Val Asn Gly Gln Ser Gly
        210                 215                 220

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Thr Ile Met Lys Ser Glu Leu Glu Tyr Gly
            260                 265                 270

Asn Cys Asn Thr Lys Cys Gln Thr Pro Met Gly Ala Ile Asn Ser Ser
            275                 280                 285

Met Pro Phe His Asn Ile His Pro Leu Thr Ile Gly Glu Cys Pro Lys
        290                 295                 300

Tyr Val Lys Ser Asn Arg Leu Val Leu Ala Thr Gly Leu Arg Asn Ser
305                 310                 315                 320

<210> SEQ ID NO 3
<211> LENGTH: 327
<212> TYPE: PRT
<213> ORGANISM: Influenza A virus
<220> FEATURE:
<223> OTHER INFORMATION: Influenza A/California/04/2009(H1N1)
      hemagglutinin HA1-330 domain

<400> SEQUENCE: 3

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Lys His Asn Gly Lys Leu Cys Lys Leu Arg Gly Val Ala
        35                  40                  45

Pro Leu His Leu Gly Lys Cys Asn Ile Ala Gly Trp Ile Leu Gly Asn
    50                  55                  60

Pro Glu Cys Glu Ser Leu Ser Thr Ala Ser Ser Trp Ser Tyr Ile Val
65                  70                  75                  80

Glu Thr Pro Ser Ser Asp Asn Gly Thr Cys Tyr Pro Gly Asp Phe Ile
                85                  90                  95

Asp Tyr Glu Glu Leu Arg Glu Gln Leu Ser Ser Val Ser Ser Phe Glu
            100                 105                 110

Arg Phe Glu Ile Phe Pro Lys Thr Ser Ser Trp Pro Asn His Asp Ser
        115                 120                 125

Asn Lys Gly Val Thr Ala Ala Cys Pro His Ala Gly Ala Lys Ser Phe
    130                 135                 140

Tyr Lys Asn Leu Ile Trp Leu Val Lys Lys Gly Asn Ser Tyr Pro Lys
145                 150                 155                 160

Leu Ser Lys Ser Tyr Ile Asn Asp Lys Gly Lys Glu Val Leu Val Leu
                165                 170                 175

Trp Gly Ile His His Pro Ser Thr Ser Ala Asp Gln Gln Ser Leu Tyr

```
            180                 185                 190
Gln Asn Ala Asp Thr Tyr Val Phe Val Gly Ser Ser Arg Tyr Ser Lys
            195                 200                 205

Lys Phe Lys Pro Glu Ile Ala Ile Arg Pro Lys Val Arg Asp Gln Glu
            210                 215                 220

Gly Arg Met Asn Tyr Tyr Trp Thr Leu Val Glu Pro Gly Asp Lys Ile
225                 230                 235                 240

Thr Phe Glu Ala Thr Gly Asn Leu Val Val Pro Arg Tyr Ala Phe Ala
            245                 250                 255

Met Glu Arg Asn Ala Gly Ser Gly Ile Ile Ile Ser Asp Thr Pro Val
            260                 265                 270

His Asp Cys Asn Thr Thr Cys Gln Thr Pro Lys Gly Ala Ile Asn Thr
            275                 280                 285

Ser Leu Pro Phe Gln Asn Ile His Pro Ile Thr Ile Gly Lys Cys Pro
            290                 295                 300

Lys Tyr Val Lys Ser Thr Lys Leu Arg Leu Ala Thr Gly Leu Arg Asn
305                 310                 315                 320

Ile Pro Ser Ile Gln Ser Arg
                325

<210> SEQ ID NO 4
<211> LENGTH: 320
<212> TYPE: PRT
<213> ORGANISM: Influenza A virus
<220> FEATURE:
<223> OTHER INFORMATION: Influenza A/Indonesia/5/2005(H5N1)
      hemagglutinin HA1-320 domain

<400> SEQUENCE: 4

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Thr His Asn Gly Lys Leu Cys Asp Leu Asp Gly Val Lys
        35                  40                  45

Pro Leu Ile Leu Arg Asp Cys Ser Val Ala Gly Trp Leu Leu Gly Asn
    50                  55                  60

Pro Met Cys Asp Glu Phe Ile Asn Val Pro Glu Trp Ser Tyr Ile Val
65                  70                  75                  80

Glu Lys Ala Asn Pro Thr Asn Asp Leu Cys Tyr Pro Gly Ser Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Ser Asp His Glu Ala Ser
        115                 120                 125

Ser Gly Val Ser Ser Ala Cys Pro Tyr Leu Gly Ser Pro Ser Phe Phe
    130                 135                 140

Arg Asn Val Val Trp Leu Ile Lys Lys Asn Ser Thr Tyr Pro Thr Ile
145                 150                 155                 160

Lys Lys Ser Tyr Asn Asn Thr Asn Gln Glu Asp Leu Leu Val Leu Trp
                165                 170                 175

Gly Ile His His Pro Asn Asp Ala Ala Glu Gln Thr Arg Leu Tyr Gln
            180                 185                 190

Asn Pro Thr Thr Tyr Ile Ser Ile Gly Thr Ser Thr Leu Asn Gln Arg
        195                 200                 205
```

Leu Val Pro Lys Ile Ala Thr Arg Ser Lys Val Asn Gly Gln Ser Gly
210                 215                 220

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Ala Ile Met Lys Ser Glu Leu Glu Tyr Gly
                260                 265                 270

Asn Cys Asn Thr Lys Cys Gln Thr Pro Met Gly Ala Ile Asn Ser Ser
                275                 280                 285

Met Pro Phe His Asn Ile His Pro Leu Thr Ile Gly Glu Cys Pro Lys
290                 295                 300

Tyr Val Lys Ser Asn Arg Leu Val Leu Ala Thr Gly Leu Arg Asn Ser
305                 310                 315                 320

<210> SEQ ID NO 5
<211> LENGTH: 326
<212> TYPE: PRT
<213> ORGANISM: Influenza A virus
<220> FEATURE:
<223> OTHER INFORMATION: Influenza A/Victoria/210/2009(H3N2)
      hemagglutinin HA1-330 domain

<400> SEQUENCE: 5

Ser Trp Asn Asp Asn Ser Thr Ala Thr Leu Cys Leu Gly His His Ala
1               5                   10                  15

Val Pro Asn Gly Thr Ile Val Lys Thr Ile Thr Asn Asp Gln Ile Glu
                20                  25                  30

Val Thr Asn Ala Thr Glu Leu Val Gln Asn Ser Ser Thr Gly Glu Ile
            35                  40                  45

Cys Asp Ser Pro His Gln Ile Leu Asp Gly Lys Asn Cys Thr Leu Ile
50                  55                  60

Asp Ala Leu Leu Gly Asp Pro Gln Cys Asp Gly Phe Gln Asn Lys Lys
65                  70                  75                  80

Trp Asp Leu Phe Val Glu Arg Ser Lys Ala Tyr Ser Asn Cys Tyr Pro
                85                  90                  95

Tyr Asp Val Pro Asp Tyr Ala Ser Leu Arg Ser Leu Val Ala Ser Ser
                100                 105                 110

Gly Thr Leu Glu Phe Asn Asn Glu Ser Phe Asn Trp Thr Gly Val Thr
            115                 120                 125

Gln Asn Gly Thr Ser Ser Ala Cys Ile Arg Arg Ser Lys Asn Ser Phe
130                 135                 140

Phe Ser Arg Leu Asn Trp Leu Thr His Leu Asn Phe Lys Tyr Pro Ala
145                 150                 155                 160

Leu Asn Val Thr Met Pro Asn Asn Glu Gln Phe Asp Lys Leu Tyr Ile
                165                 170                 175

Trp Gly Val His His Pro Val Thr Asp Lys Asp Gln Ile Phe Leu Tyr
                180                 185                 190

Ala Gln Ala Ser Gly Arg Ile Thr Val Ser Thr Lys Arg Ser Gln Gln
            195                 200                 205

Thr Val Ile Pro Asn Ile Gly Ser Arg Pro Arg Val Arg Asn Ile Pro
210                 215                 220

Thr Arg Ile Ser Ile Tyr Trp Thr Ile Val Lys Pro Gly Asp Ile Leu
225                 230                 235                 240

Leu Ile Asn Ser Thr Gly Asn Leu Ile Ala Pro Arg Gly Tyr Phe Lys
                245                 250                 255

```
Met Gln Ser Gly Lys Ser Ser Ile Met Arg Ser Asp Ala Pro Ile Gly
            260                 265                 270

Lys Cys Asn Ser Glu Cys Ile Thr Pro Asn Gly Ser Ile Pro Asn Asp
        275                 280                 285

Lys Pro Phe Gln Asn Val Asn Arg Ile Thr Tyr Gly Ala Cys Pro Arg
    290                 295                 300

Tyr Val Lys Gln Asn Thr Leu Lys Leu Ala Thr Gly Met Arg Asn Val
305                 310                 315                 320

Pro Glu Lys Gln Thr Arg
                325

<210> SEQ ID NO 6
<211> LENGTH: 326
<212> TYPE: PRT
<213> ORGANISM: Influenza A virus
<220> FEATURE:
<223> OTHER INFORMATION: Influenza A/Wisconsin/15/2009(H3N2)
      hemagglutinin HA1-330 domain

<400> SEQUENCE: 6

Ser Trp Asn Asp Asn Ser Thr Ala Thr Leu Cys Leu Gly His His Ala
1               5                   10                  15

Val Pro Asn Gly Thr Ile Val Lys Thr Ile Thr Asn Asp Gln Ile Glu
            20                  25                  30

Val Thr Asn Ala Thr Glu Leu Val Gln Ser Ser Ser Thr Gly Glu Ile
        35                  40                  45

Cys Asp Ser Pro His Gln Ile Leu Asp Gly Lys Asn Cys Thr Leu Ile
50                  55                  60

Asp Ala Leu Leu Gly Asp Pro Gln Cys Asp Asp Phe Gln Asn Lys Lys
65                  70                  75                  80

Trp Asp Leu Phe Val Glu Arg Ser Lys Ala Tyr Ser Asn Cys Tyr Pro
                85                  90                  95

Tyr Asp Val Pro Asp Tyr Ala Ser Leu Arg Ser Leu Val Ala Ser Ser
            100                 105                 110

Gly Thr Leu Glu Phe Asn Asn Glu Ser Phe Asn Trp Thr Gly Val Thr
        115                 120                 125

Gln Asn Gly Thr Ser Ser Ala Cys Ile Arg Arg Ser Lys Asn Ser Phe
    130                 135                 140

Phe Ser Arg Leu Asn Trp Leu Thr His Leu Asn Phe Lys Tyr Pro Ala
145                 150                 155                 160

Leu Asn Val Thr Met Pro Asn Asn Glu Gln Phe Asp Lys Leu Tyr Ile
                165                 170                 175

Trp Gly Val His His Pro Gly Thr Asp Lys Asp Gln Ile Phe Pro Tyr
            180                 185                 190

Ala Gln Ala Ser Gly Arg Ile Thr Val Ser Thr Lys Arg Ser Gln Gln
        195                 200                 205

Thr Ala Ile Pro Asn Ile Gly Ser Arg Pro Arg Val Arg Asn Ile Pro
    210                 215                 220

Ser Arg Ile Ser Ile Tyr Trp Thr Ile Val Lys Pro Gly Asp Ile Leu
225                 230                 235                 240

Leu Ile Asn Ser Thr Gly Asn Leu Ile Ala Pro Arg Gly Tyr Phe Lys
                245                 250                 255

Ile Arg Ser Gly Lys Ser Ser Ile Met Arg Ser Asp Ala Pro Ile Gly
            260                 265                 270

Lys Cys Asn Ser Glu Cys Ile Thr Pro Asn Gly Ser Ile Pro Asn Asp
```

```
                275                 280                 285
Lys Pro Phe Gln Asn Val Asn Arg Ile Thr Tyr Gly Ala Cys Pro Arg
    290                 295                 300

Tyr Val Lys Gln Asn Thr Leu Lys Leu Ala Thr Gly Met Arg Asn Val
305                 310                 315                 320

Pro Glu Lys Gln Thr Arg
                325

<210> SEQ ID NO 7
<211> LENGTH: 314
<212> TYPE: PRT
<213> ORGANISM: Influenza A virus
<220> FEATURE:
<223> OTHER INFORMATION: Influenza A/Netherlands/219/03(H7N7)
      hemagglutinin HA1-320 domain

<400> SEQUENCE: 7

Asp Lys Ile Cys Leu Gly His His Ala Val Ser Asn Gly Thr Lys Val
1               5                   10                  15

Asn Thr Leu Thr Glu Arg Gly Val Glu Val Val Asn Ala Thr Glu Thr
            20                  25                  30

Val Glu Arg Thr Asn Val Pro Arg Ile Cys Ser Lys Gly Lys Arg Thr
        35                  40                  45

Val Asp Leu Gly Gln Cys Gly Leu Leu Gly Thr Ile Thr Gly Pro Pro
    50                  55                  60

Gln Cys Asp Gln Phe Leu Glu Phe Ser Ala Asp Leu Ile Ile Glu Arg
65                  70                  75                  80

Arg Glu Gly Ser Asp Val Cys Tyr Pro Gly Lys Phe Val Asn Glu Glu
                85                  90                  95

Ala Leu Arg Gln Ile Leu Arg Glu Ser Gly Gly Ile Asp Lys Glu Thr
            100                 105                 110

Met Gly Phe Thr Tyr Ser Gly Ile Arg Thr Asn Gly Thr Thr Ser Ala
        115                 120                 125

Cys Arg Arg Ser Gly Ser Ser Phe Tyr Ala Glu Met Lys Trp Leu Leu
    130                 135                 140

Ser Asn Thr Asp Asn Ala Ala Phe Pro Gln Met Thr Lys Ser Tyr Lys
145                 150                 155                 160

Asn Thr Arg Lys Asp Pro Ala Leu Ile Ile Trp Gly Ile His His Ser
                165                 170                 175

Gly Ser Thr Thr Glu Gln Thr Lys Leu Tyr Gly Ser Gly Asn Lys Leu
            180                 185                 190

Ile Thr Val Gly Ser Ser Asn Tyr Gln Gln Ser Phe Val Pro Ser Pro
        195                 200                 205

Gly Ala Arg Pro Gln Val Asn Gly Gln Ser Gly Arg Ile Asp Phe His
    210                 215                 220

Trp Leu Ile Leu Asn Pro Asn Asp Thr Val Thr Phe Ser Phe Asn Gly
225                 230                 235                 240

Ala Phe Ile Ala Pro Asp Arg Ala Ser Phe Leu Arg Gly Lys Ser Met
                245                 250                 255

Gly Ile Gln Ser Glu Val Gln Val Asp Ala Asn Cys Glu Gly Asp Cys
            260                 265                 270

Tyr His Ser Gly Gly Thr Ile Ile Ser Asn Leu Pro Phe Gln Asn Ile
        275                 280                 285

Asn Ser Arg Ala Val Gly Lys Cys Pro Arg Tyr Val Lys Gln Glu Ser
    290                 295                 300
```

-continued

Leu Leu Leu Ala Thr Gly Met Lys Asn Val
305                 310

<210> SEQ ID NO 8
<211> LENGTH: 481
<212> TYPE: PRT
<213> ORGANISM: Influenza A virus
<220> FEATURE:
<223> OTHER INFORMATION: Influenza A/Indonesia/5/2005{H5N1}
      hemagglutinin HA1-480 domain

<400> SEQUENCE: 8

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Thr His Asn Gly Lys Leu Cys Asp Leu Asp Gly Val Lys
        35                  40                  45

Pro Leu Ile Leu Arg Asp Cys Ser Val Ala Gly Trp Leu Leu Gly Asn
50                  55                  60

Pro Met Cys Asp Glu Phe Ile Asn Val Pro Glu Trp Ser Tyr Ile Val
65                  70                  75                  80

Glu Lys Ala Asn Pro Thr Asn Asp Leu Cys Tyr Pro Gly Ser Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Ser Asp His Glu Ala Ser
        115                 120                 125

Ser Gly Val Ser Ser Ala Cys Pro Tyr Leu Gly Ser Pro Ser Phe Phe
130                 135                 140

Arg Asn Val Val Trp Leu Ile Lys Lys Asn Ser Thr Tyr Pro Thr Ile
145                 150                 155                 160

Lys Lys Ser Tyr Asn Asn Thr Asn Gln Glu Asp Leu Leu Val Leu Trp
                165                 170                 175

Gly Ile His His Pro Asn Asp Ala Ala Glu Gln Thr Arg Leu Tyr Gln
            180                 185                 190

Asn Pro Thr Thr Tyr Ile Ser Ile Gly Thr Ser Thr Leu Asn Gln Arg
        195                 200                 205

Leu Val Pro Lys Ile Ala Thr Arg Ser Lys Val Asn Gly Gln Ser Gly
210                 215                 220

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Ala Ile Met Lys Ser Glu Leu Glu Tyr Gly
            260                 265                 270

Asn Cys Asn Thr Lys Cys Gln Thr Pro Met Gly Ala Ile Asn Ser Ser
        275                 280                 285

Met Pro Phe His Asn Ile His Pro Leu Thr Ile Gly Glu Cys Pro Lys
290                 295                 300

Tyr Val Lys Ser Asn Arg Leu Val Leu Ala Thr Gly Leu Arg Asn Ser
305                 310                 315                 320

Pro Gln Arg Glu Ser Arg Arg Lys Lys Arg Gly Leu Phe Gly Ala Ile
                325                 330                 335

Ala Gly Phe Ile Glu Gly Gly Trp Gln Gly Met Val Asp Gly Trp Tyr
            340                 345                 350

```
Gly Tyr His His Ser Asn Glu Gln Gly Ser Gly Tyr Ala Ala Asp Lys
            355                 360                 365

Glu Ser Thr Gln Lys Ala Ile Asp Gly Val Thr Asn Lys Val Asn Ser
        370                 375                 380

Ile Ile Asp Lys Met Asn Thr Gln Phe Glu Ala Val Gly Arg Glu Phe
385                 390                 395                 400

Asn Asn Leu Glu Arg Arg Ile Glu Asn Leu Asn Lys Lys Met Glu Asp
                405                 410                 415

Gly Phe Leu Asp Val Trp Thr Tyr Asn Ala Glu Leu Leu Val Leu Met
                420                 425                 430

Glu Asn Glu Arg Thr Leu Asp Phe His Asp Ser Asn Val Lys Asn Leu
            435                 440                 445

Tyr Asp Lys Val Arg Leu Gln Leu Arg Asp Asn Ala Lys Glu Leu Gly
        450                 455                 460

Asn Gly Cys Phe Glu Phe Tyr His Lys Cys Asp Asn Glu Cys Met Glu
465                 470                 475                 480

Ser
```

```
<210> SEQ ID NO 9
<211> LENGTH: 481
<212> TYPE: PRT
<213> ORGANISM: Influenza A virus
<220> FEATURE:
<223> OTHER INFORMATION: Influenza A/Viet Nam/1203/2004{H5N1}
      hemagglutinin HA1-480 domain

<400> SEQUENCE: 9

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Lys His Asn Gly Lys Leu Cys Asp Leu Asp Gly Val Lys
        35                  40                  45

Pro Leu Ile Leu Arg Asp Cys Ser Val Ala Gly Trp Leu Leu Gly Asn
50                  55                  60

Pro Met Cys Asp Glu Phe Ile Asn Val Pro Glu Trp Ser Tyr Ile Val
65                  70                  75                  80

Glu Lys Ala Asn Pro Val Asn Asp Leu Cys Tyr Pro Gly Asp Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Ser Ser His Glu Ala Ser
        115                 120                 125

Leu Gly Val Ser Ser Ala Cys Pro Tyr Gln Gly Lys Ser Ser Phe Phe
    130                 135                 140

Arg Asn Val Val Trp Leu Ile Lys Lys Asn Ser Thr Tyr Pro Thr Ile
145                 150                 155                 160

Lys Arg Ser Tyr Asn Asn Thr Asn Gln Glu Asp Leu Leu Val Leu Trp
                165                 170                 175

Gly Ile His His Pro Asn Asp Ala Ala Glu Gln Thr Lys Leu Tyr Gln
            180                 185                 190

Asn Pro Thr Thr Tyr Ile Ser Val Gly Thr Ser Thr Leu Asn Gln Arg
        195                 200                 205

Leu Val Pro Arg Ile Ala Thr Arg Ser Lys Val Asn Gly Gln Ser Gly
    210                 215                 220
```

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
            245                 250                 255

Val Lys Lys Gly Asp Ser Thr Ile Met Lys Ser Glu Leu Glu Tyr Gly
            260                 265                 270

Asn Cys Asn Thr Lys Cys Gln Thr Pro Met Gly Ala Ile Asn Ser Ser
            275                 280                 285

Met Pro Phe His Asn Ile His Pro Leu Thr Ile Gly Glu Cys Pro Lys
            290                 295                 300

Tyr Val Lys Ser Asn Arg Leu Val Leu Ala Thr Gly Leu Arg Asn Ser
305                 310                 315                 320

Pro Gln Arg Glu Arg Arg Arg Lys Lys Arg Gly Leu Phe Gly Ala Ile
            325                 330                 335

Ala Gly Phe Ile Glu Gly Gly Trp Gln Gly Met Val Asp Gly Trp Tyr
            340                 345                 350

Gly Tyr His His Ser Asn Glu Gln Gly Ser Gly Tyr Ala Ala Asp Lys
            355                 360                 365

Glu Ser Thr Gln Lys Ala Ile Asp Gly Val Thr Asn Lys Val Asn Ser
370                 375                 380

Ile Ile Asp Lys Met Asn Thr Gln Phe Glu Ala Val Gly Arg Glu Phe
385                 390                 395                 400

Asn Asn Leu Glu Arg Arg Ile Glu Asn Leu Asn Lys Lys Met Glu Asp
            405                 410                 415

Gly Phe Leu Asp Val Trp Thr Tyr Asn Ala Glu Leu Leu Val Leu Met
            420                 425                 430

Glu Asn Glu Arg Thr Leu Asp Phe His Asp Ser Asn Val Lys Asn Leu
            435                 440                 445

Tyr Asp Lys Val Arg Leu Gln Leu Arg Asp Asn Ala Lys Glu Leu Gly
            450                 455                 460

Asn Gly Cys Phe Glu Phe Tyr His Lys Cys Asp Asn Glu Cys Met Glu
465                 470                 475                 480

Ser

<210> SEQ ID NO 10
<211> LENGTH: 478
<212> TYPE: PRT
<213> ORGANISM: Influenza A virus
<220> FEATURE:
<223> OTHER INFORMATION: Influenza A/California/04/2009{H1N1}
      hemagglutinin HA1-480 domain

<400> SEQUENCE: 10

Asp Thr Leu Cys Ile Gly Tyr His Ala Asn Asn Ser Thr Asp Thr Val
 1               5                  10                  15

Asp Thr Val Leu Glu Lys Asn Val Thr Val Thr His Ser Val Asn Leu
            20                  25                  30

Leu Glu Asp Lys His Asn Gly Lys Leu Cys Lys Leu Arg Gly Val Ala
        35                  40                  45

Pro Leu His Leu Gly Lys Cys Asn Ile Ala Gly Trp Ile Leu Gly Asn
    50                  55                  60

Pro Glu Cys Glu Ser Leu Ser Thr Ala Ser Ser Trp Ser Tyr Ile Val
65                  70                  75                  80

Glu Thr Pro Ser Ser Asp Asn Gly Thr Cys Tyr Pro Gly Asp Phe Ile
            85                  90                  95

```
Asp Tyr Glu Glu Leu Arg Glu Gln Leu Ser Ser Val Ser Ser Phe Glu
            100                 105                 110

Arg Phe Glu Ile Phe Pro Lys Thr Ser Ser Trp Pro Asn His Asp Ser
        115                 120                 125

Asn Lys Gly Val Thr Ala Ala Cys Pro His Ala Gly Ala Lys Ser Phe
    130                 135                 140

Tyr Lys Asn Leu Ile Trp Leu Val Lys Gly Asn Ser Tyr Pro Lys
145                 150                 155                 160

Leu Ser Lys Ser Tyr Ile Asn Asp Lys Gly Lys Glu Val Leu Val Leu
                165                 170                 175

Trp Gly Ile His His Pro Ser Thr Ser Ala Asp Gln Gln Ser Leu Tyr
                180                 185                 190

Gln Asn Ala Asp Thr Tyr Val Phe Val Gly Ser Ser Arg Tyr Ser Lys
            195                 200                 205

Lys Phe Lys Pro Glu Ile Ala Ile Arg Pro Lys Val Arg Asp Gln Glu
        210                 215                 220

Gly Arg Met Asn Tyr Tyr Trp Thr Leu Val Glu Pro Gly Asp Lys Ile
225                 230                 235                 240

Thr Phe Glu Ala Thr Gly Asn Leu Val Val Pro Arg Tyr Ala Phe Ala
                245                 250                 255

Met Glu Arg Asn Ala Gly Ser Gly Ile Ile Ile Ser Asp Thr Pro Val
            260                 265                 270

His Asp Cys Asn Thr Thr Cys Gln Thr Pro Lys Gly Ala Ile Asn Thr
        275                 280                 285

Ser Leu Pro Phe Gln Asn Ile His Pro Ile Thr Ile Gly Lys Cys Pro
    290                 295                 300

Lys Tyr Val Lys Ser Thr Lys Leu Arg Leu Ala Thr Gly Leu Arg Asn
305                 310                 315                 320

Ile Pro Ser Ile Gln Ser Arg Gly Leu Phe Gly Ala Ile Ala Gly Phe
                325                 330                 335

Ile Glu Gly Gly Trp Thr Gly Met Val Asp Gly Trp Tyr Gly Tyr His
            340                 345                 350

His Gln Asn Glu Gln Gly Ser Gly Tyr Ala Ala Asp Leu Lys Ser Thr
        355                 360                 365

Gln Asn Ala Ile Asp Glu Ile Thr Asn Lys Val Asn Ser Val Ile Glu
    370                 375                 380

Lys Met Asn Thr Gln Phe Thr Ala Val Gly Lys Glu Phe Asn His Leu
385                 390                 395                 400

Glu Lys Arg Ile Glu Asn Leu Asn Lys Lys Val Asp Asp Gly Phe Leu
                405                 410                 415

Asp Ile Trp Thr Tyr Asn Ala Glu Leu Leu Val Leu Leu Glu Asn Glu
            420                 425                 430

Arg Thr Leu Asp Tyr His Asp Ser Asn Val Lys Asn Leu Tyr Glu Lys
        435                 440                 445

Val Arg Ser Gln Leu Lys Asn Asn Ala Lys Glu Ile Gly Asn Gly Cys
    450                 455                 460

Phe Glu Phe Tyr His Lys Cys Asp Asn Thr Cys Met Glu Ser
465                 470                 475

<210> SEQ ID NO 11
<211> LENGTH: 477
<212> TYPE: PRT
<213> ORGANISM: Influenza A virus
<220> FEATURE:
```

<223> OTHER INFORMATION: Influenza A/New Caledonia/6/2008{H1N1}
hemagglutinin HA1-480 domain

<400> SEQUENCE: 11

```
Asp Thr Ile Cys Ile Gly Tyr His Ala Asn Asn Ser Thr Asp Thr Val
 1               5                   10                  15

Asp Thr Val Leu Glu Lys Asn Val Thr Val Thr His Ser Val Asn Leu
            20                  25                  30

Leu Glu Asn Ser His Asn Gly Lys Leu Cys Leu Leu Lys Gly Ile Ala
        35                  40                  45

Pro Leu Gln Leu Gly Asn Cys Ser Val Ala Gly Trp Ile Leu Gly Asn
50                  55                  60

Pro Glu Cys Glu Leu Leu Ile Ser Lys Glu Ser Trp Ser Tyr Ile Val
65                  70                  75                  80

Glu Lys Pro Asn Pro Glu Asn Gly Thr Cys Tyr Pro Gly His Phe Ala
                85                  90                  95

Asp Tyr Glu Glu Leu Arg Glu Gln Leu Ser Ser Val Ser Ser Phe Glu
            100                 105                 110

Arg Phe Glu Ile Phe Pro Lys Glu Ser Ser Trp Pro Asn His Thr Val
        115                 120                 125

Thr Gly Val Ser Ala Ser Cys Ser His Asn Gly Glu Ser Ser Phe Tyr
130                 135                 140

Arg Asn Leu Leu Trp Leu Thr Gly Lys Asn Gly Leu Tyr Pro Asn Leu
145                 150                 155                 160

Ser Lys Ser Tyr Ala Asn Asn Lys Glu Lys Glu Val Leu Val Leu Trp
                165                 170                 175

Gly Val His His Pro Pro Ser Ile Asn Asp Gln Lys Thr Leu Tyr His
            180                 185                 190

Thr Glu Asn Ala Tyr Val Ser Val Val Phe Ser His Tyr Ser Arg Lys
        195                 200                 205

Phe Thr Pro Glu Ile Ala Lys Arg Pro Lys Val Arg Asp Gln Glu Gly
210                 215                 220

Arg Ile Asn Tyr Tyr Trp Thr Leu Leu Glu Pro Gly Asp Thr Ile Ile
225                 230                 235                 240

Phe Glu Ala Asn Gly Asn Leu Ile Ala Pro Arg Tyr Ala Phe Ala Leu
                245                 250                 255

Ser Arg Gly Phe Gly Ser Gly Ile Ile Asn Ser Asn Ala Pro Met Asp
            260                 265                 270

Lys Cys Asp Ala Lys Cys Gln Thr Pro Gln Gly Ala Ile Asn Ser Ser
        275                 280                 285

Leu Pro Phe Gln Asn Val His Pro Val Thr Ile Gly Glu Cys Pro Lys
290                 295                 300

Tyr Val Arg Ser Ala Lys Leu Arg Met Val Thr Gly Leu Arg Asn Ile
305                 310                 315                 320

Pro Ser Ile Gln Ser Arg Gly Leu Phe Gly Ala Ile Ala Gly Phe Ile
                325                 330                 335

Glu Gly Gly Trp Thr Gly Met Val Asp Gly Trp Tyr Gly Tyr His His
            340                 345                 350

Gln Asn Glu Gln Gly Ser Gly Tyr Ala Ala Asp Gln Lys Ser Thr Gln
        355                 360                 365

Asn Ala Ile Asn Gly Ile Thr Asn Lys Val Asn Ser Val Ile Glu Lys
370                 375                 380

Met Asn Thr Gln Phe Thr Ala Val Gly Lys Glu Phe Asn Lys Leu Glu
385                 390                 395                 400
```

Arg Arg Met Glu Asn Leu Asn Lys Lys Val Asp Asp Gly Phe Ile Asp
            405                 410                 415

Ile Trp Thr Tyr Asn Ala Glu Leu Leu Val Leu Leu Glu Asn Glu Arg
            420                 425                 430

Thr Leu Asp Phe His Asp Ser Asn Val Lys Asn Leu Tyr Glu Lys Val
            435                 440                 445

Lys Ser Gln Leu Lys Asn Asn Ala Lys Glu Ile Gly Asn Gly Cys Phe
            450                 455                 460

Glu Phe Tyr His Lys Cys Asn Asp Glu Cys Met Glu Ser
465                 470                 475

<210> SEQ ID NO 12
<211> LENGTH: 478
<212> TYPE: PRT
<213> ORGANISM: Influenza A virus
<220> FEATURE:
<223> OTHER INFORMATION: Influenza A/South Carolina/1/18{H1N1}
      hemagglutinin HA1-480 domain

<400> SEQUENCE: 12

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Ser His Asn Gly Lys Leu Cys Lys Leu Lys Gly Ile Ala
            35                  40                  45

Pro Leu Gln Leu Gly Lys Cys Asn Ile Ala Gly Trp Leu Leu Gly Asn
            50                  55                  60

Pro Glu Cys Asp Leu Leu Leu Thr Ala Ser Ser Trp Ser Tyr Ile Val
65                  70                  75                  80

Glu Thr Ser Asn Ser Glu Asn Gly Thr Cys Tyr Pro Gly Asp Phe Ile
                85                  90                  95

Asp Tyr Glu Glu Leu Arg Glu Gln Leu Ser Ser Val Ser Ser Phe Glu
            100                 105                 110

Lys Phe Glu Ile Phe Pro Lys Thr Ser Ser Trp Pro Asn His Glu Thr
            115                 120                 125

Thr Lys Gly Val Thr Ala Ala Cys Ser Tyr Ala Gly Ala Ser Ser Phe
            130                 135                 140

Tyr Arg Asn Leu Leu Trp Leu Thr Lys Lys Gly Ser Ser Tyr Pro Lys
145                 150                 155                 160

Leu Ser Lys Ser Tyr Val Asn Asn Lys Gly Lys Glu Val Leu Val Leu
                165                 170                 175

Trp Gly Val His His Pro Pro Thr Gly Thr Asp Gln Gln Ser Leu Tyr
            180                 185                 190

Gln Asn Ala Asp Ala Tyr Val Ser Val Gly Ser Ser Lys Tyr Asn Arg
            195                 200                 205

Arg Phe Thr Pro Glu Ile Ala Ala Arg Pro Lys Val Arg Asp Gln Ala
            210                 215                 220

Gly Arg Met Asn Tyr Tyr Trp Thr Leu Leu Glu Pro Gly Asp Thr Ile
225                 230                 235                 240

Thr Phe Glu Ala Thr Gly Asn Leu Ile Ala Pro Trp Tyr Ala Phe Ala
                245                 250                 255

Leu Asn Arg Gly Ser Gly Ser Gly Ile Ile Thr Ser Asp Ala Pro Val
            260                 265                 270

His Asp Cys Asn Thr Lys Cys Gln Thr Pro His Gly Ala Ile Asn Ser

```
            275                 280                 285
Ser Leu Pro Phe Gln Asn Ile His Pro Val Thr Ile Gly Glu Cys Pro
290                 295                 300

Lys Tyr Val Arg Ser Thr Lys Leu Arg Met Ala Thr Gly Leu Arg Asn
305                 310                 315                 320

Ile Pro Ser Ile Gln Ser Arg Gly Leu Phe Gly Ala Ile Ala Gly Phe
                325                 330                 335

Ile Glu Gly Gly Trp Thr Gly Met Ile Asp Gly Trp Tyr Gly Tyr His
            340                 345                 350

His Gln Asn Glu Gln Gly Ser Gly Tyr Ala Ala Asp Gln Lys Ser Thr
        355                 360                 365

Gln Asn Ala Ile Asp Gly Ile Thr Asn Lys Val Asn Ser Val Ile Glu
370                 375                 380

Lys Met Asn Thr Gln Phe Thr Ala Val Gly Lys Glu Phe Asn Asn Leu
385                 390                 395                 400

Glu Arg Arg Ile Glu Asn Leu Asn Lys Lys Val Asp Asp Gly Phe Leu
                405                 410                 415

Asp Ile Trp Thr Tyr Asn Ala Glu Leu Leu Val Leu Leu Glu Asn Glu
            420                 425                 430

Arg Thr Leu Asp Phe His Asp Ser Asn Val Arg Asn Leu Tyr Glu Lys
        435                 440                 445

Val Lys Ser Gln Leu Lys Asn Asn Ala Lys Glu Ile Gly Asn Gly Cys
    450                 455                 460

Phe Glu Phe Tyr His Lys Cys Asp Asp Ala Cys Met Glu Ser
465                 470                 475

<210> SEQ ID NO 13
<211> LENGTH: 477
<212> TYPE: PRT
<213> ORGANISM: Influenza A virus
<220> FEATURE:
<223> OTHER INFORMATION: Influenza A/Denver/57{H1N1} hemagglutinin
      HA1-480 domain

<400> SEQUENCE: 13

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Ser His Asn Gly Lys Leu Cys Arg Leu Lys Gly Lys Ala
        35                  40                  45

Pro Leu Gln Leu Gly Asn Cys Asn Ile Ala Gly Trp Val Leu Gly Asn
50                  55                  60

Pro Glu Cys Glu Ser Leu Leu Ser Asn Arg Ser Trp Ser Tyr Ile Ala
65                  70                  75                  80

Glu Thr Pro Asn Ser Glu Asn Gly Thr Cys Tyr Pro Gly Asp Phe Ala
                85                  90                  95

Asp Tyr Glu Glu Leu Arg Glu Gln Leu Ser Ser Val Ser Ser Phe Glu
            100                 105                 110

Arg Phe Glu Ile Phe Pro Lys Glu Arg Ser Trp Pro Asn His Thr Thr
        115                 120                 125

Arg Gly Val Thr Ala Ala Cys Pro His Ala Arg Lys Ser Ser Phe Tyr
130                 135                 140

Lys Asn Leu Val Trp Leu Thr Glu Ala Asn Gly Ser Tyr Pro Asn Leu
145                 150                 155                 160
```

Ser Arg Ser Tyr Val Asn Asn Gln Glu Lys Glu Val Leu Val Leu Trp
            165                 170                 175

Gly Val His His Pro Ser Asn Ile Glu Glu Gln Arg Ala Leu Tyr Arg
        180                 185                 190

Lys Asp Asn Ala Tyr Val Ser Val Val Ser Ser Asn Tyr Asn Arg Arg
            195                 200                 205

Phe Thr Pro Glu Ile Ala Lys Arg Pro Lys Val Arg Asp Gln Ser Gly
        210                 215                 220

Arg Met Asn Tyr Tyr Trp Thr Leu Leu Glu Pro Gly Asp Thr Ile Ile
225                 230                 235                 240

Phe Glu Ala Thr Gly Asn Leu Ile Ala Pro Trp Tyr Ala Phe Ala Leu
                245                 250                 255

Ser Arg Gly Pro Gly Ser Gly Ile Ile Thr Ser Asn Ala Pro Leu Asp
            260                 265                 270

Glu Cys Asp Thr Lys Cys Gln Thr Pro Gln Gly Ala Ile Asn Ser Ser
        275                 280                 285

Leu Pro Phe Gln Asn Ile His Pro Val Thr Ile Gly Glu Cys Pro Lys
        290                 295                 300

Tyr Val Arg Ser Thr Lys Leu Arg Met Val Thr Gly Leu Arg Asn Ile
305                 310                 315                 320

Pro Ser Val Gln Ser Arg Gly Leu Phe Gly Ala Ile Ala Gly Phe Ile
                325                 330                 335

Glu Gly Gly Trp Thr Gly Met Met Asp Gly Trp Tyr Gly Tyr His His
            340                 345                 350

Gln Asn Glu Gln Gly Ser Gly Tyr Ala Ala Asp Gln Lys Ser Thr Gln
        355                 360                 365

Asn Ala Ile Asn Gly Ile Thr Asn Lys Val Asn Ser Val Ile Glu Lys
        370                 375                 380

Met Asn Thr Gln Phe Thr Ala Val Gly Lys Glu Phe Asn Lys Leu Glu
385                 390                 395                 400

Lys Arg Met Glu Asn Leu Asn Lys Lys Val Asp Asp Gly Phe Met Asp
                405                 410                 415

Ile Trp Thr Tyr Asn Ala Glu Leu Leu Val Leu Leu Glu Asn Glu Arg
            420                 425                 430

Thr Leu Asp Phe His Asp Ser Asn Val Lys Asn Leu Tyr Glu Lys Val
        435                 440                 445

Lys Asn Gln Leu Arg Asn Asn Ala Lys Glu Leu Gly Asn Gly Cys Phe
        450                 455                 460

Glu Phe Tyr His Lys Cys Asp Asn Glu Cys Met Glu Ser
465                 470                 475

<210> SEQ ID NO 14
<211> LENGTH: 478
<212> TYPE: PRT
<213> ORGANISM: Influenza A virus
<220> FEATURE:
<223> OTHER INFORMATION: Influenza A/swine/Wisconsin/1/1968{H1N1}
      hemagglutinin HA1-480 domain

<400> SEQUENCE: 14

Asp Thr Leu Cys Ile Gly Tyr His Ala Asn Asn Ser Thr Asp Thr Val
1               5                   10                  15

Asp Thr Val Leu Glu Lys Asn Ile Thr Val Thr His Ser Val Asn Leu
            20                  25                  30

Leu Glu Asn Arg His Asn Gly Lys Leu Cys Lys Leu Gly Gly Ile Ala
        35                  40                  45

-continued

```
Pro Leu His Leu Gly Lys Cys Asn Ile Ala Gly Trp Leu Gly Asn
    50                  55                  60
Pro Glu Cys Glu Leu Leu Phe Thr Val Ser Ser Trp Ser Tyr Ile Val
65                      70                  75                  80
Glu Thr Ser Asn Ser Asp Asn Gly Thr Cys Tyr Pro Gly Asp Phe Ile
                    85                  90                  95
Asn Tyr Glu Glu Leu Arg Glu Gln Leu Ser Ser Val Ser Ser Phe Glu
                100                 105                 110
Lys Phe Glu Ile Phe Pro Lys Thr Ser Ser Trp Pro Asn His Glu Thr
            115                 120                 125
Asn Arg Gly Val Thr Ala Ala Cys Pro Tyr Ala Gly Ala Asn Ser Phe
        130                 135                 140
Tyr Arg Asn Leu Ile Trp Leu Val Lys Gly Ser Ser Tyr Pro Lys
145                 150                 155                 160
Leu Ser Lys Ser Tyr Val Asn Asn Lys Gly Lys Glu Val Leu Val Leu
                165                 170                 175
Trp Gly Ile His His Pro Pro Thr Ser Thr Asp Gln Gln Ser Leu Tyr
                180                 185                 190
Gln Asn Ala Asp Ala Tyr Val Phe Val Gly Ser Ser Lys Tyr Asn Arg
            195                 200                 205
Lys Phe Lys Pro Glu Ile Ala Ala Arg Pro Lys Val Arg Gly Gln Ala
        210                 215                 220
Gly Arg Met Asn Tyr Tyr Trp Thr Leu Ile Glu Pro Gly Asp Thr Ile
225                 230                 235                 240
Thr Phe Glu Ala Thr Gly Asn Leu Val Val Pro Arg Tyr Ala Phe Ala
                245                 250                 255
Met Asn Arg Gly Ser Gly Ser Gly Ile Ile Ser Asp Ala Pro Val
                260                 265                 270
His Asp Cys Asn Thr Lys Cys Gln Thr Pro Lys Gly Ala Ile Asn Thr
            275                 280                 285
Ser Leu Pro Phe Gln Asn Ile His Pro Val Thr Ile Gly Glu Cys Pro
        290                 295                 300
Lys Tyr Val Lys Ser Thr Lys Leu Arg Met Ala Thr Gly Leu Arg Asn
305                 310                 315                 320
Ile Pro Ser Ile Gln Ser Arg Gly Leu Phe Gly Ala Ile Ala Gly Phe
                325                 330                 335
Ile Glu Gly Gly Trp Thr Gly Met Ile Asp Gly Trp Tyr Gly Tyr His
                340                 345                 350
His Gln Asn Gly Gln Gly Ser Gly Tyr Ala Ala Asp Gln Lys Ser Thr
            355                 360                 365
Gln Asn Ala Ile Asp Gly Ile Thr Asn Lys Val Asn Ser Ile Ile Glu
        370                 375                 380
Lys Met Asn Met Gln Phe Thr Ala Val Gly Lys Glu Phe Asn Asn Leu
385                 390                 395                 400
Glu Lys Arg Ile Glu Asn Leu Asn Lys Lys Val Asp Asp Gly Phe Leu
                405                 410                 415
Asp Val Trp Thr Tyr Asn Ala Glu Leu Leu Val Leu Leu Glu Asn Glu
            420                 425                 430
Arg Thr Leu Asp Phe His Asp Ser Asn Val Lys Asn Leu Tyr Glu Lys
        435                 440                 445
Val Arg Ser Gln Leu Arg Asn Asn Ala Lys Glu Ile Gly Asn Gly Cys
450                 455                 460
```

Phe Glu Phe Tyr His Lys Cys Asp Asp Thr Cys Met Glu Ser
465                 470                 475

<210> SEQ ID NO 15
<211> LENGTH: 478
<212> TYPE: PRT
<213> ORGANISM: Influenza A virus
<220> FEATURE:
<223> OTHER INFORMATION: Influenza A/Hong Kong/117/77{H1N1}
      hemagglutinin HA1-480 domain

<400> SEQUENCE: 15

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Ser His Asn Gly Lys Leu Cys Arg Leu Lys Gly Ile Ala
            35                  40                  45

Pro Leu Gln Leu Gly Lys Cys Ser Ile Ala Gly Trp Ile Leu Gly Asn
50                  55                  60

Pro Glu Cys Glu Ser Leu Phe Ser Lys Lys Ser Trp Ser Tyr Ile Ala
65                  70                  75                  80

Glu Thr Pro Asn Ser Glu Asn Gly Thr Cys Tyr Pro Gly Tyr Phe Ala
                85                  90                  95

Asp Tyr Glu Glu Leu Arg Glu Gln Leu Ser Ser Val Ser Ser Phe Glu
            100                 105                 110

Arg Phe Glu Ile Phe Pro Lys Glu Arg Ser Trp Pro Lys His Asn Val
            115                 120                 125

Thr Arg Gly Val Thr Ala Ser Cys Ser His Lys Gly Lys Ser Ser Phe
130                 135                 140

Tyr Arg Asn Leu Leu Trp Leu Thr Glu Lys Asn Gly Ser Tyr Pro Asn
145                 150                 155                 160

Leu Ser Lys Ser Tyr Val Asn Asn Lys Glu Lys Glu Val Leu Val Leu
                165                 170                 175

Trp Gly Val His His Pro Ser Asn Ile Glu Asp Gln Lys Thr Ile Tyr
            180                 185                 190

Arg Lys Glu Asn Ala Tyr Val Ser Val Val Ser Ser Asn Tyr Asn Arg
            195                 200                 205

Arg Phe Thr Pro Glu Ile Ala Glu Arg Pro Lys Val Arg Gly Gln Ala
210                 215                 220

Gly Arg Ile Asn Tyr Tyr Trp Thr Leu Leu Glu Pro Gly Asp Thr Ile
225                 230                 235                 240

Ile Phe Glu Ala Asn Gly Asn Leu Ile Ala Pro Trp Tyr Ala Phe Ala
                245                 250                 255

Leu Ser Arg Gly Phe Gly Ser Gly Ile Ile Thr Ser Asn Ala Ser Met
            260                 265                 270

Asp Glu Cys Asp Thr Lys Cys Gln Thr Pro Gln Gly Ala Ile Asn Ser
            275                 280                 285

Ser Leu Pro Phe Gln Asn Val His Pro Val Thr Ile Gly Glu Cys Pro
290                 295                 300

Lys Tyr Val Arg Ser Thr Lys Leu Arg Met Val Thr Gly Leu Arg Asn
305                 310                 315                 320

Ile Pro Ser Ile Gln Ser Arg Gly Leu Phe Gly Ala Ile Ala Gly Phe
                325                 330                 335

Ile Glu Gly Gly Trp Thr Gly Met Ile Asp Gly Trp Tyr Gly Tyr His
            340                 345                 350

-continued

His Gln Asn Glu Gln Gly Ser Gly Tyr Ala Ala Asp Gln Lys Ser Thr
            355                 360                 365

Gln Asn Ala Ile Asn Gly Ile Thr Asn Lys Val Asn Ser Val Ile Glu
370                 375                 380

Lys Met Asn Thr Gln Phe Thr Ala Val Gly Lys Glu Phe Asn Lys Leu
385                 390                 395                 400

Glu Lys Arg Met Glu Asn Leu Asn Lys Lys Val Asp Asp Gly Phe Leu
            405                 410                 415

Asp Ile Trp Thr Tyr Asn Ala Glu Leu Leu Val Leu Leu Glu Asn Glu
            420                 425                 430

Arg Thr Leu Asp Phe His Asp Ser Asn Val Lys Asn Leu Tyr Glu Lys
            435                 440                 445

Val Lys Ser Gln Leu Lys Asn Asn Ala Lys Glu Ile Gly Asn Gly Cys
        450                 455                 460

Phe Glu Phe Tyr His Lys Cys Asn Asn Glu Cys Met Glu Ser
465                 470                 475

<210> SEQ ID NO 16
<211> LENGTH: 476
<212> TYPE: PRT
<213> ORGANISM: Influenza A virus
<220> FEATURE:
<223> OTHER INFORMATION: Influenza A/Berkeley/1/68{H2N2} hemagglutinin
      HA1-480 domain

<400> SEQUENCE: 16

Asp Gln Ile Cys Ile Gly Tyr His Ala Asn Asn Ser Thr Glu Lys Val
1               5                   10                  15

Asp Thr Ile Leu Glu Arg Asn Val Thr Val Thr His Ala Lys Asp Ile
            20                  25                  30

Leu Glu Lys Thr His Asn Gly Lys Leu Cys Lys Leu Asn Gly Ile Pro
        35                  40                  45

Pro Leu Glu Leu Gly Asp Cys Ser Ile Ala Gly Trp Leu Leu Gly Asn
    50                  55                  60

Pro Glu Cys Asp Arg Leu Leu Ser Val Pro Glu Trp Ser Tyr Ile Met
65                  70                  75                  80

Glu Lys Glu Asn Pro Arg Tyr Ser Leu Cys Tyr Pro Gly Ser Phe Asn
                85                  90                  95

Asp Tyr Glu Glu Leu Lys His Leu Leu Ser Ser Val Lys His Phe Glu
            100                 105                 110

Lys Val Lys Ile Leu Pro Lys Asp Gly Trp Thr Gln His Glu Thr Thr
        115                 120                 125

Gly Gly Ser Lys Ala Cys Ala Val Ser Gly Lys Pro Ser Phe Phe Arg
    130                 135                 140

Asn Met Val Trp Leu Thr Lys Lys Gly Pro Asn Tyr Pro Val Ala Lys
145                 150                 155                 160

Gly Ser Tyr Asn Asn Thr Ser Gly Glu Gln Met Leu Ile Ile Trp Gly
                165                 170                 175

Val His His Pro Asn Asp Glu Ala Glu Gln Arg Ala Leu Tyr Gln Glu
            180                 185                 190

Val Gly Thr Tyr Val Ser Glu Ala Thr Ser Thr Leu Asn Lys Arg Ser
        195                 200                 205

Thr Pro Glu Ile Ala Ala Arg Pro Lys Val Ser Gly Leu Gly Ser Arg
    210                 215                 220

Met Glu Phe Ser Trp Thr Leu Leu Asp Met Trp Asp Thr Ile Ser Phe

```
            225                 230                 235                 240
        Glu Ser Thr Gly Asn Leu Val Ala Pro Glu Tyr Gly Phe Lys Ile Ser
                    245                 250                 255

Lys Arg Gly Ser Ser Gly Ile Met Lys Thr Glu Gly Thr Leu Glu Asn
                    260                 265                 270

Cys Glu Thr Lys Cys Gln Thr Pro Leu Gly Ala Ile Asn Thr Thr Leu
                    275                 280                 285

Pro Phe His Asn Val His Pro Leu Thr Ile Gly Glu Cys Pro Lys Tyr
                    290                 295                 300

Val Lys Ser Glu Lys Leu Val Leu Ala Thr Gly Leu Arg Asn Val Pro
        305                 310                 315                 320

Gln Ile Glu Ser Arg Gly Leu Phe Gly Ala Ile Ala Gly Phe Ile Glu
                    325                 330                 335

Gly Gly Trp Gln Gly Met Val Asp Gly Trp Tyr Gly Tyr His His Ser
                    340                 345                 350

Asn Asp Gln Gly Ser Gly Tyr Ala Ala Asp Lys Glu Ser Thr Gln Lys
                    355                 360                 365

Ala Phe Asp Gly Ile Thr Asn Lys Val Asn Ser Val Ile Glu Lys Met
                    370                 375                 380

Asn Thr Gln Phe Glu Ala Val Gly Lys Glu Phe Ser Asn Leu Glu Lys
        385                 390                 395                 400

Arg Leu Glu Asn Leu Asn Lys Lys Met Glu Asp Gly Phe Leu Asp Val
                    405                 410                 415

Trp Thr Tyr Asn Ala Glu Leu Leu Val Leu Met Glu Asn Glu Arg Thr
                    420                 425                 430

Leu Asp Phe His Asp Ser Asn Val Lys Asn Leu Tyr Asp Lys Val Arg
                    435                 440                 445

Met Gln Leu Arg Asp Asn Val Lys Glu Leu Gly Asn Gly Cys Phe Glu
                    450                 455                 460

Phe Tyr His Lys Cys Asp Asp Glu Cys Met Asn Ser
        465                 470                 475

<210> SEQ ID NO 17
        <211> LENGTH: 470
        <212> TYPE: PRT
        <213> ORGANISM: Influenza A virus
        <220> FEATURE:
        <223> OTHER INFORMATION: Influenza A/Victoria/210/2009{H3N2}
              hemagglutinin HA1-480 domain

<400> SEQUENCE: 17

Ala Thr Leu Cys Leu Gly His His Ala Val Pro Asn Gly Thr Ile Val
        1               5                   10                  15

Lys Thr Ile Thr Asn Asp Gln Ile Glu Val Thr Asn Ala Thr Glu Leu
                    20                  25                  30

Val Gln Asn Ser Ser Thr Gly Glu Ile Cys Asp Ser Pro His Gln Ile
                    35                  40                  45

Leu Asp Gly Lys Asn Cys Thr Leu Ile Asp Ala Leu Leu Gly Asp Pro
                    50                  55                  60

Gln Cys Asp Gly Phe Gln Asn Lys Lys Trp Asp Leu Phe Val Glu Arg
        65                  70                  75                  80

Ser Lys Ala Tyr Ser Asn Cys Tyr Pro Tyr Asp Val Pro Asp Tyr Ala
                    85                  90                  95

Ser Leu Arg Ser Leu Val Ala Ser Ser Gly Thr Leu Glu Phe Asn Asn
                    100                 105                 110
```

Glu Ser Phe Asn Trp Thr Gly Val Thr Gln Asn Gly Thr Ser Ser Ala
            115                 120                 125

Cys Ile Arg Arg Ser Lys Asn Ser Phe Phe Ser Arg Leu Asn Trp Leu
130                 135                 140

Thr His Leu Asn Phe Lys Tyr Pro Ala Leu Asn Val Thr Met Pro Asn
145                 150                 155                 160

Asn Glu Gln Phe Asp Lys Leu Tyr Ile Trp Gly Val His His Pro Val
                165                 170                 175

Thr Asp Lys Asp Gln Ile Phe Leu Tyr Ala Gln Ala Ser Gly Arg Ile
            180                 185                 190

Thr Val Ser Thr Lys Arg Ser Gln Gln Thr Val Ile Pro Asn Ile Gly
            195                 200                 205

Ser Arg Pro Arg Val Arg Asn Ile Pro Thr Arg Ile Ser Ile Tyr Trp
            210                 215                 220

Thr Ile Val Lys Pro Gly Asp Ile Leu Leu Ile Asn Ser Thr Gly Asn
225                 230                 235                 240

Leu Ile Ala Pro Arg Gly Tyr Phe Lys Met Gln Ser Gly Lys Ser Ser
                245                 250                 255

Ile Met Arg Ser Asp Ala Pro Ile Gly Lys Cys Asn Ser Glu Cys Ile
            260                 265                 270

Thr Pro Asn Gly Ser Ile Pro Asn Asp Lys Pro Phe Gln Asn Val Asn
            275                 280                 285

Arg Ile Thr Tyr Gly Ala Cys Pro Arg Tyr Val Lys Gln Asn Thr Leu
            290                 295                 300

Lys Leu Ala Thr Gly Met Arg Asn Val Pro Glu Lys Gln Thr Arg Gly
305                 310                 315                 320

Ile Phe Gly Ala Ile Ala Gly Phe Ile Glu Asn Gly Trp Glu Gly Met
                325                 330                 335

Val Asp Gly Trp Tyr Gly Phe Arg His Gln Asn Ser Glu Gly Arg Gly
            340                 345                 350

Gln Ala Ala Asp Leu Lys Ser Thr Gln Ala Ala Ile Asp Gln Ile Asn
            355                 360                 365

Gly Lys Leu Asn Arg Leu Ile Gly Lys Thr Asn Glu Lys Phe His Gln
370                 375                 380

Ile Glu Lys Glu Phe Ser Glu Val Glu Gly Arg Ile Gln Asp Leu Glu
385                 390                 395                 400

Lys Tyr Val Glu Asp Thr Lys Ile Asp Leu Trp Ser Tyr Asn Ala Glu
                405                 410                 415

Leu Leu Val Ala Leu Glu Asn Gln His Thr Ile Asp Leu Thr Asp Ser
            420                 425                 430

Glu Met Asn Lys Leu Phe Glu Lys Thr Lys Lys Gln Leu Arg Glu Asn
            435                 440                 445

Ala Glu Asp Met Gly Asn Gly Cys Phe Lys Ile Tyr His Lys Cys Asp
            450                 455                 460

Asn Ala Cys Ile Gly Ser
465                 470

<210> SEQ ID NO 18
<211> LENGTH: 470
<212> TYPE: PRT
<213> ORGANISM: Influenza A virus
<220> FEATURE:
<223> OTHER INFORMATION: Influenza A/Wisconsin/15/2009{H3N2}
      hemagglutinin HA1-480 domain

<400> SEQUENCE: 18

-continued

```
Ala Thr Leu Cys Leu Gly His His Ala Val Pro Asn Gly Thr Ile Val
 1               5                  10                 15

Lys Thr Ile Thr Asn Asp Gln Ile Glu Val Thr Asn Ala Thr Glu Leu
                20                  25                 30

Val Gln Ser Ser Ser Thr Gly Glu Ile Cys Asp Ser Pro His Gln Ile
            35                  40                  45

Leu Asp Gly Lys Asn Cys Thr Leu Ile Asp Ala Leu Leu Gly Asp Pro
 50                  55                  60

Gln Cys Asp Asp Phe Gln Asn Lys Lys Trp Asp Leu Phe Val Glu Arg
 65                  70                  75                  80

Ser Lys Ala Tyr Ser Asn Cys Tyr Pro Tyr Asp Val Pro Asp Tyr Ala
                85                  90                  95

Ser Leu Arg Ser Leu Val Ala Ser Ser Gly Thr Leu Glu Phe Asn Asn
            100                 105                 110

Glu Ser Phe Asn Trp Thr Gly Val Thr Gln Asn Gly Thr Ser Ser Ala
            115                 120                 125

Cys Ile Arg Arg Ser Lys Asn Ser Phe Phe Ser Arg Leu Asn Trp Leu
130                 135                 140

Thr His Leu Asn Phe Lys Tyr Pro Ala Leu Asn Val Thr Met Pro Asn
145                 150                 155                 160

Asn Glu Gln Phe Asp Lys Leu Tyr Ile Trp Gly Val His His Pro Gly
                165                 170                 175

Thr Asp Lys Asp Gln Ile Phe Pro Tyr Ala Gln Ala Ser Gly Arg Ile
            180                 185                 190

Thr Val Ser Thr Lys Arg Ser Gln Gln Thr Ala Ile Pro Asn Ile Gly
            195                 200                 205

Ser Arg Pro Arg Val Arg Asn Ile Pro Ser Arg Ile Ser Ile Tyr Trp
210                 215                 220

Thr Ile Val Lys Pro Gly Asp Ile Leu Leu Ile Asn Ser Thr Gly Asn
225                 230                 235                 240

Leu Ile Ala Pro Arg Gly Tyr Phe Lys Ile Arg Ser Gly Lys Ser Ser
                245                 250                 255

Ile Met Arg Ser Asp Ala Pro Ile Gly Lys Cys Asn Ser Glu Cys Ile
            260                 265                 270

Thr Pro Asn Gly Ser Ile Pro Asn Asp Lys Pro Phe Gln Asn Val Asn
            275                 280                 285

Arg Ile Thr Tyr Gly Ala Cys Pro Arg Tyr Val Lys Gln Asn Thr Leu
290                 295                 300

Lys Leu Ala Thr Gly Met Arg Asn Val Pro Glu Lys Gln Thr Arg Gly
305                 310                 315                 320

Ile Phe Gly Ala Ile Ala Gly Phe Ile Glu Asn Gly Trp Glu Gly Met
                325                 330                 335

Val Asp Gly Trp Tyr Gly Phe Arg His Gln Asn Ser Glu Gly Arg Gly
            340                 345                 350

Gln Ala Ala Asp Leu Lys Ser Thr Gln Ala Ala Ile Asp Gln Ile Asn
            355                 360                 365

Gly Lys Leu Asn Arg Leu Ile Gly Lys Thr Asn Glu Lys Phe His Gln
370                 375                 380

Ile Glu Lys Glu Phe Ser Glu Val Glu Gly Arg Ile Gln Asp Leu Glu
385                 390                 395                 400

Lys Tyr Val Glu Asp Thr Lys Ile Asp Leu Trp Ser Tyr Asn Ala Glu
                405                 410                 415
```

```
Leu Leu Val Ala Leu Glu Asn Gln His Thr Ile Asp Leu Thr Asp Ser
                420                 425                 430

Glu Met Asn Lys Leu Phe Glu Lys Thr Lys Lys Gln Leu Arg Glu Asn
            435                 440                 445

Ala Glu Asp Met Gly Asn Gly Cys Phe Lys Ile Tyr His Lys Cys Asp
    450                 455                 460

Asn Ala Cys Ile Gly Ser
465             470

<210> SEQ ID NO 19
<211> LENGTH: 472
<212> TYPE: PRT
<213> ORGANISM: Influenza A virus
<220> FEATURE:
<223> OTHER INFORMATION: Influenza A/chicken/Alabama/1/1975{H4N8}
      hemagglutinin HA1-480 domain

<400> SEQUENCE: 19

Pro Val Ile Cys Leu Gly His His Ala Val Ser Asn Gly Thr Met Val
 1               5                  10                  15

Lys Thr Leu Thr Asp Asp Gln Val Glu Val Val Thr Ala Gln Glu Leu
             20                  25                  30

Val Glu Ser Gln His Leu Pro Glu Leu Cys Pro Ser Pro Leu Arg Leu
         35                  40                  45

Val Asp Gly Gln Thr Cys Asp Ile Val Asn Gly Ala Leu Gly Ser Pro
     50                  55                  60

Gly Cys Asn His Leu Asn Gly Ala Glu Trp Asp Val Phe Ile Glu Arg
 65                  70                  75                  80

Pro Thr Ala Val Asp Thr Cys Tyr Pro Phe Asp Val Pro Asp Tyr Gln
                 85                  90                  95

Ser Leu Arg Ser Ile Leu Ala Asn Asn Gly Lys Phe Glu Phe Ile Val
            100                 105                 110

Glu Lys Phe Gln Trp Asn Thr Val Lys Gln Asn Gly Lys Ser Gly Ala
        115                 120                 125

Cys Lys Arg Ala Asn Glu Asn Asp Phe Phe Thr Asn Leu Asn Trp Leu
    130                 135                 140

Thr Lys Ser Asp Gly Asn Ala Tyr Pro Leu Gln Asn Leu Thr Lys Val
145                 150                 155                 160

Asn Asn Gly Asp Tyr Ala Arg Leu Tyr Ile Trp Gly Val His His Pro
                165                 170                 175

Ser Thr Asp Thr Glu Gln Thr Asn Leu Tyr Glu Asn Asn Pro Gly Arg
            180                 185                 190

Val Thr Val Ser Thr Lys Thr Ser Gln Thr Ser Val Val Pro Asn Ile
        195                 200                 205

Gly Ser Arg Pro Trp Val Arg Gly Gln Ser Gly Arg Ile Ser Phe Tyr
    210                 215                 220

Trp Thr Ile Val Glu Pro Gly Asp Ile Ile Val Phe Asn Thr Ile Gly
225                 230                 235                 240

Asn Leu Ile Ala Pro Arg Gly His Tyr Lys Leu Asn Ser Gln Lys Lys
                245                 250                 255

Ser Thr Ile Leu Asn Thr Ala Val Pro Ile Gly Ser Cys Val Ser Lys
            260                 265                 270

Cys His Thr Asp Arg Gly Ser Ile Thr Thr Thr Lys Pro Phe Gln Asn
        275                 280                 285

Ile Ser Arg Ile Ser Ile Gly Asp Cys Pro Lys Tyr Val Lys Gln Gly
    290                 295                 300
```

```
Ser Leu Lys Leu Ala Thr Gly Met Arg Asn Ile Pro Glu Lys Ala Thr
305                 310                 315                 320

Arg Gly Leu Phe Gly Ala Ile Ala Gly Phe Ile Glu Asn Gly Trp Gln
            325                 330                 335

Gly Leu Ile Asp Gly Trp Tyr Gly Phe Arg His Gln Asn Ala Glu Gly
            340                 345                 350

Thr Gly Thr Ala Ala Asp Leu Lys Ser Thr Gln Ala Ala Ile Asp Gln
        355                 360                 365

Ile Asn Gly Lys Leu Asn Arg Leu Ile Glu Lys Thr Asn Glu Lys Tyr
        370                 375                 380

His Gln Ile Glu Lys Glu Phe Glu Gln Val Glu Gly Arg Ile Gln Asp
385                 390                 395                 400

Leu Glu Lys Tyr Val Glu Asp Thr Lys Ile Asp Leu Trp Ser Tyr Asn
                405                 410                 415

Ala Glu Leu Leu Val Ala Leu Glu Asn Gln His Thr Ile Asp Val Thr
            420                 425                 430

Asp Ser Glu Met Asp Lys Leu Phe Glu Arg Val Arg Arg Gln Leu Arg
        435                 440                 445

Glu Asn Ala Glu Asp Lys Gly Asn Gly Cys Phe Glu Ile Phe His Gln
    450                 455                 460

Cys Asp Asn Asn Cys Ile Glu Ser
465                 470

<210> SEQ ID NO 20
<211> LENGTH: 479
<212> TYPE: PRT
<213> ORGANISM: Influenza A virus
<220> FEATURE:
<223> OTHER INFORMATION: Influenza A/mallard/Ohio/170/1999{H6N5}
      hemagglutinin HA1-480 domain

<400> SEQUENCE: 20

Asp Arg Ile Cys Ile Gly Tyr His Ala Asn Asn Ser Thr Thr Gln Val
1               5                   10                  15

Asp Thr Ile Leu Glu Lys Asn Val Thr Val Thr His Ser Val Glu Leu
            20                  25                  30

Leu Glu Ser Lys Lys Glu Ser Ile Phe Cys Arg Val Leu Asn Lys Ala
        35                  40                  45

Pro Leu Asp Leu Met Asp Cys Thr Thr Glu Gly Trp Ile Leu Gly Asn
    50                  55                  60

Pro Arg Cys Asp Asn Leu Leu Gly Asp Gln Ser Trp Ser Tyr Ile Val
65                  70                  75                  80

Glu Arg Pro Asp Ala Lys Asn Gly Ile Cys Tyr Pro Gly Val Leu Lys
                85                  90                  95

Glu Thr Glu Glu Leu Lys Ala Leu Ile Gly Ser Ile Asp Ser Ile Gln
            100                 105                 110

Arg Phe Glu Met Phe Pro Lys Asn Thr Trp Thr Gly Val Asp Thr Ser
        115                 120                 125

Ser Gly Val Ser Ser Ala Cys Pro Tyr Asn Gly Gly Ser Ser Phe Tyr
    130                 135                 140

Arg Asn Leu Leu Trp Ile Ile Lys Thr Arg Ser Asp Pro Tyr Ser Leu
145                 150                 155                 160

Val Lys Gly Thr Tyr Thr Asn Thr Gly Ser Gln Pro Ile Leu Tyr Phe
                165                 170                 175

Trp Gly Val His His Pro Pro Asp Asp Val Glu Gln Ala Asn Leu Tyr
```

```
                180             185             190
Gly Leu Gly Thr Arg Tyr Val Arg Met Gly Thr Glu Ser Met Asn Phe
            195                 200                 205

Ala Lys Gly Pro Glu Ile Ala Asp Arg Pro Ala Asn Gly Gln Arg
    210                 215                 220

Gly Arg Ile Asp Tyr Tyr Trp Ser Val Leu Lys Pro Gly Glu Thr Leu
225                 230                 235                 240

Asn Val Glu Ser Asn Gly Asn Leu Ile Ala Pro Trp Tyr Ala Tyr Lys
                245                 250                 255

Phe Thr Asn Ser Arg Asn Lys Gly Ala Ile Phe Lys Ser Asp Leu Pro
            260                 265                 270

Ile Glu Asn Cys Asp Ala Val Cys Gln Thr Ile Ala Gly Ala Ile Asn
        275                 280                 285

Thr Asn Lys Thr Phe Gln Asn Val Ser Pro Ile Trp Ile Gly Glu Cys
    290                 295                 300

Pro Lys Tyr Val Lys Ser Lys Ser Leu Lys Leu Ala Thr Gly Leu Arg
305                 310                 315                 320

Asn Val Pro Gln Val Lys Thr Arg Gly Leu Phe Gly Ala Ile Ala Gly
                325                 330                 335

Phe Ile Glu Gly Gly Trp Thr Gly Met Val Asp Gly Trp Tyr Gly Tyr
            340                 345                 350

His His Glu Asn Ser Gln Gly Ser Gly Tyr Ala Ala Asp Lys Glu Ser
        355                 360                 365

Thr Gln Lys Ala Ile Asp Gly Ile Thr Asn Lys Val Asn Ser Ile Ile
    370                 375                 380

Asp Lys Met Asn Thr Gln Phe Glu Ala Val Glu His Glu Phe Ser Asn
385                 390                 395                 400

Leu Glu Arg Arg Ile Gly Asn Leu Asn Lys Arg Met Glu Asp Gly Phe
                405                 410                 415

Leu Asp Val Trp Thr Tyr Asn Ala Glu Leu Leu Val Leu Leu Glu Asn
            420                 425                 430

Glu Arg Thr Leu Asp Met His Asp Ala Asn Val Lys Asn Leu His Glu
        435                 440                 445

Lys Val Lys Ser Gln Leu Lys Asp Asn Ala Lys Asp Leu Gly Asn Gly
    450                 455                 460

Cys Phe Glu Phe Trp His Lys Cys Asp Asn Glu Cys Ile Lys Ser
465                 470                 475

<210> SEQ ID NO 21
<211> LENGTH: 474
<212> TYPE: PRT
<213> ORGANISM: Influenza A virus
<220> FEATURE:
<223> OTHER INFORMATION: Influenza A/Netherlands/219/03{H7N7}
      hemagglutinin HA1-480 domain

<400> SEQUENCE: 21

Asp Lys Ile Cys Leu Gly His His Ala Val Ser Asn Gly Thr Lys Val
  1               5                   10                  15

Asn Thr Leu Thr Glu Arg Gly Val Glu Val Val Asn Ala Thr Glu Thr
            20                  25                  30

Val Glu Arg Thr Asn Val Pro Arg Ile Cys Ser Lys Gly Lys Arg Thr
        35                  40                  45

Val Asp Leu Gly Gln Cys Gly Leu Leu Gly Thr Ile Thr Gly Pro Pro
    50                  55                  60
```

Gln Cys Asp Gln Phe Leu Glu Phe Ser Ala Asp Leu Ile Ile Glu Arg
65                  70                  75                  80

Arg Glu Gly Ser Asp Val Cys Tyr Pro Gly Lys Phe Val Asn Glu Glu
            85                  90                  95

Ala Leu Arg Gln Ile Leu Arg Glu Ser Gly Ile Asp Lys Glu Thr
                100                 105                 110

Met Gly Phe Thr Tyr Ser Gly Ile Arg Thr Asn Gly Thr Thr Ser Ala
        115                 120                 125

Cys Arg Arg Ser Gly Ser Ser Phe Tyr Ala Glu Met Lys Trp Leu Leu
        130                 135                 140

Ser Asn Thr Asp Asn Ala Ala Phe Pro Gln Met Thr Lys Ser Tyr Lys
145                 150                 155                 160

Asn Thr Arg Lys Asp Pro Ala Leu Ile Ile Trp Gly Ile His His Ser
                165                 170                 175

Gly Ser Thr Thr Glu Gln Thr Lys Leu Tyr Gly Ser Gly Asn Lys Leu
        180                 185                 190

Ile Thr Val Gly Ser Ser Asn Tyr Gln Gln Ser Phe Val Pro Ser Pro
        195                 200                 205

Gly Ala Arg Pro Gln Val Asn Gly Gln Ser Gly Arg Ile Asp Phe His
210                 215                 220

Trp Leu Ile Leu Asn Pro Asn Asp Thr Val Thr Phe Ser Phe Asn Gly
225                 230                 235                 240

Ala Phe Ile Ala Pro Asp Arg Ala Ser Phe Leu Arg Gly Lys Ser Met
                245                 250                 255

Gly Ile Gln Ser Glu Val Gln Val Asp Ala Asn Cys Glu Gly Asp Cys
        260                 265                 270

Tyr His Ser Gly Gly Thr Ile Ile Ser Asn Leu Pro Phe Gln Asn Ile
        275                 280                 285

Asn Ser Arg Ala Val Gly Lys Cys Pro Arg Tyr Val Lys Gln Glu Ser
290                 295                 300

Leu Leu Leu Ala Thr Gly Met Lys Asn Val Pro Glu Ile Pro Lys Arg
305                 310                 315                 320

Arg Arg Arg Gly Leu Phe Gly Ala Ile Ala Gly Phe Ile Glu Asn Gly
                325                 330                 335

Trp Glu Gly Leu Ile Asp Gly Trp Tyr Gly Phe Arg His Gln Asn Ala
        340                 345                 350

Gln Gly Glu Gly Thr Ala Ala Asp Tyr Lys Ser Thr Gln Ser Ala Ile
        355                 360                 365

Asp Gln Ile Thr Gly Lys Leu Asn Arg Leu Ile Glu Lys Thr Asn Gln
370                 375                 380

Gln Phe Glu Leu Ile Asp Asn Glu Phe Thr Glu Val Glu Arg Gln Ile
385                 390                 395                 400

Gly Asn Val Ile Asn Trp Thr Arg Asp Ser Met Thr Glu Val Trp Ser
                405                 410                 415

Tyr Asn Ala Glu Leu Leu Val Ala Met Glu Asn Gln His Thr Ile Asp
        420                 425                 430

Leu Ala Asp Ser Glu Met Asn Lys Leu Tyr Glu Arg Val Lys Arg Gln
        435                 440                 445

Leu Arg Glu Asn Ala Glu Glu Asp Gly Thr Gly Cys Phe Glu Ile Phe
450                 455                 460

His Lys Cys Asp Asp Asp Cys Met Ala Ser
465                 470

```
<210> SEQ ID NO 22
<211> LENGTH: 478
<212> TYPE: PRT
<213> ORGANISM: Influenza A virus
<220> FEATURE:
<223> OTHER INFORMATION: Influenza A/duck/Alaska/702/1991{H8N2}
      hemagglutinin HA1-480 domain

<400> SEQUENCE: 22
```

Asp Arg Ile Cys Ile Gly Tyr Gln Ser Asn Asn Ser Thr Asp Thr Val
 1               5                  10                  15

Asn Thr Leu Ile Glu Gln Asn Val Pro Val Thr Gln Thr Met Glu Leu
            20                  25                  30

Val Glu Thr Glu Lys His Ser Ala Tyr Cys Asn Thr Asp Leu Gly Ala
        35                  40                  45

Pro Leu Glu Leu Arg Asp Cys Lys Ile Glu Ala Val Ile Tyr Gly Asn
    50                  55                  60

Pro Lys Cys Asp Ile His Leu Lys Asp Gln Gly Trp Ser Tyr Ile Val
65                  70                  75                  80

Glu Arg Pro Ser Ala Pro Glu Gly Met Cys Tyr Pro Gly Ser Val Glu
                85                  90                  95

Asn Leu Glu Glu Leu Arg Phe Val Phe Ser Asn Ala Ala Ser Tyr Lys
            100                 105                 110

Arg Ile Arg Leu Phe Asp Tyr Ser Arg Trp Asn Val Thr Ser Ser Gly
        115                 120                 125

Thr Ser Lys Ala Cys Asn Ala Ser Thr Gly Gly Gln Ser Phe Tyr Arg
130                 135                 140

Ser Ile Asn Trp Leu Thr Lys Lys Lys Pro Asp Thr Tyr Asp Phe Asn
145                 150                 155                 160

Glu Gly Ser Tyr Val Asn Asn Glu Asp Gly Asp Ile Ile Phe Leu Trp
                165                 170                 175

Gly Ile His His Pro Pro Asp Thr Lys Glu Gln Thr Thr Leu Tyr Lys
            180                 185                 190

Asn Ala Asn Thr Leu Ser Ser Val Thr Thr Asn Thr Ile Asn Arg Ser
        195                 200                 205

Phe Gln Pro Asn Ile Gly Pro Arg Pro Leu Val Arg Gly Gln Gln Gly
    210                 215                 220

Arg Met Asp Tyr Tyr Trp Gly Ile Leu Lys Arg Gly Glu Thr Leu Lys
225                 230                 235                 240

Ile Arg Thr Asn Gly Asn Leu Ile Ala Pro Glu Phe Gly Tyr Leu Leu
                245                 250                 255

Lys Gly Glu Ser His Gly Arg Ile Ile Gln Asn Glu Asp Ile Pro Ile
            260                 265                 270

Gly Asn Cys Lys Thr Lys Cys Gln Thr Tyr Ala Gly Ala Ile Asn Ser
        275                 280                 285

Ser Lys Pro Phe Gln Asn Ala Ser Arg His Tyr Met Gly Glu Cys Pro
    290                 295                 300

Lys Tyr Val Lys Lys Ala Ser Leu Arg Leu Ala Val Gly Leu Arg Asn
305                 310                 315                 320

Thr Pro Ser Val Glu Pro Lys Gly Leu Phe Gly Ala Ile Ala Gly Phe
                325                 330                 335

Ile Glu Gly Gly Trp Ser Gly Met Ile Asp Gly Trp Tyr Gly Phe His
            340                 345                 350

His Ser Asn Ser Glu Gly Thr Gly Met Ala Ala Asp Gln Lys Ser Thr
        355                 360                 365

```
Gln Glu Ala Ile Asp Lys Ile Thr Asn Lys Ile Asn Asn Ile Val Asp
        370                 375                 380
Lys Met Asn Arg Glu Phe Glu Val Met Asn His Glu Phe Ser Glu Val
385                 390                 395                 400
Glu Lys Arg Ile Asn Met Ile Asn Asp Lys Ile Asp Asp Gln Ile Glu
                405                 410                 415
Asp Leu Trp Ala Tyr Asn Ala Glu Leu Leu Val Leu Leu Glu Asn Gln
                420                 425                 430
Lys Thr Leu Asp Glu His Asp Ser Asn Val Lys Asn Leu Phe Asp Glu
                435                 440                 445
Val Lys Arg Arg Leu Ser Ala Asn Ala Ile Asp Ala Gly Asn Gly Cys
450                 455                 460
Phe Asp Ile Leu His Lys Cys Asp Asn Glu Cys Met Glu Thr
465                 470                 475

<210> SEQ ID NO 23
<211> LENGTH: 471
<212> TYPE: PRT
<213> ORGANISM: Influenza A virus
<220> FEATURE:
<223> OTHER INFORMATION: Influenza A/Hong Kong/1073/99{H9N2}
      hemagglutinin HA1-480 domain

<400> SEQUENCE: 23

Asp Lys Ile Cys Ile Gly His Gln Ser Thr Asn Ser Thr Glu Thr Val
1               5                   10                  15
Asp Thr Leu Thr Glu Thr Asn Val Pro Val Thr His Ala Lys Glu Leu
            20                  25                  30
Leu His Thr Glu His Asn Gly Met Leu Cys Ala Thr Ser Leu Gly His
        35                  40                  45
Pro Leu Ile Leu Asp Thr Cys Thr Ile Glu Gly Leu Val Tyr Gly Asn
    50                  55                  60
Pro Ser Cys Asp Leu Leu Leu Gly Gly Arg Glu Trp Ser Tyr Ile Val
65                  70                  75                  80
Glu Arg Ser Ser Ala Val Asn Gly Thr Cys Tyr Pro Gly Asn Val Glu
                85                  90                  95
Asn Leu Glu Glu Leu Arg Thr Leu Phe Ser Ser Ala Ser Ser Tyr Gln
            100                 105                 110
Arg Ile Gln Ile Phe Pro Asp Thr Thr Trp Asn Val Thr Tyr Thr Gly
        115                 120                 125
Thr Ser Arg Ala Cys Ser Gly Ser Phe Tyr Arg Ser Met Arg Trp Leu
130                 135                 140
Thr Gln Lys Ser Gly Phe Tyr Pro Val Gln Asp Ala Gln Tyr Thr Asn
145                 150                 155                 160
Asn Arg Gly Lys Ser Ile Leu Phe Val Trp Gly Ile His His Pro Pro
                165                 170                 175
Thr Tyr Thr Glu Gln Thr Asn Leu Tyr Ile Arg Asn Asp Thr Thr Thr
            180                 185                 190
Ser Val Thr Thr Glu Asp Leu Asn Arg Thr Phe Lys Pro Val Ile Gly
        195                 200                 205
Pro Arg Pro Leu Val Asn Gly Leu Gln Gly Arg Ile Asp Tyr Tyr Trp
    210                 215                 220
Ser Val Leu Lys Pro Gly Gln Thr Leu Arg Val Arg Ser Asn Gly Asn
225                 230                 235                 240
Leu Ile Ala Pro Trp Tyr Gly His Val Leu Ser Gly Gly Ser His Gly
                245                 250                 255
```

```
Arg Ile Leu Lys Thr Asp Leu Lys Gly Gly Asn Cys Val Val Gln Cys
            260                 265                 270

Gln Thr Glu Lys Gly Gly Leu Asn Ser Thr Leu Pro Phe His Asn Ile
        275                 280                 285

Ser Lys Tyr Ala Phe Gly Thr Cys Pro Lys Tyr Val Arg Val Asn Ser
    290                 295                 300

Leu Lys Leu Ala Val Gly Leu Arg Asn Val Pro Ala Arg Ser Ser Arg
305                 310                 315                 320

Gly Leu Phe Gly Ala Ile Ala Gly Phe Ile Glu Gly Gly Trp Pro Gly
                325                 330                 335

Leu Val Ala Gly Trp Tyr Gly Phe Gln His Ser Asn Asp Gln Gly Val
            340                 345                 350

Gly Met Ala Ala Asp Arg Asp Ser Thr Gln Lys Ala Ile Asp Lys Ile
        355                 360                 365

Thr Ser Lys Val Asn Asn Ile Val Asp Lys Met Asn Lys Gln Tyr Glu
    370                 375                 380

Ile Ile Asp His Glu Phe Ser Glu Val Glu Thr Arg Leu Asn Met Ile
385                 390                 395                 400

Asn Asn Lys Ile Asp Asp Gln Ile Gln Asp Val Trp Ala Tyr Asn Ala
                405                 410                 415

Glu Leu Leu Val Leu Leu Glu Asn Gln Lys Thr Leu Asp Glu His Asp
            420                 425                 430

Ala Asn Val Asn Asn Leu Tyr Asn Lys Val Lys Arg Ala Leu Gly Ser
        435                 440                 445

Asn Ala Met Glu Asp Gly Lys Gly Cys Phe Glu Leu Tyr His Lys Cys
    450                 455                 460

Asp Asp Gln Cys Met Glu Thr
465                 470

<210> SEQ ID NO 24
<211> LENGTH: 474
<212> TYPE: PRT
<213> ORGANISM: Influenza A virus
<220> FEATURE:
<223> OTHER INFORMATION: Influenza A/chicken/Germany/N/1949{H10N7}
      hemagglutinin HA1-480 domain

<400> SEQUENCE: 24

Asp Arg Ile Cys Leu Gly His His Ala Val Ala Asn Gly Thr Ile Val
1               5                   10                  15

Lys Thr Leu Thr Asn Glu Gln Glu Glu Val Thr Asn Ala Thr Glu Thr
            20                  25                  30

Val Glu Ser Thr Asn Leu Asn Lys Leu Cys Met Lys Gly Arg Ser Tyr
        35                  40                  45

Lys Asp Leu Gly Asn Cys His Pro Val Gly Met Leu Ile Gly Thr Pro
    50                  55                  60

Val Cys Asp Pro His Leu Thr Gly Thr Trp Asp Thr Leu Ile Glu Arg
65                  70                  75                  80

Glu Asn Ala Ile Ala His Cys Tyr Pro Gly Ala Thr Ile Asn Glu Glu
                85                  90                  95

Ala Leu Arg Gln Lys Ile Met Glu Ser Gly Gly Ile Ser Lys Met Ser
            100                 105                 110

Thr Gly Phe Thr Tyr Gly Ser Ser Ile Thr Ser Ala Gly Thr Thr Lys
        115                 120                 125

Ala Cys Met Arg Asn Gly Gly Asp Ser Phe Tyr Ala Glu Leu Lys Trp
```

-continued

```
    130                 135                 140

Leu Val Ser Lys Thr Lys Gly Gln Asn Phe Pro Gln Thr Thr Asn Thr
145                 150                 155                 160

Tyr Arg Asn Thr Asp Thr Ala Glu His Leu Ile Ile Trp Gly Ile His
                165                 170                 175

His Pro Ser Ser Thr Gln Glu Lys Asn Asp Leu Tyr Gly Thr Gln Ser
            180                 185                 190

Leu Ser Ile Ser Val Glu Ser Ser Thr Tyr Gln Asn Asn Phe Val Pro
        195                 200                 205

Val Val Gly Ala Arg Pro Gln Val Asn Gly Gln Ser Gly Arg Ile Asp
    210                 215                 220

Phe His Trp Thr Leu Val Gln Pro Gly Asp Asn Ile Thr Phe Ser Asp
225                 230                 235                 240

Asn Gly Gly Leu Ile Ala Pro Ser Arg Val Ser Lys Leu Thr Gly Arg
                245                 250                 255

Asp Leu Gly Ile Gln Ser Glu Ala Leu Ile Asp Asn Ser Cys Glu Ser
            260                 265                 270

Lys Cys Phe Trp Arg Gly Gly Ser Ile Asn Thr Lys Leu Pro Phe Gln
        275                 280                 285

Asn Leu Ser Pro Arg Thr Val Gly Gln Cys Pro Lys Tyr Val Asn Gln
    290                 295                 300

Arg Ser Leu Leu Leu Ala Thr Gly Met Arg Asn Val Pro Glu Val Val
305                 310                 315                 320

Gln Gly Arg Gly Leu Phe Gly Ala Ile Ala Gly Phe Ile Glu Asn Gly
                325                 330                 335

Trp Glu Gly Met Val Asp Gly Trp Tyr Gly Phe Arg His Gln Asn Ala
            340                 345                 350

Gln Gly Thr Gly Gln Ala Ala Asp Tyr Lys Ser Thr Gln Ala Ala Ile
        355                 360                 365

Asp Gln Ile Thr Gly Lys Leu Asn Arg Leu Ile Glu Lys Thr Asn Thr
    370                 375                 380

Glu Phe Glu Ser Ile Glu Ser Glu Phe Ser Glu Thr Glu His Gln Ile
385                 390                 395                 400

Gly Asn Val Ile Asn Trp Thr Lys Asp Ser Ile Thr Asp Ile Trp Thr
                405                 410                 415

Tyr Asn Ala Glu Leu Leu Val Ala Met Glu Asn Gln His Thr Ile Asp
            420                 425                 430

Met Ala Asp Ser Glu Met Leu Asn Leu Tyr Glu Arg Val Arg Lys Gln
        435                 440                 445

Leu Arg Gln Asn Ala Glu Glu Asp Gly Lys Gly Cys Phe Glu Ile Tyr
    450                 455                 460

His Thr Cys Asp Asp Ser Cys Met Glu Ser
465                 470
```

```
<210> SEQ ID NO 25
<211> LENGTH: 477
<212> TYPE: PRT
<213> ORGANISM: Influenza A virus
<220> FEATURE:
<223> OTHER INFORMATION: Influenza A/mallard/Netherlands/7/99{H11N2}
      hemagglutinin HA1-480 domain
<220> FEATURE:
<221> NAME/KEY: VARIANT
<222> LOCATION: (148)...(148)
<223> OTHER INFORMATION: Xaa = any amino acid

<400> SEQUENCE: 25
```

```
Asp Glu Ile Cys Ile Gly Tyr Leu Ser Asn Asn Ser Thr Asp Lys Val
 1               5                  10                  15

Asp Thr Ile Ile Glu Asn Asn Val Thr Val Thr Ser Ser Val Glu Leu
            20                  25                  30

Val Glu Thr Glu His Thr Gly Ser Phe Cys Ser Ile Asn Gly Lys Gln
            35                  40                  45

Pro Ile Ser Leu Gly Asp Cys Ser Phe Ala Gly Trp Ile Leu Gly Asn
 50                  55                  60

Pro Met Cys Asp Asp Leu Ile Gly Lys Thr Ser Trp Ser Tyr Ile Val
 65                  70                  75                  80

Glu Lys Pro Asn Pro Thr Asn Gly Ile Cys Tyr Pro Gly Thr Leu Glu
                85                  90                  95

Asp Glu Glu Glu Leu Arg Leu Lys Phe Ser Gly Val Leu Glu Phe Ser
            100                 105                 110

Lys Phe Glu Ala Phe Thr Ser Asn Gly Trp Gly Ala Val Asn Ser Gly
            115                 120                 125

Ala Gly Val Thr Ala Ala Cys Lys Phe Gly Ser Ser Asn Ser Phe Phe
    130                 135                 140

Arg Asn Met Xaa Trp Leu Ile His Gln Ser Gly Thr Tyr Pro Val Ile
145                 150                 155                 160

Lys Arg Thr Phe Asn Asn Thr Lys Gly Arg Asp Val Leu Ile Val Trp
                165                 170                 175

Gly Ile His His Pro Ala Thr Leu Lys Glu His Gln Asp Leu Tyr Lys
                180                 185                 190

Lys Asp Ser Ser Tyr Val Ala Val Gly Ser Glu Thr Tyr Asn Arg Arg
            195                 200                 205

Phe Thr Pro Glu Ile Ser Thr Arg Pro Lys Val Asn Gly Gln Ala Gly
    210                 215                 220

Arg Met Thr Phe Tyr Trp Thr Met Val Lys Pro Gly Glu Ser Ile Thr
225                 230                 235                 240

Phe Glu Ser Asn Gly Ala Phe Leu Ala Pro Arg Tyr Ala Phe Glu Ile
                245                 250                 255

Val Ser Val Gly Asn Gly Lys Leu Phe Arg Ser Glu Leu Ser Ile Glu
            260                 265                 270

Ser Cys Ser Thr Lys Cys Gln Thr Glu Val Gly Gly Ile Asn Thr Asn
            275                 280                 285

Lys Ser Phe His Ser Val His Arg Asn Thr Ile Gly Asp Cys Pro Lys
    290                 295                 300

Tyr Val Asn Val Lys Ser Leu Lys Leu Ala Thr Gly Leu Arg Asn Val
305                 310                 315                 320

Pro Ala Ile Ala Ser Arg Gly Leu Phe Gly Ala Ile Ala Gly Phe Ile
                325                 330                 335

Glu Gly Gly Trp Pro Gly Leu Ile Asn Gly Trp Tyr Gly Phe Gln His
            340                 345                 350

Arg Asn Glu Glu Gly Thr Gly Ile Ala Ala Asp Arg Glu Ser Thr Gln
            355                 360                 365

Lys Ala Val Asp Gln Ile Thr Ser Lys Val Asn Asn Ile Val Asp Arg
    370                 375                 380

Met Asn Thr Asn Phe Glu Ser Leu Gln His Glu Phe Ser Glu Ile Glu
385                 390                 395                 400

Glu Arg Ile Asn Gln Leu Ser Lys His Val Asp Asp Ser Val Val Asp
                405                 410                 415
```

```
Ile Trp Ser Tyr Asn Ala Gln Leu Leu Val Leu Leu Glu Asn Glu Lys
                420                 425                 430

Thr Leu Asp Leu His Asp Ser Asn Val Arg Asn Leu His Glu Lys Val
        435                 440                 445

Arg Arg Met Leu Lys Asp Asn Ala Lys Asp Glu Gly Asn Gly Cys Phe
450                 455                 460

Thr Phe Tyr His Lys Cys Asp Asn Glu Cys Ile Glu Lys
465                 470                 475

<210> SEQ ID NO 26
<211> LENGTH: 476
<212> TYPE: PRT
<213> ORGANISM: Influenza A virus
<220> FEATURE:
<223> OTHER INFORMATION: Influenza A/duck/Alberta/60/1976{H12N5}
      hemagglutinin HA1-480 domain

<400> SEQUENCE: 26

Asp Lys Ile Cys Ile Gly Tyr Gln Thr Asn Asn Ser Thr Glu Thr Val
1               5                   10                  15

Asn Thr Leu Ser Glu Gln Asn Val Pro Val Thr Gln Val Glu Glu Leu
            20                  25                  30

Val His Gly Gly Ile Asp Pro Ile Leu Cys Gly Thr Glu Leu Gly Ser
        35                  40                  45

Pro Leu Val Leu Asp Asp Cys Ser Leu Glu Gly Leu Ile Leu Gly Asn
50                  55                  60

Pro Lys Cys Asp Leu Tyr Leu Asn Gly Arg Glu Trp Ser Tyr Ile Val
65                  70                  75                  80

Glu Arg Pro Lys Glu Met Glu Gly Val Cys Tyr Pro Gly Ser Ile Glu
                85                  90                  95

Asn Gln Glu Glu Leu Arg Ser Leu Phe Ser Ser Ile Lys Lys Tyr Glu
            100                 105                 110

Arg Val Lys Met Phe Asp Phe Thr Lys Trp Asn Val Thr Tyr Thr Gly
        115                 120                 125

Thr Ser Lys Ala Cys Asn Asn Thr Ser Asn Gln Gly Ser Phe Tyr Arg
130                 135                 140

Ser Met Arg Trp Leu Thr Leu Lys Ser Gly Gln Phe Pro Val Gln Thr
145                 150                 155                 160

Asp Glu Tyr Lys Asn Thr Arg Asp Ser Asp Ile Val Phe Thr Trp Ala
                165                 170                 175

Ile His His Pro Pro Thr Ser Asp Glu Gln Val Lys Leu Tyr Lys Asn
            180                 185                 190

Pro Asp Thr Leu Ser Ser Val Thr Thr Asp Glu Ile Asn Arg Ser Phe
        195                 200                 205

Lys Pro Asn Ile Gly Pro Arg Pro Leu Val Arg Gly Gln Gln Gly Arg
210                 215                 220

Met Asp Tyr Tyr Trp Ala Val Leu Lys Pro Gly Gln Thr Val Lys Ile
225                 230                 235                 240

Gln Thr Asn Gly Asn Leu Ile Ala Pro Glu Tyr Gly His Leu Ile Thr
                245                 250                 255

Gly Lys Ser His Gly Arg Ile Leu Lys Asn Asn Leu Pro Met Gly Gln
            260                 265                 270

Cys Val Thr Glu Cys Gln Leu Asn Glu Gly Val Met Asn Thr Ser Lys
        275                 280                 285

Pro Phe Gln Asn Thr Ser Lys His Tyr Ile Gly Lys Cys Pro Lys Tyr
290                 295                 300
```

-continued

```
Ile Pro Ser Gly Ser Leu Lys Leu Ala Ile Gly Leu Arg Asn Val Pro
305                 310                 315                 320

Gln Val Gln Asp Arg Gly Leu Phe Gly Ala Ile Ala Gly Phe Ile Glu
                325                 330                 335

Gly Gly Trp Pro Gly Leu Val Ala Gly Trp Tyr Gly Phe Gln His Gln
            340                 345                 350

Asn Ala Glu Gly Thr Gly Ile Ala Ala Asp Arg Asp Ser Thr Gln Arg
        355                 360                 365

Ala Ile Asp Asn Met Gln Asn Lys Leu Asn Asn Val Ile Asp Lys Met
    370                 375                 380

Asn Lys Gln Phe Glu Val Val Asn His Glu Phe Ser Glu Val Glu Ser
385                 390                 395                 400

Arg Ile Asn Met Ile Asn Ser Lys Ile Asp Asp Gln Ile Thr Asp Ile
                405                 410                 415

Trp Ala Tyr Asn Ala Glu Leu Leu Val Leu Leu Glu Asn Gln Lys Thr
            420                 425                 430

Leu Asp Glu His Asp Ala Asn Val Arg Asn Leu His Asp Arg Val Arg
        435                 440                 445

Arg Val Leu Arg Glu Asn Ala Ile Asp Thr Gly Asp Gly Cys Phe Glu
    450                 455                 460

Ile Leu His Lys Cys Asp Asn Asn Cys Met Asp Thr
465                 470                 475

<210> SEQ ID NO 27
<211> LENGTH: 476
<212> TYPE: PRT
<213> ORGANISM: Influenza A virus
<220> FEATURE:
<223> OTHER INFORMATION: Influenza A/gull/Maryland/704/1977{H13N6}
      hemagglutinin HA1-480 domain

<400> SEQUENCE: 27

Asp Arg Ile Cys Val Gly Tyr Leu Ser Thr Asn Ser Ser Glu Arg Val
 1               5                  10                  15

Asp Thr Leu Leu Glu Asn Gly Val Pro Val Thr Ser Ser Ile Asp Leu
            20                  25                  30

Ile Glu Thr Asn His Thr Gly Thr Tyr Cys Ser Leu Asn Gly Val Ser
        35                  40                  45

Pro Val His Leu Gly Asp Cys Ser Phe Glu Gly Trp Ile Val Gly Asn
    50                  55                  60

Pro Ala Cys Thr Ser Asn Phe Gly Thr Arg Glu Trp Ser Tyr Leu Ile
65                  70                  75                  80

Glu Asp Pro Ala Ala Pro His Gly Leu Cys Tyr Pro Gly Glu Leu Asn
                85                  90                  95

Asn Asn Gly Glu Leu Arg His Leu Phe Ser Gly Ile Arg Ser Phe Ser
            100                 105                 110

Arg Thr Glu Leu Ile Pro Pro Thr Ser Trp Gly Glu Val Leu Asp Gly
        115                 120                 125

Thr Thr Ser Ala Cys Arg Asp Asn Thr Gly Thr Asn Ser Phe Tyr Arg
    130                 135                 140

Asn Leu Val Trp Phe Ile Lys Lys Asn Asn Arg Tyr Pro Val Ile Ser
145                 150                 155                 160

Lys Thr Tyr Asn Asn Thr Thr Gly Arg Asp Val Leu Val Leu Trp Gly
                165                 170                 175

Ile His His Pro Val Ser Val Asp Glu Thr Lys Thr Leu Tyr Val Asn
```

```
                180                 185                 190
Ser Asp Pro Tyr Thr Leu Val Ser Thr Lys Ser Trp Ser Glu Lys Tyr
            195                 200                 205

Lys Leu Glu Thr Gly Val Arg Pro Gly Tyr Asn Gly Gln Arg Ser Trp
            210                 215                 220

Met Lys Ile Tyr Trp Ser Leu Ile His Pro Gly Met Ile Thr Phe
225                 230                 235                 240

Glu Ser Asn Gly Gly Phe Leu Ala Pro Arg Tyr Gly Tyr Ile Ile Glu
                245                 250                 255

Glu Tyr Gly Lys Gly Arg Ile Phe Gln Ser Arg Ile Arg Met Ser Arg
            260                 265                 270

Cys Asn Thr Lys Cys Gln Thr Ser Val Gly Gly Ile Asn Thr Asn Arg
            275                 280                 285

Thr Phe Gln Asn Ile Asp Lys Asn Ala Leu Gly Asp Cys Pro Lys Tyr
            290                 295                 300

Ile Lys Ser Gly Gln Leu Lys Leu Ala Thr Gly Leu Arg Asn Val Pro
305                 310                 315                 320

Ala Ile Ser Asn Arg Gly Leu Phe Gly Ala Ile Ala Gly Phe Ile Glu
                325                 330                 335

Gly Gly Trp Pro Gly Leu Ile Asn Gly Trp Tyr Gly Phe Gln His Gln
            340                 345                 350

Asn Glu Gln Gly Thr Gly Ile Ala Ala Asp Lys Glu Ser Thr Gln Lys
            355                 360                 365

Ala Ile Asp Gln Ile Thr Thr Lys Ile Asn Asn Ile Ile Asp Lys Met
            370                 375                 380

Asn Gly Asn Tyr Asp Ser Ile Arg Gly Glu Phe Asn Gln Val Glu Lys
385                 390                 395                 400

Arg Ile Asn Met Leu Ala Asp Arg Ile Asp Ala Val Thr Asp Ile
                405                 410                 415

Trp Ser Tyr Asn Ala Lys Leu Leu Val Leu Leu Glu Asn Asp Lys Thr
            420                 425                 430

Leu Asp Met His Asp Ala Asn Val Lys Asn Leu His Glu Gln Val Arg
            435                 440                 445

Arg Glu Leu Lys Asp Asn Ala Ile Asp Glu Gly Asn Gly Cys Phe Glu
            450                 455                 460

Leu Leu His Lys Cys Asn Asp Ser Cys Met Glu Thr
465                 470                 475

<210> SEQ ID NO 28
<211> LENGTH: 472
<212> TYPE: PRT
<213> ORGANISM: Influenza A virus
<220> FEATURE:
<223> OTHER INFORMATION: Influenza A/mallard duck/Astrakhan/263/
      1982{H14N5} hemagglutinin HA1-480 domain

<400> SEQUENCE: 28

Pro Ile Ile Cys Leu Gly His His Ala Val Glu Asn Gly Thr Ser Val
  1               5                  10                  15

Lys Thr Leu Thr Asp Asn His Val Glu Val Val Ser Ala Lys Glu Leu
            20                  25                  30

Val Glu Thr Asn His Thr Asp Glu Leu Cys Pro Ser Pro Leu Lys Leu
            35                  40                  45

Val Asp Gly Gln Asp Cys Asp Leu Ile Asn Gly Ala Leu Gly Ser Pro
       50                  55                  60
```

```
Gly Cys Asp Arg Leu Gln Asp Thr Thr Trp Asp Val Phe Ile Glu Arg
 65                  70                  75                  80

Pro Thr Ala Val Asp Thr Cys Tyr Pro Phe Asp Val Pro Asp Tyr Gln
                 85                  90                  95

Ser Leu Arg Ser Ile Leu Ala Ser Ser Gly Ser Leu Glu Phe Ile Ala
            100                 105                 110

Glu Gln Phe Thr Trp Asn Gly Val Lys Val Asp Gly Ser Ser Ser Ala
        115                 120                 125

Cys Leu Arg Gly Gly Arg Asn Ser Phe Phe Ser Arg Leu Asn Trp Leu
    130                 135                 140

Thr Lys Ala Thr Asn Gly Asn Tyr Gly Pro Ile Asn Val Thr Lys Glu
145                 150                 155                 160

Asn Thr Gly Ser Tyr Val Arg Leu Tyr Leu Trp Gly Val His His Pro
                165                 170                 175

Ser Ser Asp Asn Glu Gln Thr Asp Leu Tyr Lys Val Ala Thr Gly Arg
            180                 185                 190

Val Thr Val Ser Thr Arg Ser Asp Gln Ile Ser Ile Val Pro Asn Ile
        195                 200                 205

Gly Ser Arg Pro Arg Val Arg Asn Gln Ser Gly Arg Ile Ser Ile Tyr
    210                 215                 220

Trp Thr Leu Val Asn Pro Gly Asp Ser Ile Ile Phe Asn Ser Ile Gly
225                 230                 235                 240

Asn Leu Ile Ala Pro Arg Gly His Tyr Lys Ile Ser Lys Ser Thr Lys
                245                 250                 255

Ser Thr Val Leu Lys Ser Asp Lys Arg Ile Gly Ser Cys Thr Ser Pro
            260                 265                 270

Cys Leu Thr Asp Lys Gly Ser Ile Gln Ser Asp Lys Pro Phe Gln Asn
        275                 280                 285

Val Ser Arg Ile Ala Ile Gly Asn Cys Pro Lys Tyr Val Lys Gln Gly
    290                 295                 300

Ser Leu Met Leu Ala Thr Gly Met Arg Asn Ile Pro Gly Lys Gln Ala
305                 310                 315                 320

Lys Gly Leu Phe Gly Ala Ile Ala Gly Phe Ile Glu Asn Gly Trp Gln
                325                 330                 335

Gly Leu Ile Asp Gly Trp Tyr Gly Phe Arg His Gln Asn Ala Glu Gly
            340                 345                 350

Thr Gly Thr Ala Ala Asp Leu Lys Ser Thr Gln Ala Ala Ile Asp Gln
        355                 360                 365

Ile Asn Gly Lys Leu Asn Arg Leu Ile Glu Lys Thr Asn Glu Lys Tyr
    370                 375                 380

His Gln Ile Glu Lys Glu Phe Glu Gln Val Glu Gly Arg Ile Gln Asp
385                 390                 395                 400

Leu Glu Lys Tyr Val Glu Asp Thr Lys Ile Asp Leu Trp Ser Tyr Asn
                405                 410                 415

Ala Glu Leu Leu Val Ala Leu Glu Asn Gln His Thr Ile Asp Val Thr
            420                 425                 430

Asp Ser Glu Met Asn Lys Leu Phe Glu Arg Val Arg Arg Gln Leu Arg
        435                 440                 445

Glu Asn Ala Glu Asp Gln Gly Asn Gly Cys Phe Glu Ile Phe His Gln
    450                 455                 460

Cys Asp Asn Asn Cys Ile Glu Ser
465                 470
```

<210> SEQ ID NO 29
<211> LENGTH: 482
<212> TYPE: PRT
<213> ORGANISM: Influenza A virus
<220> FEATURE:
<223> OTHER INFORMATION: Influenza A/duck/Australia/341/83{H15N8} hemagglutinin HA1-480 domain

<400> SEQUENCE: 29

```
Asp Lys Ile Cys Leu Gly His His Ala Val Ala Asn Gly Thr Lys Val
 1               5                   10                  15

Asn Thr Leu Thr Glu Lys Gly Val Glu Val Val Asn Ala Thr Glu Thr
            20                  25                  30

Val Glu Ile Thr Gly Ile Asn Lys Val Cys Thr Lys Gly Lys Lys Ala
        35                  40                  45

Val Asp Leu Gly Ser Cys Gly Ile Leu Gly Thr Ile Ile Gly Pro Pro
    50                  55                  60

Gln Cys Asp Ser His Leu Lys Phe Lys Ala Asp Leu Ile Ile Glu Arg
65                  70                  75                  80

Arg Asn Ser Ser Asp Ile Cys Tyr Pro Gly Lys Phe Thr Asn Glu Glu
                85                  90                  95

Ala Leu Arg Gln Ile Ile Arg Glu Ser Gly Gly Ile Asp Lys Glu Pro
            100                 105                 110

Met Gly Phe Arg Tyr Ser Gly Ile Lys Thr Asp Gly Ala Thr Ser Ala
        115                 120                 125

Cys Lys Arg Thr Val Ser Ser Phe Tyr Ser Glu Met Lys Trp Leu Leu
    130                 135                 140

Ser Ser Lys Asp Asn Gln Val Phe Pro Gln Leu Asn Gln Thr Tyr Arg
145                 150                 155                 160

Asn Asn Arg Lys Glu Pro Ala Leu Ile Val Trp Gly Val His His Ser
                165                 170                 175

Ser Ser Leu Asp Glu Gln Asn Lys Leu Tyr Gly Ala Gly Asn Lys Leu
            180                 185                 190

Ile Thr Val Gly Ser Ser Lys Tyr Gln Gln Ser Phe Ser Pro Ser Pro
        195                 200                 205

Gly Asp Arg Pro Lys Val Asn Gly Gln Ala Gly Arg Ile Asp Phe His
    210                 215                 220

Trp Met Leu Leu Asp Pro Gly Asp Thr Val Thr Phe Thr Phe Asn Gly
225                 230                 235                 240

Ala Phe Ile Ala Pro Asp Arg Ala Thr Phe Leu Arg Ser Asn Ala Pro
                245                 250                 255

Ser Gly Val Glu Tyr Asn Gly Lys Ser Leu Gly Ile Gln Ser Asp Ala
            260                 265                 270

Gln Ile Asp Glu Ser Cys Glu Gly Glu Cys Phe Tyr Ser Gly Gly Thr
        275                 280                 285

Ile Asn Ser Pro Leu Pro Phe Gln Asn Ile Asp Ser Trp Ala Val Gly
    290                 295                 300

Arg Cys Pro Arg Tyr Val Lys Gln Ser Ser Leu Pro Leu Ala Leu Gly
305                 310                 315                 320

Met Lys Asn Val Pro Glu Lys Ile His Thr Arg Gly Leu Phe Gly Ala
                325                 330                 335

Ile Ala Gly Phe Ile Glu Asn Gly Trp Glu Gly Leu Ile Asp Gly Trp
            340                 345                 350

Tyr Gly Phe Arg His Gln Asn Ala Gln Gly Gln Gly Thr Ala Ala Asp
        355                 360                 365
```

```
Tyr Lys Ser Thr Gln Ala Ala Ile Asp Gln Ile Thr Gly Lys Leu Asn
    370                 375                 380
Arg Leu Ile Glu Lys Thr Asn Thr Gln Phe Glu Leu Ile Asp Asn Glu
385                 390                 395                 400
Phe Thr Glu Val Glu Gln Gln Ile Gly Asn Val Ile Asn Trp Thr Arg
                405                 410                 415
Asp Ser Leu Thr Glu Ile Trp Ser Tyr Asn Ala Glu Leu Leu Val Ala
            420                 425                 430
Met Glu Asn Gln His Thr Ile Asp Leu Ala Asp Ser Glu Met Asn Lys
        435                 440                 445
Leu Tyr Glu Arg Val Arg Arg Gln Leu Arg Glu Asn Ala Glu Glu Asp
450                 455                 460
Gly Thr Gly Cys Phe Glu Ile Phe His Arg Cys Asp Asp Gln Cys Met
465                 470                 475                 480
Glu Ser
```

<210> SEQ ID NO 30
<211> LENGTH: 474
<212> TYPE: PRT
<213> ORGANISM: Influenza A virus
<220> FEATURE:
<223> OTHER INFORMATION: Influenza A/shorebird/New Jersey/840/
      1986{H16N3} hemagglutinin HA1-480 domain

<400> SEQUENCE: 30

```
Asp Lys Ile Cys Ile Gly Tyr Leu Ser Asn Asn Ser Ser Asp Thr Val
1               5                   10                  15
Asp Thr Leu Thr Glu Asn Gly Val Pro Val Thr Ser Ser Ile Asp Leu
            20                  25                  30
Val Glu Thr Asn His Thr Gly Thr Tyr Cys Ser Leu Asn Gly Ile Ser
        35                  40                  45
Pro Ile His Leu Gly Asp Cys Ser Phe Glu Gly Trp Ile Val Gly Asn
50                  55                  60
Pro Ser Cys Ala Thr Asn Ile Asn Ile Arg Glu Trp Ser Tyr Leu Ile
65                  70                  75                  80
Glu Asp Pro Asn Ala Pro Asn Lys Leu Cys Phe Pro Gly Glu Leu Asp
                85                  90                  95
Asn Asn Gly Glu Leu Arg His Leu Phe Ser Gly Val Asn Ser Phe Ser
            100                 105                 110
Arg Thr Glu Leu Ile Ser Pro Ser Lys Trp Gly Asp Val Leu Asp Gly
        115                 120                 125
Val Thr Ala Ser Cys Leu Asp Lys Gly Ala Ser Ser Phe Tyr Arg Asn
130                 135                 140
Leu Val Trp Leu Val Lys Gln Asn Asp Arg Tyr Pro Val Val Arg Gly
145                 150                 155                 160
Asp Tyr Asn Asn Thr Thr Gly Arg Asp Val Leu Val Leu Trp Gly Ile
                165                 170                 175
His His Pro Asp Thr Glu Thr Thr Ala Thr Lys Leu Tyr Val Asn Lys
            180                 185                 190
Asn Pro Tyr Thr Leu Val Ser Thr Lys Glu Trp Ser Lys Arg Tyr Glu
        195                 200                 205
Leu Glu Ile Gly Thr Arg Ile Gly Asp Gly Gln Arg Ser Trp Met Lys
210                 215                 220
Ile Tyr Trp His Leu Met His Pro Gly Glu Arg Ile Met Phe Glu Ser
225                 230                 235                 240
```

Asn Gly Gly Leu Leu Ala Pro Arg Tyr Gly Tyr Ile Ile Glu Lys Tyr
                245                 250                 255

Gly Thr Gly Arg Ile Phe Gln Ser Gly Ile Arg Met Ala Lys Cys Asn
            260                 265                 270

Thr Lys Cys Gln Thr Ser Met Gly Gly Val Asn Thr Asn Lys Thr Phe
        275                 280                 285

Gln Asn Ile Glu Arg Asn Ala Leu Gly Asp Cys Pro Lys Tyr Ile Lys
    290                 295                 300

Ser Gly Gln Leu Lys Leu Ala Thr Gly Leu Arg Asn Val Pro Ser Ile
305                 310                 315                 320

Gly Glu Arg Gly Leu Phe Gly Ala Ile Ala Gly Phe Ile Glu Gly Gly
                325                 330                 335

Trp Pro Gly Leu Ile Asn Gly Trp Tyr Gly Phe Gln His Gln Asn Glu
            340                 345                 350

Gln Gly Thr Gly Ile Ala Ala Asp Lys Ala Ser Thr Gln Lys Ala Ile
        355                 360                 365

Asn Glu Ile Thr Thr Lys Ile Asn Asn Ile Ile Glu Lys Met Asn Gly
    370                 375                 380

Asn Tyr Asp Ser Ile Arg Gly Glu Phe Asn Gln Val Glu Lys Arg Ile
385                 390                 395                 400

Asn Met Leu Ala Asp Arg Val Asp Asp Ala Val Thr Asp Ile Trp Ser
                405                 410                 415

Tyr Asn Ala Lys Leu Leu Val Leu Ile Glu Asn Asp Arg Thr Leu Asp
            420                 425                 430

Leu His Asp Ala Asn Val Lys Asn Leu His Glu Gln Val Lys Arg Ala
        435                 440                 445

Leu Lys Asn Asn Ala Ile Asp Glu Gly Asp Gly Cys Phe Asn Leu Leu
    450                 455                 460

His Lys Cys Asn Asp Ser Cys Met Glu Thr
465                 470

<210> SEQ ID NO 31
<211> LENGTH: 8
<212> TYPE: PRT
<213> ORGANISM: Artificial Sequence
<220> FEATURE:
<223> OTHER INFORMATION: synthetic Influenza A/Indonesia/5/2005(H5N1),
      A/Viet Nam/1203/2004(H5N1) and A/Berkeley/1/68(H2N2) hemagglutinin
      (HA) N-terminal sequence

<400> SEQUENCE: 31

Asp Gln Ile Cys Ile Gly Tyr His
1               5

<210> SEQ ID NO 32
<211> LENGTH: 8
<212> TYPE: PRT
<213> ORGANISM: Artificial Sequence
<220> FEATURE:
<223> OTHER INFORMATION: synthetic Influenza A/California/04/2009(H1N1)
      and A/swine/Wisconsin/1/1968(H1N1) hemagglutinin (HA) N-terminal
      sequence

<400> SEQUENCE: 32

Asp Thr Leu Cys Ile Gly Tyr His
1               5

<210> SEQ ID NO 33
<211> LENGTH: 8
<212> TYPE: PRT

```
<213> ORGANISM: Artificial Sequence
<220> FEATURE:
<223> OTHER INFORMATION: synthetic Influenza A/New Caledonia/6/
      2008(H1N1), A/South Carolina/1/18(H1N1), A/Denver/57(H1N1) and
      A/Hong Kong/117/77(H1N1) hemagglutinin (HA) N-terminal sequence

<400> SEQUENCE: 33

Asp Thr Ile Cys Ile Gly Tyr His
1               5

<210> SEQ ID NO 34
<211> LENGTH: 8
<212> TYPE: PRT
<213> ORGANISM: Artificial Sequence
<220> FEATURE:
<223> OTHER INFORMATION: synthetic Influenza A/Victoria/210/2009(H3N2)
      and A/Wisconsin/15/2009(H3N2) hemagglutinin (HA) N-terminal
      sequence

<400> SEQUENCE: 34

Ala Thr Leu Cys Leu Gly His His
1               5

<210> SEQ ID NO 35
<211> LENGTH: 8
<212> TYPE: PRT
<213> ORGANISM: Artificial Sequence
<220> FEATURE:
<223> OTHER INFORMATION: synthetic Influenza A/chicken/Alabama/1/
      1975(H4N8) hemagglutinin (HA) N-terminal sequence

<400> SEQUENCE: 35

Pro Val Ile Cys Leu Gly His His
1               5

<210> SEQ ID NO 36
<211> LENGTH: 8
<212> TYPE: PRT
<213> ORGANISM: Artificial Sequence
<220> FEATURE:
<223> OTHER INFORMATION: synthetic Influenza A/mallard/Ohio/170/
      1999(H6N5) hemagglutinin (HA) N-terminal sequence

<400> SEQUENCE: 36

Asp Arg Ile Cys Ile Gly Tyr His
1               5

<210> SEQ ID NO 37
<211> LENGTH: 8
<212> TYPE: PRT
<213> ORGANISM: Artificial Sequence
<220> FEATURE:
<223> OTHER INFORMATION: synthetic Influenza A/Netherlands/219/03(H7N7)
      and A/duck/Australia/341/83(H15N8) hemagglutinin (HA) N-terminal
      sequence

<400> SEQUENCE: 37

Asp Lys Ile Cys Leu Gly His His
1               5

<210> SEQ ID NO 38
<211> LENGTH: 8
<212> TYPE: PRT
<213> ORGANISM: Artificial Sequence
<220> FEATURE:
<223> OTHER INFORMATION: synthetic Influenza A/duck/Alaska/702/
      1991(H8N2) hemagglutinin (HA) N-terminal sequence

<400> SEQUENCE: 38
```

Asp Arg Ile Cys Ile Gly Tyr Gln
1 5

<210> SEQ ID NO 39
<211> LENGTH: 8
<212> TYPE: PRT
<213> ORGANISM: Artificial Sequence
<220> FEATURE:
<223> OTHER INFORMATION: synthetic Influenza A/Hong Kong/1073/99(H9N2) hemagglutinin (HA) N-terminal sequence

<400> SEQUENCE: 39

Asp Lys Ile Cys Ile Gly His Gln
1 5

<210> SEQ ID NO 40
<211> LENGTH: 8
<212> TYPE: PRT
<213> ORGANISM: Artificial Sequence
<220> FEATURE:
<223> OTHER INFORMATION: synthetic Influenza A/chicken/Germany/N/1949(H10N7) hemagglutinin (HA) N-terminal sequence

<400> SEQUENCE: 40

Asp Arg Ile Cys Leu Gly His His
1 5

<210> SEQ ID NO 41
<211> LENGTH: 8
<212> TYPE: PRT
<213> ORGANISM: Artificial Sequence
<220> FEATURE:
<223> OTHER INFORMATION: synthetic Influenza A/mallard/Netherlands/7/99(H11N2) hemagglutinin (HA) N-terminal sequence

<400> SEQUENCE: 41

Asp Glu Ile Cys Ile Gly Tyr Leu
1 5

<210> SEQ ID NO 42
<211> LENGTH: 8
<212> TYPE: PRT
<213> ORGANISM: Artificial Sequence
<220> FEATURE:
<223> OTHER INFORMATION: synthetic Influenza A/duck/Alberta/60/1976(H12N5) hemagglutinin (HA) N-terminal sequence

<400> SEQUENCE: 42

Asp Lys Ile Cys Ile Gly Tyr Gln
1 5

<210> SEQ ID NO 43
<211> LENGTH: 8
<212> TYPE: PRT
<213> ORGANISM: Artificial Sequence
<220> FEATURE:
<223> OTHER INFORMATION: synthetic Influenza A/gull/Maryland/704/1977(H13N6) hemagglutinin (HA) N-terminal sequence

<400> SEQUENCE: 43

Asp Arg Ile Cys Val Gly Tyr Leu
1 5

<210> SEQ ID NO 44
<211> LENGTH: 8
<212> TYPE: PRT
<213> ORGANISM: Artificial Sequence

```
<220> FEATURE:
<223> OTHER INFORMATION: synthetic Influenza A/mallard duck/Astrakhan/
      263/1982(H14N5) hemagglutinin (HA) N-terminal sequence

<400> SEQUENCE: 44

Pro Ile Ile Cys Leu Gly His His
1               5

<210> SEQ ID NO 45
<211> LENGTH: 8
<212> TYPE: PRT
<213> ORGANISM: Artificial Sequence
<220> FEATURE:
<223> OTHER INFORMATION: synthetic Influenza A/shorebird/New Jersey/840/
      1986(H16N3) hemagglutinin (HA) N-terminal sequence

<400> SEQUENCE: 45

Asp Lys Ile Cys Ile Gly Tyr Leu
1               5

<210> SEQ ID NO 46
<211> LENGTH: 4
<212> TYPE: PRT
<213> ORGANISM: Artificial Sequence
<220> FEATURE:
<223> OTHER INFORMATION: synthetic Influenza A hemagglutinin (HA) highly
      conserved N-terminal sequence

<400> SEQUENCE: 46

Ile Cys Ile Gly
1

<210> SEQ ID NO 47
<211> LENGTH: 7
<212> TYPE: PRT
<213> ORGANISM: Artificial Sequence
<220> FEATURE:
<223> OTHER INFORMATION: synthetic fusion protein flexible linker

<400> SEQUENCE: 47

Gly Gly Gly Pro Gly Gly Gly
1               5

<210> SEQ ID NO 48
<211> LENGTH: 6
<212> TYPE: PRT
<213> ORGANISM: Artificial Sequence
<220> FEATURE:
<223> OTHER INFORMATION: synthetic six histidine residues, polyhistidine
      tract, His-tag, C-terminus His-6 tag, affinity purification
      sequence, detection- and purification-facilitating domain

<400> SEQUENCE: 48

His His His His His His
1               5
```